US007981997B2

(12) United States Patent
Harari et al.

(10) Patent No.: US 7,981,997 B2
(45) Date of Patent: Jul. 19, 2011

(54) GROWTH FACTOR WHICH ACTS THROUGH ERBB-4 RTK

(75) Inventors: Daniel Harari, Rechovot (IL); Yosef Yarden, Rechovot (IL)

(73) Assignee: Yeda Research And Development Co., Rehovot (IL)

( * ) Notice: Subject to any disclaimer, the term of this patent is extended or adjusted under 35 U.S.C. 154(b) by 0 days.

(21) Appl. No.: 12/539,636

(22) Filed: Aug. 12, 2009

(65) Prior Publication Data

US 2010/0048863 A1 Feb. 25, 2010

Related U.S. Application Data

(60) Division of application No. 11/492,124, filed on Jul. 25, 2006, now abandoned, which is a division of application No. 10/240,411, filed as application No. PCT/IL01/00371 on Apr. 20, 2001, now Pat. No. 7,094,882, which is a continuation-in-part of application No. 09/553,769, filed on Apr. 21, 2000, now Pat. No. 6,544,759.

(51) Int. Cl.
*C07K 5/00* (2006.01)
*C07K 14/00* (2006.01)

(52) U.S. Cl. ......................... 530/300; 530/324; 530/350

(58) Field of Classification Search ........................ None
See application file for complete search history.

(56) References Cited

U.S. PATENT DOCUMENTS

| | | | | |
|---|---|---|---|---|
| 4,474,893 | A | 10/1984 | Reading | |
| 5,350,836 | A | 9/1994 | Kopchick et al. | |
| 5,356,775 | A | 10/1994 | Hebert et al. | |
| 5,585,089 | A | 12/1996 | Queen et al. | |
| 6,544,759 | B1 | 4/2003 | Harari et al. | |
| 6,825,333 | B1 * | 11/2004 | Kavanaugh et al. | 536/23.5 |
| 7,094,882 | B2 | 8/2006 | Harari et al. | |
| 2004/0121326 | A1 | 6/2004 | Harari et al. | |
| 2007/0015196 | A1 | 1/2007 | Harari et al. | |

FOREIGN PATENT DOCUMENTS

| | | |
|---|---|---|
| WO | WO 98/50071 | 11/1998 |
| WO | WO 98/50556 | 11/1998 |
| WO | WO 99/07870 | 2/1999 |
| WO | WO 99/11813 | 3/1999 |
| WO | WO 99/19489 | 4/1999 |
| WO | WO 99/33962 | 7/1999 |
| WO | WO 00/39302 | 7/2000 |
| WO | WO 00/71574 | 11/2000 |
| WO | WO 01/14415 | 3/2001 |
| WO | WO 01/81540 | 11/2001 |

OTHER PUBLICATIONS

Harari et al., Oncogene, Apr. 29, 1999, vol. 18(17):2681-2689.*
Official Action Dated Nov. 3, 2008 From the US Patent and Trademark Office Re.: U.S. Appl. No. 11/492,124.
Official Action Dated May 12, 2009 From the US Patent and Trademark Office Re.: U.S. Appl. No. 11/492,124.
Official Action Dated Jun. 27, 2008 From the US Patent and Trademark Office Re.: U.S. Appl. No. 11/492,124.
Response Dated Feb. 2, 2009 of Official Action of Nov. 3, 2008 From the US Patent and Trademark Office Re.: U.S. Appl. No. 11/492,124.
Alimandi et al. "Epidermal Growth Factor and Betacellulin Mediate Signal Transduction Through Co-Expressed ErbB2 and ErbB3 Receptors", EMBO J., 15; 16(18): 5608-5617, 1997.
Barbacci et al. "The Structural Basis for the Specificity of Epidermal Growth Factor and Heregulin Binding", J. Biol. Chem., 270(16): 9585-9589, 1995. Erratum in: J. Biol. Chem., 270(47): 28494, 1995.
Ben-Baruch et al. "Neu Differentiation Factors: A Family of Alternatively Spliced Neuronal and Mesenchymal Factors", Proc. Soc. Exp. Biol. Med., 206(3): 221-227, 1994.
Burden et al. "Neuregulins and Their Receptors: A Versatile Signaling Module in Organogenesis and Oncogenesis", Neuron, 18(6): 847-855, 1997.
Caraway III et al. "Neuregulin-2, A New Ligand of ErbB3/ErbB4-Receptor Tyrosine Kinases", Nature, 387: 512-516, 1997.
Chang et al. "Ligands for ErbB-Family Receptors Encoded by A Neuregulin-Like Gene", Nature, 387: 509-512, 1997.
Chang et al. "The Expression of Type I Growth Factor Receptors in the Squamous Neoplastic Changes of Uterine Cervix", J. Biomed. Sci., 8(2): 206-213, 2001.
Chen et al. "An Immunological Approach Reveals Biological Differences Between the Two NDF/Heregulin Receptors, ErbB-3 and ErbB-4", J. Biol. Chem., 271(13): 7620-2629, 1996.
Cohen et al. "The Relationship Between Human Epidermal Growth-Like Factor Receptor Expression and Cellular Transformation in NIH3T3 Cells", J. Biol. Chem., 271(48): 30897-30903, 1996.
Di Fiore et al. "A Single Amino Acid Substitution Is Sufficient to Modify the Mitogenic Properties of the Epidermal Growth Factor Receptor to Resemble That of GP185erbB-2", The EMBO Journal, 11(11): 3927-3933, 1992.
Elenius et al. "Activation of HER4 by Heparin-Binding EGF-Like Growth Factor Stimulates Chemotaxis But Not Proliferation", EMBO J., 16(6): 1268-1278, 1997.
Gassman et al. "Aberrant Neural and Cardiac Development in Mice Lacking the ErbB4 Neuregulin Receptor", Nature, 378: 390-395, 1995.
Gilbertson et al. "Expression of the ErbB-Neuregulin Signaling Network During Human Cerebellar Development: Implications for the Biology of Medulloblastoma", Cancer Res., 58(17): 3932-3941, 1998. Abstract.
Gilbertson et al. "Prognostic Significance of HER2 and HER4 Coexpression in Childhood Medulloblastoma", Cancer Res. 57(15): 3272-3280, 1997. Abstract.
Gilmour et al. "Expression of ErbB-4/HER-4 Growth Factor Receptor Isoforms in Ovarian Cancer", Cancer Res., 61(5): 2169-2176, 2001.
Graber et al. "ErbB-4 mRNA Expression Is Decreased in Non-Metastatic Pancreatic Cancer", Int. J. Cancer, 84(1): 24-27, 1999.
Harari et al. "Neuregulin-4: A Novel Growth Factor That Acts Through the ErbB-4 Receptor Tyrosine Kinase", Oncogene, 18: 2681-2689, 1999.
Hayes et al. "Identification and Characterization of Novel Spliced Variants of Neuregulin 4 in Prostate Cancer", Clinical Cancer Research, 13(11): 3147-3155, Jun. 1, 2007.

(Continued)

*Primary Examiner* — Elizabeth C Kemmerer
*Assistant Examiner* — Xiaozhen Xie

(57) ABSTRACT

The present invention provides for isolated polypeptides capable of binding ErbB-4.

4 Claims, 11 Drawing Sheets

OTHER PUBLICATIONS

Higashiyama et al. "A Heparin-Binding Growth Factor Secreted by Macrophage-Like Cells That Is Related to EGF", Science, 251: 936-939, 1991.
Higashiyama et al. "A Novel Brain-Derived Member of the Epidermal Growth Factor Family That Interacts With ErbB3 and ErbB4", J. Biochem., 122(3): 675-680, 1997.
Holmes et al. "Identification of Heregulin, A Specific Activator of P185ErbB2", Science, 256(5060): 1205-1210, 1992.
Ibrahim et al. "Expression of c-erbB Proto-Oncogene Family Members in Squamous Cell Carcinoma of the Head and Neck", Anticancer Res., 17(6D): 4539-4546, 1997. Abstract.
Jones et al. "Binding Interaction of the Heregulinbeta EGF Domain With ErbB3 and ErbB4 Receptors Assessed by Alanine Scanning Mutagenesis", J. Biol. Chem., 273(19): 11667-11674, 1998.
Karunagaran et al. "ErbB-2 Is A Common Auxiliary Subunit of NDF and EGF Receptors: Implications for Breast Cancer", EMBO J., 15(2): 254-264, 1996.
Klapper et al. "Biochemical and Clinical Implications of the ErbB/HER Signal Network of Growth Factor Receptors", Adv. Cancer Res., 7: 25-79, 2000. Abstract.
Krahn et al. "Coexpression Patterns of EGFR, HER2, HER3 and HER4 in Non-Melanoma Skin Cancer", Eur. J. Cancer, 37(2): 251-259, 2001. Abstract.
Kritzik et al. "Expression of ErbB Receptors During Pancreatic Islet Development and Regrowth", J. Endocrinol., 165(1): 67-77, 2000.
Lee et al. "Requirement for Neuregulin Receptors ErbB2 in Neural and Cardiac Development", Nature, 378: 394-398, 1995.
Lin et al. "Synthesis of A Biological Active Tumor Growth Factor From the Predicted DNA Sequence of Shope Fibroma Virus", Biochemistry, 27(15): 5640-5645, 1988.
Lyne et al. "Tissue Expression of Neu Differentiation Factor/Heregulin and Its Receptor Complex in Prostate Cancer and Its Biologic Effects on Prostate Cancer Cells In Vitro", Cancer J. Sci. Am., 3(1): 21-30, 1997. Abstract.
Marchionni et al. "Glial Growth Factors Are Alternatively Spliced ErbB2 Ligands Expressed in the Nervous System", Nature, 362: 312-318, 1993.
Marquardt et al. "Rat Transforming Growth Factor Type 1: Structure and Relation to Epidermal Growth Factor", Science, 223: 1079-1082, 1984.
Memon et al. "Expression of HER3, HER4, and Their Ligand Heregulin-4 Is Associated With Better Survival in Bladder Cancer Patients", British Journal of Cancer, 91: 2034-2041, 2004.
Meyer et al. "Multiple Essential Functions of Neuregulin in Development", Nature, 378: 386-390, 1995. Erratum in: Nature, 378: 753, 1995.
Olayioye et al. "The ErbB Signaling Network: Receptor Heterodimerization in Development and Cancer", The EMBO Journal, 19(13): 3159-3167, 2000.
Ozawa et al. "Growth Factors and Their Receptors in Pancreatic Cancer", Teratog. Carcinog. Mutagen., 21(1): 27-44, 2001.
Peles et al. "Isolation of the Neu/HER-2 Stimulatory Ligand: A 44 Kd Glycoprotein That Induces Differentiation of Mammary Tumor Cells", Cell, 69(1): 205-216, 1992.
Pinkas-Kramarski et al. "ErbB Tyrosine Kinases and the Two Neuregulin Families Constitute A Ligand-Receptor Network", Mol. Cell Biol., 19(12): 86-95, 1999.
Révillion et al. "ErbB/HER Ligands in Human Breast Cancer, and Relationship With Their Receptors, the Bio-Pathological Features and Prognosis", Annals of Oncology, 19: 73-80, 2008.
Ricci et al. "Expression of HER/ErbB Family of Receptor Tyrosine Kinases and Induction of Differentiation by Glial Growth Factor 2 in Human Rhabdomyosarcoma Cells", Int. J. Cancer, 87(1): 29-36, 2000. Abstract.
Riese II et al. "Betacellulin Activates the Epidermal Growth Factor Receptor and ErbB-4, and Induces Cellular Response Patterns Distinct From Those Stimulated by Epidermal Growth Factor or Neuregulin-Beta", Oncogene, 12(2): 345-353, 1996.
Riethmacher et al. "Severe Neuropathies in Mice With Targeted Mutations in the ErbB3 Receptor", Nature, 389: 725-730, 1997.
Shing et al. "Betacellulin: A Mitogen From Pancreatic Beta Cell Tumors", Science, 259: 1604-1607, 1993.
Srinivasan et al. "Expression of the C-ErbB-3/HER-3 and C-ErbB-4/HER-4 Growth Factor Receptors and Their Ligands, Neuregulin-1 Alpha, Neuregulin-1 Beta, and Betacellulin, in Normal Endometrium and Endometrial Cancer", Clin. Cancer Res., 5(10): 2877-2883, 1999. Abstract.
Srinivasan et al. "Expression of the C-ErbB-4/HER4 Protein and mRNA in Normal Human Fetal and Adult Tissues and in A Survey of Nine Solid Tumour Types", J. Pathol., 185(3): 236-245, 1998. Abstract.
Srinivasan et al. "Nuclear Expression of the C-ErbB-4/HER-4 Growth Factor Receptor in Invasive Breast Cancers", Cancer Res., 60(6): 1483-1487, 2000. Abstract.
Toyoda et al. "Epiregulin. A Novel Epidermal Growth Factor With Mitogenic Activity for Rat Primary Hepatocytes", J. Biol. Chem., 270(13): 7495-7500, 1995.
Tzahar et al. "The ErbB-2/HER2 Oncogenic Receptor of Adenocarcinomas: From Orphanhood to Multiple Stromal Ligands", Biochim. Biophys. Acta, 1377(1): M25-M37, 1998.
Wells "Additivity of Mutational Effects in Protein", Biochem., 29(37): 8509-8517, 1990. Table II.
Wen et al. "Neu Differentiation Factor: A Transmembrane Glycoprotein Containing An EGF Domain and An Immunoglobulin Homology Unit", Cell, 69(3): 559-572, 1992.
Zhang et al. "Neuregulin-3 (NRG3): A Novel Neural Tissue-Enriched Protein That Binds and Activates ErbB4", Proc. Natl. Acad. Sci. USA, 94(18): 9562-2567, 1997.
Yarden et al. "Untangling the ErbB Signalling Network", Nat. Rev. Mol. Cell. Biol., 2(2): 127-137, 2001. Abstract.

* cited by examiner

```
  1  AAACGCTGCATGTCTAGCAAAATTTTCTTTTTTTATGGGAATATAAATTTCTGTTGAGGT   (SEQ ID NO:1)
 61  GCTGATTTTCAACCTTAATTCTTCCATCAAGAATGAAACTATTTAAAAATTAAGATGCCA
                                                             M  P    2 (SEQ ID NO:2)

121  ACAGATCACGAGCAGCCCTGTGGTCCCAGGCACAGGTCATTTTGCCTCAATGGGGGGATT
     T  D  H  E  Q  P  C  G  P  R  H  R  S  F  C  L  N  G  G  I     22

181  TGTTATGTGATCCCTACTATCCCCAGCCCATTCTGTAGGTGCATTGAAAATTACACCGGA
     C  Y  V  I  P  T  I  P  S  P  F  C  R  C  I  E  N  Y  T  G     42

241  GCACGCTGCGAAGAGGTTTTTCTCCCAAGCTCCAGCATCCCAAGCGAAAGTAATCTGTCG
     A  R  C  E  E  V  F  L  P  S  S  S  I  P  S  E  S  N  L  S     62

301  GCAGCTTTCGTGGTGCTGGCGGTCCTCCTCACTCTTACCATCGCGGCGCTCTGCTTCCTG
     A  A  F  V  V  L  A  V  L  L  T  L  T  I  A  A  L  C  F  L     82

361  TGCAGGAAGGGCCACCTTCAGAGGGCCAGTTCAGTCCAGTGTGAGATCAGCCTGGTAGAG
     C  R  K  G  H  L  Q  R  A  S  S  V  Q  C  E  I  S  L  V  E    102

421  ACAAACAATACCAGAACCCGTCACAGCCACAGAGAACACTGAAGACATACATCCCCAGTG
     T  N  N  T  R  T  R  H  S  H  R  E  H  *                      115

481  AAGGGCATCATTACCTACAAAGGCGGACTGTGGACCATACGACGAGAGAAGCCCATCATC
541  ATGGATGTGTCCCATCATTTCTATGGCAGTCCCAGGATCTCACTCTTCTTGATGCTCTAC
601  TGTTTGATTGTTCATCGTTCACATACAGAAATGACGCTGGTTTCCTGTGTTGACCTTGCA
661  CCCTGCTACTGTCATCACTGGCCTGGAAGTCAGCAGTATAGATAAGGCTGGCCCTGAATT
721  CAAGAGACTCACCTGTTTTTGCCTACTCAGAGTTACTGGAATTAAAGGCATAACAACAAA
781  AAAAAAAAAAAAAAAAAAGA
```

Fig. 1a

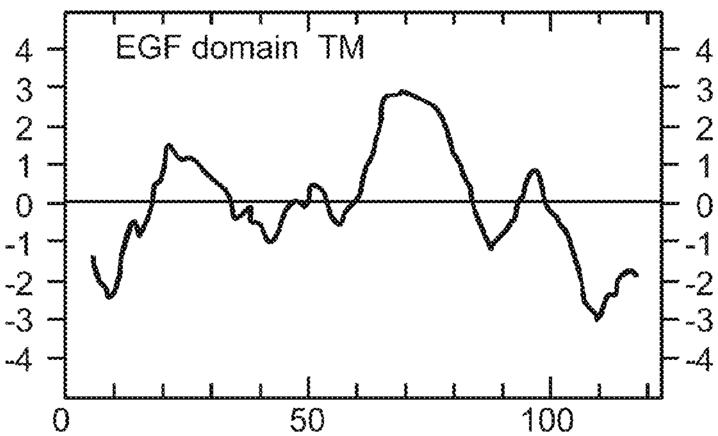

Fig. 1b

```
                      A          B                  C
                                                              SEQ ID NO:
NRG-4         DHEQPCGPRHRSFCLNGGICYVIPTIPSPF...CRCIENYTGARCEEVFL   3

NRG-1β        SHLIKCAEKEKTFCVNGGECFTVKDLSNPSRYLCKCPNEFTGDRCQN.YV   4
NRG-2         GHARKCNETAKSYCVNGGVCYYIEGINQLS...CKCPVGYTGDRCQQ.FA   5
NRG-3         EHFKPCRDKDLAYCLNDGECFVIETLTG.SHKHCRCKEGYQGVRCDQ.FL   6

mouse EGF     NSYPGCPSSYDGYCLNGGVCMHIESLDSYT...CNCVIGYSGDRCQTRDL   7
human EGF     NSDSECPLSHDGYCLHDGVCMYIEALDKYA...CNCVVGYIGERCQYRDL   8

TGFα          SHFNKCPDSHTQYCFH.GTCRFLVQEEKPA...CVCHSGYVGVRCEHADL   9
Betacellulin  THFSRCPKQYKHYCIH.GRCRFVVDEQTPS...CICEKGYFGARCERVDL   10
Epiregulin    VQITKCSSDMDGYCLH.GQCIYLVDMREKF...CRCEVGYTGLRCEHFFL   11
HB-EGF        KKRDPCLRKYKDYCIH.GECRYLQEFRTPS...CKCLPGYHGHRCHGLTL   12
Amphiregulin  KKKNPCTAKFQNFCIH.GECRYIENLEVVT...CNCHQDYFGERCGEKSM   13
```

Fig. 1c

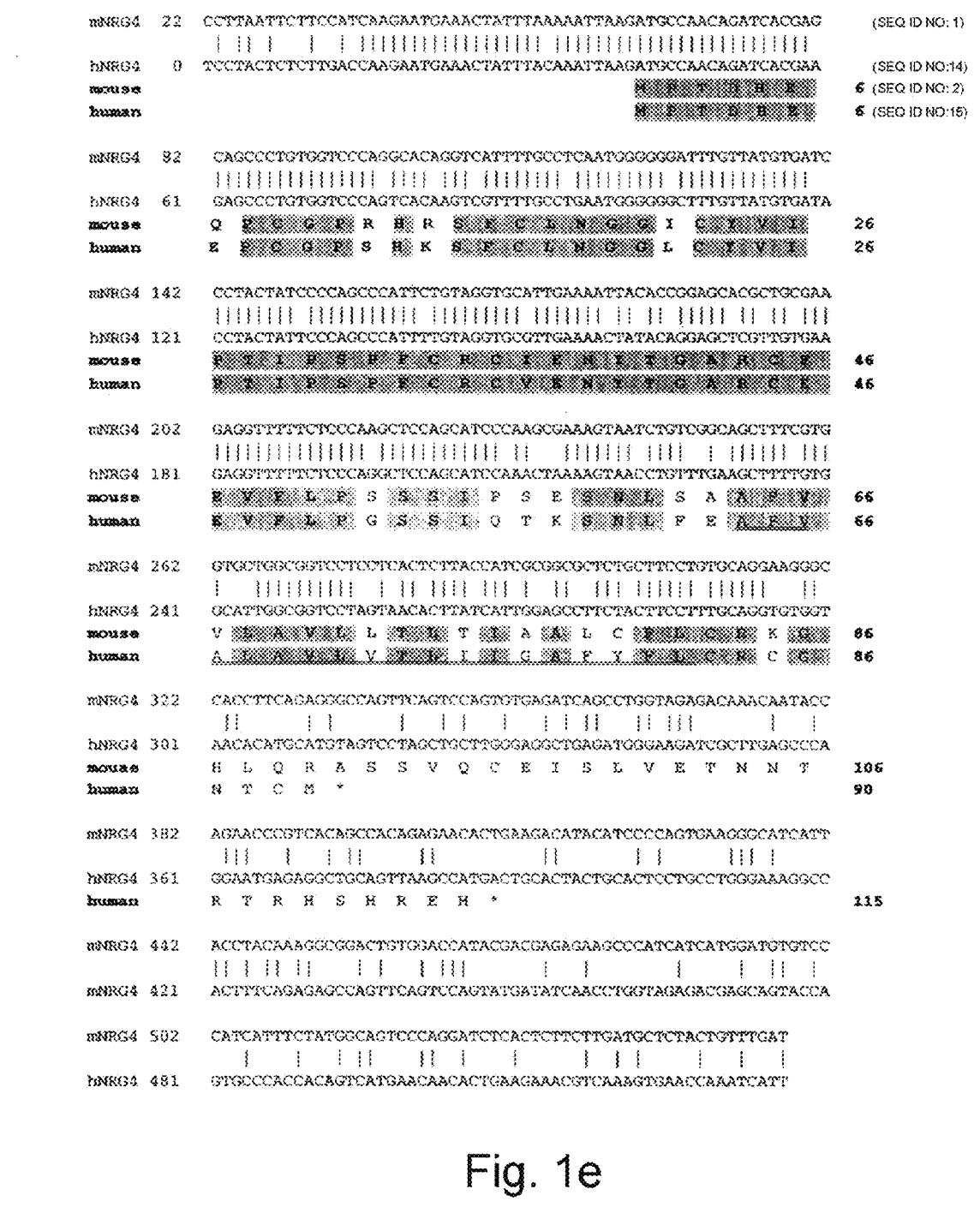

```
mNRG4  22  CCTTAATTCTTCCATCAAGAATGAAACTATTTAAAAATTAAGATGCCAACAGATCACGAG     (SEQ ID NO: 1)
hNRG4   0  TCCTACTCTCTTGACCAAGAATGAAACTATTTACAAATTAAGATGCCAACAGATCACGAA     (SEQ ID NO:14)
mouse                                                    M P T D H E   6 (SEQ ID NO: 2)
human                                                    M P T D H E   6 (SEQ ID NO:15)

mNRG4  82  CAGCCCTGTGGTCCCAGGCACAGGTCATTTTGCCTCAATGGGGGGATTTGTTATGTGATC
hNRG4  61  GAGCCCTGTGGTCCCAGTCACAAGTCGTTTTGCCTGAATGGGGGGCTTTGTTATGTGATA
mouse      Q  P  C  G  P  R  H  R  S  F  C  L  N  G  G  I  C  Y  V  I   26
human      E  P  C  G  P  S  H  K  S  F  C  L  N  G  G  L  C  Y  V  I   26

mNRG4 142  CCTACTATCCCCAGCCCATTCTGTAGGTGCATTGAAAATTACACCGGAGCACGCTGCGAA
hNRG4 121  CCTACTATTCCCAGCCCATTTTGTAGGTGCGTTGAAAACTATACAGGAGCTCGTTGTGAA
mouse      P  T  I  P  S  P  F  C  R  C  I  E  N  Y  T  G  A  R  C  E   46
human      P  T  I  P  S  P  F  C  R  C  V  E  N  Y  T  G  A  R  C  E   46

mNRG4 202  GAGGTTTTTCTCCCAAGCTCCAGCATCCCAAGCGAAAGTAATCTGTCGGCAGCTTTCGTG
hNRG4 181  GAGGTTTTTCTCCCAGGCTCCAGCATCCAAACTAAAAGTAACCTGTTTGAAGCTTTTGTG
mouse      E  V  F  L  P  S  S  S  I  P  S  E  S  N  L  S  A  A  F  V   66
human      E  V  F  L  P  G  S  S  I  Q  T  K  S  N  L  F  E  A  F  V   66

mNRG4 262  GTGCTGGCGGTCCTCCTCACTCTTACCATCGCGGCGCTCTGCTTCCTGTGCAGGAAGGGC
hNRG4 241  GCATTGGCGGTCCTAGTAACACTTATCATTGGAGCCTTCTACTTCCTTTGCAGGTGTGGT
mouse      V  L  A  V  L  L  T  L  T  I  A  A  L  C  F  L  C  R  K  G   86
human      A  L  A  V  L  V  T  L  I  I  G  A  F  Y  F  L  C  R  C  G   86

mNRG4 322  CACCTTCAGAGGGCCAGTTCAGTCCAGTGTGAGATCAGCCTGGTAGAGACAAACAATACC
hNRG4 301  AACACATGCATGTAGTCCTAGCTGCTTGGGAGGCTGAGATGGGAAGATCGCTTGAGCCCA
mouse      H  L  Q  R  A  S  S  V  Q  C  E  I  S  L  V  E  T  N  N  T   106
human      N  T  C  M  *                                                90

mNRG4 382  AGAACCCGTCACAGCCACAGAGAACACTGAAGACATACATCCCCAGTGAAGGGCATCATT
hNRG4 361  GGAATGAGAGGCTGCAGTTAAGCCATGACTGCACTACTGCACTCCTGCCTGGGAAAGGCC
human      R  T  R  H  S  H  R  E  H  *                                 115

mNRG4 442  ACCTACAAAGGCGGACTGTGGACCATACGACGAGAGAAGCCCATCATCATGGATGTGTCC
mNRG4 421  ACTTTCAGAGAGCCAGTTCAGTCCAGTATGATATCAACCTGGTAGAGACGAGCAGTACCA

mNRG4 502  CATCATTTCTATGGCAGTCCCAGGATCTCACTCTTCTTGATGCTCTACTGTTTGAT
hNRG4 481  GTGCCCACCACAGTCATGAACAACACTGAAGAAACGTCAAAGTGAACCAAATCATT
```

Fig. 1e

SEQUENCE LISTING

```
<160> NUMBER OF SEQ ID NOS: 20

<210> SEQ ID NO 1
<211> LENGTH: 750
<212> TYPE: DNA
<213> ORGANISM: Mus musculus

<400> SEQUENCE: 1

tgttgaggtg ctgattttca accttaattc ttccatcaag aatgaaacta tttaaaaatt     60
```

aagatgccaa cagatcacga gcagccctgt ggtcccaggc acaggtcatt ttgcctcaat 120
ggggggattt gttatgtgat ccctactatc cccagcccat tctgtaggtg cattgaaaat 180
tacaccggag cacgctgcga agaggttttt ctcccaagct ccagcatccc aagcgaaagt 240
aatctgtcgg cagctttcgt ggtgctggcg gtcctcctca ctcttaccat cgcggcgctc 300
tgcttcctgt gcaggaaggg ccaccttcag agggccagtt cagtccagtg tgagatcagc 360
ctggtagaga caaacaatac cagaacccgt cacagccaca gagaacactg aagacataca 420
tccccagtga agggcatcat tacctacaaa ggcggactgt ggaccatacg acgagagaag 480
cccatcatca tggatgtgtc ccatcatttc tatggcagtc ccaggatctc actcttcttg 540
atgctctact gtttgattgt tcatcgttca catacagaaa tgacgctggt ttcctgtgtt 600
gaccttgcac cctgctactg tcatcactgg cctggaagtc agcagtatag ataaggctgg 660
ccctgaattc aagagactca cctgtttttg cctactcaga gttactggaa ttaaaggcat 720
aacaacaaaa aaaaaaaaaa aaaaaaaaga 750

<210> SEQ ID NO 2
<211> LENGTH: 115
<212> TYPE: PRT
<213> ORGANISM: Mus musculus

<400> SEQUENCE: 2

Met Pro Thr Asp His Glu Gln Pro Cys Gly Pro Arg His Arg Ser Phe
1 5 10 15

Cys Leu Asn Gly Gly Ile Cys Tyr Val Ile Pro Thr Ile Pro Ser Pro
20 25 30

Phe Cys Arg Cys Ile Glu Asn Tyr Thr Gly Ala Arg Cys Glu Glu Val
35 40 45

Phe Leu Pro Ser Ser Ser Ile Pro Ser Glu Ser Asn Leu Ser Ala Ala
50 55 60

Phe Val Val Leu Ala Val Leu Leu Thr Leu Thr Ile Ala Ala Leu Cys
65 70 75 80

Phe Leu Cys Arg Lys Gly His Leu Gln Arg Ala Ser Ser Val Gln Cys
85 90 95

Glu Ile Ser Leu Val Glu Thr Asn Asn Thr Arg Thr Arg His Ser His
100 105 110

Arg Glu His
115

<210> SEQ ID NO 3
<211> LENGTH: 47
<212> TYPE: PRT
<213> ORGANISM: Mus musculus

<400> SEQUENCE: 3

Asp His Glu Gln Pro Cys Gly Pro Arg His Arg Ser Phe Cys Leu Asn
1 5 10 15

Gly Gly Ile Cys Tyr Val Ile Pro Thr Ile Pro Ser Pro Phe Cys Arg
20 25 30

Cys Ile Glu Asn Tyr Thr Gly Ala Arg Cys Glu Glu Val Phe Leu
35 40 45

<210> SEQ ID NO 4
<211> LENGTH: 49
<212> TYPE: PRT
<213> ORGANISM: Rattus norvegicus

<400> SEQUENCE: 4

```
Ser His Leu Ile Lys Cys Ala Glu Lys Glu Lys Thr Phe Cys Val Asn
1               5                   10                  15

Gly Gly Glu Cys Phe Thr Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val


<210> SEQ ID NO 5
<211> LENGTH: 46
<212> TYPE: PRT
<213> ORGANISM: Mus musculus

<400> SEQUENCE: 5

Gly His Ala Arg Lys Cys Asn Glu Thr Ala Lys Ser Tyr Cys Val Asn
1               5                   10                  15

Gly Gly Val Cys Tyr Tyr Ile Glu Gly Ile Asn Gln Leu Ser Cys Lys
            20                  25                  30

Cys Pro Val Gly Tyr Thr Gly Asp Arg Cys Gln Gln Phe Ala
        35                  40                  45


<210> SEQ ID NO 6
<211> LENGTH: 48
<212> TYPE: PRT
<213> ORGANISM: Mus musculus

<400> SEQUENCE: 6

Glu His Phe Lys Pro Cys Arg Asp Lys Asp Leu Ala Tyr Cys Leu Asn
1               5                   10                  15

Asp Gly Glu Cys Phe Val Ile Glu Thr Leu Thr Gly Ser His Lys His
            20                  25                  30

Cys Arg Cys Lys Glu Gly Tyr Gln Gly Val Arg Cys Asp Gln Phe Leu
        35                  40                  45


<210> SEQ ID NO 7
<211> LENGTH: 47
<212> TYPE: PRT
<213> ORGANISM: Mus musculus

<400> SEQUENCE: 7

Asn Ser Tyr Pro Gly Cys Pro Ser Ser Tyr Asp Gly Tyr Cys Leu Asn
1               5                   10                  15

Gly Gly Val Cys Met His Ile Glu Ser Leu Asp Ser Tyr Thr Cys Asn
            20                  25                  30

Cys Val Ile Gly Tyr Ser Gly Asp Arg Cys Gln Thr Arg Asp Leu
        35                  40                  45


<210> SEQ ID NO 8
<211> LENGTH: 47
<212> TYPE: PRT
<213> ORGANISM: Homo sapiens

<400> SEQUENCE: 8

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu
        35                  40                  45
```

```
<210> SEQ ID NO 9
<211> LENGTH: 46
<212> TYPE: PRT
<213> ORGANISM: Mus musculus

<400> SEQUENCE: 9

Ser His Phe Asn Lys Cys Pro Asp Ser Glu Thr Gln Tyr Cys Phe His
1               5                   10                  15

Gly Thr Cys Arg Phe Leu Val Gln Glu Glu Lys Pro Ala Cys Val Cys
            20                  25                  30

His Ser Gly Tyr Val Gly Val Arg Cys Glu His Ala Asp Leu
        35                  40                  45


<210> SEQ ID NO 10
<211> LENGTH: 46
<212> TYPE: PRT
<213> ORGANISM: Mus musculus

<400> SEQUENCE: 10

Thr His Phe Ser Arg Cys Pro Lys Gln Tyr Lys His Tyr Cys Ile His
1               5                   10                  15

Gly Arg Cys Arg Phe Val Val Asp Glu Gln Thr Pro Ser Cys Ile Cys
            20                  25                  30

Glu Lys Gly Tyr Phe Gly Ala Arg Cys Glu Arg Val Asp Leu
        35                  40                  45


<210> SEQ ID NO 11
<211> LENGTH: 46
<212> TYPE: PRT
<213> ORGANISM: Mus musculus

<400> SEQUENCE: 11

Val Gln Ile Tyr Lys Cys Ser Ser Asp Met Asp Gly Tyr Cys Leu His
1               5                   10                  15

Gly Gln Cys Ile Tyr Leu Val Asp Met Arg Glu Lys Phe Cys Arg Cys
            20                  25                  30

Glu Val Gly Tyr Thr Gly Leu Arg Cys Glu His Phe Phe Leu
        35                  40                  45


<210> SEQ ID NO 12
<211> LENGTH: 46
<212> TYPE: PRT
<213> ORGANISM: Mus musculus

<400> SEQUENCE: 12

Lys Lys Arg Asp Pro Cys Leu Arg Lys Tyr Lys Asp Tyr Cys Ile His
1               5                   10                  15

Gly Glu Cys Arg Tyr Leu Gln Glu Phe Arg Thr Pro Ser Cys Lys Cys
            20                  25                  30

Leu Pro Gly Tyr His Gly His Arg Cys His Gly Leu Thr Leu
        35                  40                  45


<210> SEQ ID NO 13
<211> LENGTH: 46
<212> TYPE: PRT
<213> ORGANISM: Mus musculus

<400> SEQUENCE: 13

Lys Lys Lys Asn Pro Cys Thr Ala Lys Phe Gln Asn Phe Cys Ile His
1               5                   10                  15

Gly Glu Cys Arg Tyr Ile Glu Asn Leu Glu Val Val Thr Cys Asn Cys
```

```
            20                  25                  30

His Gln Asp Tyr Phe Gly Glu Arg Cys Gly Glu Lys Ser Met
        35                  40                  45


<210> SEQ ID NO 14
<211> LENGTH: 536
<212> TYPE: DNA
<213> ORGANISM: Homo sapiens

<400> SEQUENCE: 14

tcctactctc ttgaccaaga atgaaactat ttacaaatta agatgccaac agatcacgaa      60

gagccctgtg gtcccagtca caagtcgttt tgcctgaatg gggggctttg ttatgtgata     120

cctactattc ccagcccatt ttgtaggtgc gttgaaaact atacaggagc tcgttgtgaa     180

gaggtttttc tcccaggctc cagcatccaa actaaaagta acctgtttga agcttttgtg     240

gcattggcgg tcctagtaac acttatcatt ggagccttct acttcctttg caggtgtggt     300

aacacatgca tgtagtccta gctgcttggg aggctgagat gggaagatcg cttgagccca     360

ggaatgagag gctgcagtta agccatgact gcactactgc actcctgcct gggaaaggcc     420

actttcagag agccagttca gtccagtatg atatcaacct ggtagagacg agcagtacca     480

gtgcccacca cagtcatgaa caacactgaa gaaacgtcaa agtgaaccaa atcatt         536


<210> SEQ ID NO 15
<211> LENGTH: 90
<212> TYPE: PRT
<213> ORGANISM: Homo sapiens

<400> SEQUENCE: 15

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Cys Gly Asn Thr Cys Met
                85                  90


<210> SEQ ID NO 16
<211> LENGTH: 26
<212> TYPE: DNA
<213> ORGANISM: Artificial
<220> FEATURE:
<223> OTHER INFORMATION: synthetic oligonucleotide

<400> SEQUENCE: 16

cctactctct tgaccaagaa tgaaac                                            26


<210> SEQ ID NO 17
<211> LENGTH: 22
<212> TYPE: DNA
<213> ORGANISM: Artificial
<220> FEATURE:
<223> OTHER INFORMATION: synthetic oligonucleotide

<400> SEQUENCE: 17

aatgatttgg ttcactttga cg                                                22
```

<210> SEQ ID NO 18
<211> LENGTH: 40
<212> TYPE: PRT
<213> ORGANISM: Unknown
<220> FEATURE:
<223> OTHER INFORMATION: motif conserved in most mamalian ErbB-ligand isoforms
<220> FEATURE:
<221> NAME/KEY: misc_feature
<222> LOCATION: (2)..(8)
<223> OTHER INFORMATION: any amino acid
<220> FEATURE:
<221> NAME/KEY: misc_feature
<222> LOCATION: (10)..()
<223> OTHER INFORMATION: any amino acid
<220> FEATURE:
<221> NAME/KEY: misc_feature
<222> LOCATION: (14)..()
<223> OTHER INFORMATION: any amino acid
<220> FEATURE:
<221> NAME/KEY: misc_feature
<222> LOCATION: (16)..(28)
<223> OTHER INFORMATION: any amino acid
<220> FEATURE:
<221> NAME/KEY: misc_feature
<222> LOCATION: (30)..()
<223> OTHER INFORMATION: any amino acid
<220> FEATURE:
<221> NAME/KEY: misc_feature
<222> LOCATION: (32)..(34)
<223> OTHER INFORMATION: any amino acid
<220> FEATURE:
<221> NAME/KEY: misc_feature
<222> LOCATION: (36)..()
<223> OTHER INFORMATION: any amino acid
<220> FEATURE:
<221> NAME/KEY: misc_feature
<222> LOCATION: (38)..()
<223> OTHER INFORMATION: any amino acid

<400> SEQUENCE: 18

```
Cys Xaa Xaa Xaa Xaa Xaa Xaa Xaa Cys Xaa Asn Gly Gly Xaa Cys Xaa
1               5                   10                  15

Xaa Xaa Xaa Xaa Xaa Xaa Xaa Xaa Xaa Xaa Xaa Xaa Cys Xaa Cys Xaa
            20                  25                  30

Xaa Xaa Tyr Xaa Gly Xaa Arg Cys
        35                  40
```

<210> SEQ ID NO 19
<211> LENGTH: 23872
<212> TYPE: DNA
<213> ORGANISM: Homo sapiens
<220> FEATURE:
<221> NAME/KEY: misc_feature
<222> LOCATION: (22570)..()
<223> OTHER INFORMATION: any nucleotide
<220> FEATURE:
<221> NAME/KEY: misc_feature
<222> LOCATION: (23034)..()
<223> OTHER INFORMATION: any nucleotide

<400> SEQUENCE: 19

```
ggggttaggg agtgggtctg tgtagttgtg gggcgggtga tgtggcgggc gaaggggggc      60

caggggcccg agtgagctat cgggcgaaat aacggcattg tggtgtaaga tgcatggccc     120

taagagctat gcctgaggga attaaattgt agcaacatgt gaaagtgctc gggatagtgt     180

cttaccctgc tcagctatac tgtggggtac ctcctaagta tgtctgtaat tatctgtctc     240

gtggtcctaa ttcctgtgct ttatttcttc actattatta aaacagcctc caaactgctt     300

tctctgatac catttcctca gcagattcca atttgtttcc cacactgcca tcagaatgaa     360
```

```
ttttctaaaa tgttgatgta atcatgtcac tcccttgcta aaaagctttc aaagcttccc    420
attgccttta agataaagtc tacaatctgg atccagcatg ttttatacta tctattcttg    480
ccattctttt ccccaccatc ccgccctcct acaaacatac acactccaca ctcaccactg    540
cacatttcct ggcttgtgat ccacctgcaa ttatttgaat acattagatc ttccttcttt    600
tatacctta gacatgctgt tacctctgtc tgaaatgctc attcatctct gtttacaaac    660
tcttattcat tctacctctt ggaatctttt tctgattctc cataacagtt aagcattgtg    720
tgtgtgtgtg tgtgtgtgtg tgtaaaaata ttgacataca tatgtgtctg tgaaaatatt    780
aggtttaatc acatgaaact gtcatttgta taagtcaaaa tatgctttat atgaatcagc    840
ctaaaacatt tttgtgcttg tttttgtgtc tggcattcct catccagcaa gagactgtcc    900
tctttttttt aaaaggatgg caggccactt agtacacgtt tattgatacg tggatggaaa    960
aatagttttt aaagatcaag gctttcattt agagcagggg tccccacacc cgggccacag   1020
accagtacca gactgtggcc tattaggaac caggccacac agcaggtgag cagcaggcaa   1080
gcaagcctca tggcctgtgc tccgcctcct atcaaatcag cggtcgcatt agattctcat   1140
agagcatgga ccctattgtg aactgcacat gtgagggatc cagattgcgt gctctttatg   1200
ggaatctaat gccagatgac ctgaggtaga ataatttcaa cctgaaacca tccaccaccc   1260
cagtccatgg aaaaattgtc ttccatgaaa ccggtccctg gtgccaaaaa gattggggac   1320
cactgactta gtgaaaagtt agcttgaaaa tctataggtt ttctactttg gaatcacatg   1380
gtcctaaagg ttgcttattt gcatggtgca aaaaataaca caaaatcatc acaatatgtc   1440
tcttaataaa tacatctcaa atgtcatgaa gtcacagatt atctcccata tacagtttag   1500
tagtcatttt cataatagta gacagcatca tggcttcaag gttcaaataa aataataaaa   1560
gatactgatt ttgtttcatg aaaacatttt gaaattcaaa caccatacac taaaatggtt   1620
tagtgtgtgt gtatgtgtag aagcacacct ctgagatatt gtaggttttg gtttcagact   1680
gctgcaataa agcaaatatc acaataaagt gagtcacaca aattttttgg tttcccaatg   1740
catataaaag gtatgtttat actatagcct attaggtatg cagtagcatt atgtctaaaa   1800
aataatgtat atcccttaat ttaaaaatac tttattgtta aaaaatgctg acaaacatct   1860
gagccctcag tgagttgtaa tgtttttgct gggggagggt cttgcctcaa cagtggactt   1920
aagatattta gtcaaccatg ctgtaaacag atgtgctgtc atcaaggctt tgttgttctg   1980
tttatacagc acaggcagag tagatttagc ataattctta agggccctag gattttcaga   2040
atgatggatg agtgttggct tcagcttaaa gtcacaagct atattagcct ataacaagaa   2100
gtcaacctgt ccttcgaagc ttagaagcca gacattgact tctctttagc tataaaagtt   2160
caagatggta tcttctacta gaaggttgtt ctacagtgaa aatctgttta gtgtaaccat   2220
cttcaatgat cttagataga ttttctggat aatttgctgc agcttctaca ttagcgcttg   2280
ttgstktrys tgwgtcacty wyakgwtmts gagatggttt ctttccttam acctcatgaa   2340
ccaacctctg ctagcttcaa acttttcttc tgctgcttct ttacctctct cggccttcat   2400
agaatttata agaattaggg ccttgctctg gattaggctt tggcttacag caagcttgtc   2460
caaccctggc gcgtgggccg catgcagccc agaatggctt tgaatgccac acaacacaaa   2520
ttcataaact tcttaaaaca ttataagatt tttttgtgat ttttttttct catcagctat   2580
tgttagtgtt agtgtatttt atgtgtggcc caagacaatt atttttccac tgtggcccag   2640
ggaagtcaaa agattggaca tccctggctt agaggaagtg gtggctggtt tgaccttcta   2700
tccagatcac taaaactttc tccataaaag caataaggct gtttcatttt atcatttgtg   2760
```

```
tgttcactga atagcacttt taatttcctt taacagtgca agaggcctat cttacctttc   2820
tgcatgcctt cctcactaaa cttaatcatt ttagcttttg ctttaaagtg agaaagatgc   2880
agctctccct tttacttgaa cacttagggg ccattgtagg gttatcaatt gggctaattt   2940
caatattgtt gtgtctcagg gaatagagag gccagaggag ataggggaac ggtcggtcaa   3000
tggagcattc agaatatgca gatttakcga ttaagttctc tatcttacac agtcatggtt   3060
catggtgcsc caaaacaatt acaatagtaa catcaaagat cactgatcrc agatcaccat   3120
aaccgataga ataataatga aaaagttcga aatattgcaa ggattaccaa aatgtgacac   3180
agaaacgtga agtgagcaca ggctgttgga aaaatggcac caacagacac agggttgcca   3240
caagcctkta gyaaaaacaa tatctgcaaa gtscaawaaa atgcataaaa tgagatatgt   3300
ctgtataatg gttatagcta tgtaaaaatt gcctttgaat gtgggagata atatgtaata   3360
atgggtggct ggcaagatgg ccgaatagga acagctctgg tctgcagctc ccagcgagat   3420
caacacagaa ggcgggtgat ttctgcattt ctggctgagg aacctggctt atctcattgg   3480
gatgggttag acagtgggtg cagcccacag agggcaagcc aaagcagggt ggggtgtcgc   3540
ctcaccgggg aagtgcaagg gattggggaa ctacccccct agccaaggga agccatgagg   3600
gacggtgcac tccagcccag atactatgct attcccatgg tcttcacaac ccacagatga   3660
ggaaattccc tcacgtgcct acgccatcag ggccctgagt ttcaagcaca aaactgagta   3720
gctgtttggg cagacaccaa actgggtggc tgtttgggca gacaccgagc tagctgcagg   3780
agcttttttt catacccaa tggtgcctgg aacaccagcg agacagaacc gttcaccccc   3840
ctggaaaggg grctgaagcc agggagccaa gctgtctagc tcagcagatc ccaccccccac   3900
ggagcccagc aagctaaaat ccactggctt gaaattctcg ctgccagcac agcagtctga   3960
agtcgacctg ggatgcttga gcttggtgga gggagggatg cttgccatta ctgaggcttg   4020
agtaggtgtt tttcccctca cagtgtaaac aaagccgcct ggaagttcga actaggtgga   4080
gcccaccgca gctcagcaaa gccactgtag acagactgcc tctctagatt tcttctctct   4140
gggcagggga atctctaaaa aaaaaaaggc agcagcccca gtcagrgggt tatggataaa   4200
acccccatct ccctggaaca gaggacctgg gggaaggggt ggctgtgggc acagcttcgg   4260
cacacttaaa catccctgcc tgccagctct gaagagagca gtggatctct aagcacagca   4320
tccgagctct gctaagggag gactgcctcc tcaagtgagt ccctaacccc tgtgtctcct   4380
gacggggaga cacctcccag taggggtcaa cagacacctc atacaggaga gctccagccg   4440
gcatctggcg gatgcccctc tgkgacaaag cttccagagg aagaaacagg cagcaatctt   4500
tactgttctg cagcctccgc tggtgatacc cagacaaaca gggtctggag tgaacctcca   4560
gcaaactcca gcagacctgc agcagagagg cttgactgtt agatggaaaa ttaacaaaca   4620
gaaaggaatc gcatcaacat cmacaaaaag gatgtccact tagaaacccc atccgaaggt   4680
cacaacatca aaggccaaag gtagatacat ccacgaagat gaggaaaaac cagcacaaaa   4740
aggctgaaaa ttccaaaacc cagaacgcct cttctactcc aaaggatcac actcctcgcc   4800
agcaagggaa caaaactgga tggagaatga gtttgacaaa tcgacagaat taggcttcag   4860
aaggtgggta ataacaaact cctccaagct aaaggaggat attctaactc aatgcaagga   4920
agctaagaac catgaaaaaa ggttagagga attactaact ggaataagca gtttagagaa   4980
gaacataagt gacctgattg agctgaaaaa catagcacga gaacttcaac aagcatacac   5040
aagtatcaat agccaaatcg atcaagtgga agaaaggata tcagagattg aagatcaact   5100
taatgaaata aagtgtgaag acaagattag agaaaaaaga ttgaaaagaa acaaacgagc   5160
```

```
ctccaagaaa tatgggacta tgtgaaaaga ccaaacctac atttgattgg tgtacctaaa   5220
agtgaaaggg agaatgaaac caagttggaa aacactcttc aggatattat ccagtagaac   5280
ttccccaacc tagcaagaca ggccaacatt aaaattcagg aaataccgag aacaccacaa   5340
agatactact cgagaagagc aaccccaaga cacataattg tcagattcac caaggttgaa   5400
atgaaggaaa aaatgttaag agcagccaga aaagtcaggt taccaacaaa ggaaagctca   5460
tcagattagc agcagatctc tctgcagaaa cactacacac cagaagagag tgggggccaa   5520
tattcaacat tcttaaaaga attttcaacc cagaatttca tatccagcaa aactaagctt   5580
cattagtgaa ggagaaataa aatcctttac agacaagcaa atgctgagag attttgtcac   5640
caccaggcct gctttacaag agcccctgaa ggaagcacta aacatggaaa ggaaaaactg   5700
gtacagccac tgcaaaaaca aattgtaaag accatcgaca ctatgaagaa actgcatcaa   5760
ctaaggggca aaacaactag ctagcatcat aatgatagga tcaaattcac acataacaat   5820
attaatcttc aatgtaaaca ggctaaatgc cccaattaaa agacacagac tggcaaactg   5880
gataaagatt caagacccat tggcgtgctg tgtttaggag acccatctta tatgcaaaga   5940
aacacacgct caaaataaag ggctggagga atatttacca agcaaatgga aagcaaaaaa   6000
aaaaaaaaaa aaaaaaggca ggggttgcaa tcctagtctc tgataaaaac agactttaaa   6060
ccaacaaaga tcaaaagaaa caaagaaggg cattacataa tggtaaaggg atcaatgcag   6120
aaagaagaga taactatcct aaatatatat gcacccaata caggagcacc cagatccata   6180
aagcaagttc ttagagacct acaaagagac atagactccc acacaataat agtgggaaac   6240
tttaacaccc cactgttcat attagatcaa caagaaagaa aattaaggat attcaggact   6300
tgaactcagc tctggaccaa gtggacctaa tagacatctg cagaactctc cacccaaatc   6360
aacagaatat atattcttct cggcaccaca ttgcaattat cctaaaattg accacataat   6420
tggaagtaaa atactcctca gcaaatgcaa aataatggaa atcataacag tctctccaac   6480
cacagtgcaa tcaaattaga actcaggatt aagaaactca ctcaaaactg cacaagtaca   6540
tggaaactga acaacctgct cttgagtgac tgatgggtaa ataacgaaat taaggcagaa   6600
ataaagaagt tctttgaaac caataagaac aaagaaacaa tgtaccagaa tctctgggac   6660
acagctaaag cagtgtttag agggaaattt atagcactaa atgccctcaa gagaaagcag   6720
gaaagatcta aaattgacac cctaacatca caattaaaag aactagagga gcaagagcaa   6780
acaaattcaa aatctagcag aagacaagaa ataactaaga tcagagcagt ctgaaggaga   6840
tagagacacg aaaaacactt caaaaaatca atggtatcca ggagttggtt tttttgaaaa   6900
gatcaataaa atagactgct agactaataa agaagaaaag aaagaatcaa atagacacaa   6960
taaaaaatga taaaggggat attaccactg atcccacaga aatataaact accatcagag   7020
aataccataa acacctctat gcaaataaac tagaaaatct agaagaaatg gataaattcc   7080
tggacacata ccccctccca acactaaacc aggaagaagt cgaatccctg aatagaccaa   7140
taacaagttc tgaaattgag gcagtaatta atagcctacc aaccaaaaaa agtccaggac   7200
aagacagatt cacagccaaa ttccaccaga ggtaccaaga ggacctggta ccattccttt   7260
tgaaactatt ccaaacaata gaaaaagagg gactcctccc taactcattt tatgaggcca   7320
gcatcatcct gataccaaag cctggcagag atacaacaag aaaacaaaac ttcaggccaa   7380
yatccctgat gaatatcgat gtgaaaatat tcaataaaat attggcaaac tgaatccaac   7440
agcatgtcaa aaagcttatc caccacgatc aagtcagctt catccctgga atgcaaggat   7500
gattcaacat acagaaatca atacccgtaa tccatcacat aaacagaacc aatgacaaaa   7560
```

```
accacgtgag tatctcaata gatgcagaaa aggcctttga taaaagtcaa yaccccttta   7620
tgctaaaaac taaaaacaat aaactaggta tcgatggaat gcatgtcaaa aatmataaga   7680
gctatttatg acaaacccac agccaatatc atactgaatg ggcaaaagct ggaagcattc   7740
cctttgaaaa ccagcacaac acaaggatgc cctctctcac cattcctatt caacatagta   7800
ttggaggttc tggccaggcc aatcaggcaa gagaaagaaa taaaggttat tcaaatagga   7860
agagaggaag tcaaattgtc tctgtttgca gatgacatga ttgtatattt agaaaacccc   7920
atcatctcag ccccaaaact ccttaagctg atagcaactt cagcaaagtc tcaggataca   7980
aaatcagtrt gcaaaaatca caagcattcc tatacaccaa taacagacaa agagagccaa   8040
atcatgagtg aactcccatt cacaactgct actaagagaa taaaatacct aggaatacaa   8100
ctcacaaggg atgtgaagga cctcttcaag gagaactaca aaccactgct cagggaaata   8160
agagaggaca caaacaaatg gaagaacatt ccatgctcat ggataggaag aatcaatatc   8220
ttgaaaatgg ctatactgcc caaagtaatt tagagattca atgccatccc catcaggcta   8280
ccattgactt tcttcacaga attagaaaaa tctactttaa actttatgtg gaaccaaaaa   8340
agagcctgtg tagccaagac aatcctaacc aaaaggaaca aagctggagg catcacgcta   8400
cctgacttca aactatacta caagactaca gtaaccaaaa cagcatggta ctggtatcaa   8460
aacagacata tagaccaatg gaacagaaca gaggcctcag aaataactcc acccatctac   8520
aaccatctga tctttgacaa acctgacaaa aacaagcaat ggggaaagga tttcctattt   8580
aataaatggt gttgggaaaa ttggatagcc atatgcagaa aactgaaact ggaccccttc   8640
cttacacctc atataaaaat taattcaaga tggattaaag acatacacct aaaacgtaaa   8700
gccataaaaa ccctagaaag aaacctaggc aataccattc aggacacaga tatgggcaaa   8760
gacttcgtga ctaaaacacc aaaagcaatg gcaacaaaag ccaaaactga caaatgggat   8820
ctaattaaac caaagagctt ctgcacagca aaagaaactc tcgtcagagt aaacaggcaa   8880
cctacagaat gggagaaaat ttttgcaatc tattcatctg agaaagggct aatatccaga   8940
atctacaagg aacttaaaca aatttacaag aaaaaaacca acaaccccat caaaaagtga   9000
gtgaaggata tgaacagaca gtcttcaaaa taagacattt atgtggccaa caaacgtatg   9060
aaaaaaagct catcatcact ggtcattaga gaaatgcaaa tcaaaaagca caatgagata   9120
ccatctcatg ccagttagaa tggcgatcat taaaaagtca ggaaacaaca gtgctggaga   9180
ggatgtgaag aaataagaat gcttttacac tattggtggg agtgtaaatt agttcaacca   9240
ttgtggaaga cagtgtggtg attccccaag gatctagaac tagaaatacc atttgaccca   9300
gcaatccaat tactgggtat atacccaaag gattataaat catgctacta taaagacaca   9360
tgcacacata tgtttattgc ggcactgttc acaatagcaa agacttggaa ccaacccaaa   9420
ttcccctcaa tgatagactg gataaagaaa atgtggcaca tatataccgt ggaatactat   9480
gcagccataa gaaaggatga gctcatgtcc tttgcagggc catggatgaa gctggaaacc   9540
atcattctca gcaaactaac acaagaacag aaaaccaaac accgcatgtt ctcataggtg   9600
gaaattgaac aatgagaata catggacaca gggaggagaa catcacacac tagggcctgt   9660
cggggtgggg ggctaaggga gggataacat taggagaaat acctaatgta aatgacaggt   9720
tggtgggtgc aggaaaccag catggcactt gtatacctat gtaacaaacc tgcatattct   9780
gcacatgtat cccagaactt aaagtataat tttaaaaatg taataatgaa catttttttt   9840
tttttgagac ggagtctcac tctgttgccc aggctggagt gcagtggtgc aatctcagct   9900
cactgcaagc tccgcctccc gggttcacac cattctccta atgaacagat tgtttttaga   9960
```

```
gtatttgatt ttgagtttat tttaatattt tcttaaaaca acaaaacaaa cttattagtt  10020
tgggctttac atcagtcaag taataatgtc tgaattgtcg ttttagaaaa gataaccatc  10080
taaatgtttg gcatatttta gataattata tgatgaagaa ctctatattc atttaaacaa  10140
aattacagtt ttagtcaata ttttaaaatt gtttatgatt tttaaaactt aactttcctc  10200
actgtatatt taacaacttt gccatagcat tcaggcatta cactgtcatw ggtattagtc  10260
aagttcagtg attttattca tttcaaattg aacttggtgt tacaagtttt attatagcta  10320
ttaccttctt ttagctttat aagttcttca ggtcattatt tatataaatt ttatctggct  10380
tgtaaggtaa cacaaacctc ataaaacata aatttaaaaa aatgtttttt taatttgtga  10440
aacacttatc tattagctcc acattaaaat ttcttttctc ccaaacttac actacgtctt  10500
gaattattca gacaagcaaa gataagtaag gagtctaagg aatgtggttt ggtttttacc  10560
tttaaaacgt ggacagtaat ttggaagtgc agcttagttc aactcctttt ctaaataaaa  10620
ttctgctcca tttgcaactc tgaacacgta aattgaaggg gtggctcccg tggccagtgc  10680
ctgacctctg tgcacacctt ggtctggcgt gacctcgccc acactgcaca ctgcagccat  10740
ataaatcaga tttttgacat gttataaaat gcaagtcaca gctgctgttg tctgcggtat  10800
tcaaaaactt ttgaaacact gcatgtccaa caaaatttat tttttgtgtg aatgtaagtt  10860
tttattgagg gtaagtcctg tttgtttgga aaaaagaaac agtatgagtc agtgcttttt  10920
aaaaatcaaa tagatttaat gttctccttc ctgcctgttc tcgctcgtgt gtgtttctct  10980
cgattgcttg ctcgctttct ctgcctctct gcttgtctaa gaaagagctg ttggctttga  11040
gagaagacct tggtattaca actgtgttag tagattgaga tttctgttag agtctttctg  11100
tttaggtcag aagtgttctt tatagaacag aactgggagc ttgtaatcat aatgtaagta  11160
taaatgcttc acctcttcaa atatatgttt gaattctttt gtttctgtta tagcaggaaa  11220
cttcatatgt aagaatgtct tattagctac attgctttgc cagatgccag acatttttgt  11280
gtgtgtgtgg ggttaacatt ttttttcttt tttaaattta attttaagtt ccgggataga  11340
tgtgcaggac gtgcaggttt gttacatagt gtgtttataa catgtgtgcc atggtggttt  11400
gccgcaccta tcagccctgg acattttttta gaagaaaggt ttgcataggt tggtaaatgt  11460
aatgtgcaat ctatggtaaa cttaaaagtg cttttataaa agttttaaag gttcagttca  11520
ttcagtttta cttactgtct catcgttcat gtaaaattcc atgtagtact ctactatgtt  11580
aacaatgttt acgaaaaaaa gccttattag acttttctgc agagagatat ttaagattaa  11640
attacattat ttaggcaatg atttatatta agtacgttat tgatctttta gttttgttca  11700
tattttttac tgaaatgcaa taggtatcta aaaatgctgt aactaaaatt tgtccctagt  11760
atataaatgt ctttattatt ttattttcaa catttaagaa tattgctatt agaatatttg  11820
acattttata atgcccttaa aagaagacta ttttccctga attattactt tttaaaccgt  11880
tttaggtact gtttttcaac cctactctct tgaccaagaa tgaaactatt tacaaattaa  11940
gatgccaaca ggtaatttct tatatattta tatgtttttg tcaatatgtg tccatagcaa  12000
tagaacaaca atcaaaaatg tatattaaca caaggctgta ttattccctt ccaacatcat  12060
tggaagagat gtgaatatga aattaatatt tcaaatatga aatatttggt tttgagagac  12120
cttcctttgt gacataaagc tattttattt tagatatatg tgttttattg gttttataac  12180
ctgataaatt ctagcttgtc ctatatctga aatcagctca aataataagg aaatagaagt  12240
cagaataaaa gtagattcag aaataatgat tcaggttaga tgagttttct ttattgataa  12300
aataaatgcc aagtgttgag atatgtctga ctataatcca attaaaacaa ggacactaat  12360
```

cttagctgtg ataaagttac attccaccct cagtggaaaa ccatatatga tgacgccttt 12420
gatgctgatg taatgttaat tttatttttt agccaaatta ttcctgaaaa attttataat 12480
cttgttgaaa gttgtttgat tacgaagaag catggcattg tgtaaaaaag aaaaaaatct 12540
aaaagcattc attttggttg attttacttt ctttttcacc agttctctgt agttctgatt 12600
tcgtctttac atttttatac tcttagggct ataatgtgat gctgaaacag gatttctca 12660 attctaaagt agaacaaaag ttttaaaatt tgaaattctg attgtggaga tatctgactc 12720
atagcaatta tatcttagca agtattgata tcttagtggc acataaatgc tagataattt 12780
ttaaaattaa tatactaatt ttaatgtcaa attggagtcc cagtgggaga gtaatgccat 12840
tttcttattc tgattagatg attctgggtc atttcctaga cagaaacaat taggaactaa 12900
caatgtacaa gtttaaagca atgtaatttc ccctttaags ctggaagata agatattcac 12960
caattttctc ttcataaatt actagtataa tgactcaatg aatccttctg ttattctaat 13020
tttttctata caatggcttt ggtggacagg gattttttat aaaaggtctt gggggtgagg 13080
ctagaaggaa ggagaggtac caagggagaa agggaaggca gagagagaaa gatagataaa 13140
ggaaaggtca taaagaagga agatgaggct gaggaaagag gaaagagaga aaagaagtca 13200
gagagaagta gaggtttatt ttcttaatat tctgaaagat ttggctgtat atcaagctat 13260
gacttagctt tttaattttt ctttgcaact ttagatatgc cttatggtta gtaactgtta 13320
cctaaaacac tttgcaaatc aacaccttat aagtttattt ttggtttctg acatttagat 13380
tgtcatatag gaacatttaa agttaacttt ggaaataaaa agttaattat ctaaatcctt 13440
taccagctgc aatttcagat attaatgtat ttgagaccta atagggaaaa caagaattta 13500
aataaattct tgggacagrg aaatgctagg taatactgcc aaatctctgt agtaagtgag 13560
aaaggccctg tttgttctaa gatgctgatc acctcctttt aatctaacta atatagatat 13620
tccttatttc tgttatataa tgtctaaacc cattatagtt aatggccata tctttaggac 13680 ataattttc tctcaaagac atagaagtcc cagtctgtca aataaggaat agaattaaat 13740
ctttcatttt gagaaaaaaa attcttcatt ctgattttca gaattgctac ttcagtttaa 13800
gatagttatt cctattcctt gttgcattag gaaaacttta atttgctttt ctctatttta 13860
tatatgtatg tgttctagat cacgaagagc cctgtggtcc cagtcacaag tcgttttgcc 13920
tgaatggggg gctttgttat gtgataccta ctattcccag cccattttgt aggtgagtga 13980
aatggactag gggagatgt taactttatt ttttattgtc tactaacttc tttgagaagt 14040
gataaaaagt aaacaaaaag tgtaagatga aaagatgtga ggcatattca tatttattta 14100
gggaaaatta tccttttaaa acaaaacaaa aacaaaataa aatagcacat aaaaatctca 14160
ctaatcaagg tgtttattct gaaaattgct aatggtagtt cctagcctag acacattttt 14220
aaaaaataat cccttttagt gaactctttg attttagcaa tttaaggaag gcagtctatg 14280
cttaatatta ctggcaaaac agctaggaa tttgctaatc aaaaaaacct aatatgatat 14340
attttatttt gagtttttag tacataaaca catgataact gagttggcac caaaacttac 14400
actttatatg ttaaaaagca aaagaagggt taagtttttc taatggtggt agcaaataaa 14460
aaagaagggt atcttagcca ctattgtttt aaaataatat aattcactgt gggagtayag 14520
atacagccag tgacccataa aaaacttcaa aatagtactt ctgtagcctg attcctatga 14580
gtttggttga ataggattta aatgtatata ataaacgtct tttagtatat gagttaacat 14640
catagtactg ccctatactg tggagctaac acccaagatc taaagatatt ttgtaacaca 14700
tgtgaattac tctttcttgt tctttaactg aaatgagaag tatagaatct agatttaaga 14760

```
tctagctaca taaaaggata gaaaagtaaa atccatagga aaagttaaag atactgggat  14820
gtagtatgga ggagaggagg cagagagaaa taacctcaca attatctcaa gaagttttta  14880
gggcttctca tatggggaat agtgcccagg tgtttttctt ctctagtgaa tatgaaaagg  14940
gaagggaatg gaggaacaaa ttaacaatta cttaacactc atgatgtgcc tcagcagtat  15000
actcttcttt tttaatctat ttactgagat ataatttatg tatgataaac tgcattcatt  15060
taaagtgcaa aatggattaa ttttgacaag tgtttgtacc tgtgaaatca ccaccaccat  15120
cacatctaga tatagaacat ttccatagat aatcccccca aattttgttg ctgactgtgc  15180
tcaacactta attctcacaa acaccttaga gaaaggaggc aggggagacc ttagaaaata  15240
attttttaaa aaaggggaaa atgagaaatt aagtgacatg ccaaaggtca tatagctggg  15300
aagaagaaag gtgtcacctt tgaatacaac tcacaagttt cacttaactt tataatatat  15360
tcatactgga ttctttctaa ggtgatatgg cacgtagaat gtttaaaata aaacaagaat  15420
gcttatcaga agaagtacat ttaggttggg cgcggtggct cacacctgta atcccagcac  15480
tttgggaggc caaggtgggc ggatcacagg gtcaggagat cgagaccacc ctggctaaca  15540
cggtgaaacc ccatctctat taaaaataca aaaaattagc tgggcatgat ggtgggcgcc  15600
tgtagtccca gctactcggg aggctgaggc aggagaatgg catgaacctg ggaggtggag  15660
cttgcagtga gccaagatca caccgctgca ctccagcttg ggcgacagag cgagactccg  15720
tctcaaaaaa aaaaaaaaaa aaaagtgcgt ttaataattt aaatatacta acattttgtg  15780
tcttgatctt gatgatggct gcatgggtat aaagactatc ctttctccat tgaattgccy  15840
ttgccccttt gtcaaaavtc aattgatcat ttatgtgcag gtctatttct gggaactatt  15900
cttttctgtk gatctaygtt tcctgtcttt tcaccaatac cagtcttgat aaacgtagct  15960
ttataatgag caaaatcagg tagcatgatt ccttaacttt attcttcgac tcaatgacgy  16020
ttagccttat tttctaatag gcagtattta atgttaaaaa ttttcaaata catttctgtt  16080
ttatcctaaa aattttatag tttgttgttc agttttagat ttaaacattt tttcattatg  16140
atttcttctg taacctatag gtgttttcct atccttttat atttatatcc gatttaatgg  16200
cattgtggac agagtacttg gtccgttaag ctatgcactt aatatctatc tgtatactag  16260
ctatctgtta tacctcactg aataagttga aagaaagaac taagaatgct ggaatttgga  16320
gattcattaa aatggaaaga aacctaggtt gtcatcctgc ttttgtacgt tggatagatg  16380
cgtttttagt gtattttcaa aaagttacca atgatagaga atggccaagt ttgctggcaa  16440
cccacaccag gtgtaaaaat gtgtatagtt tcttcctaat atcagaatgt aaaagtagta  16500
attgggagta gctgaaacca tgccacatgg gttcatgatg gatagcaagg tcaccacatt  16560
gcacaacagc aggaggctct gtggcttggc accctctttg caacgtgaat gtgtattctg  16620
gagttgctaa acaccctgga aggaagtgaa gtaggggagt ggggtaggga acaaaagggc  16680
gactgagaaa aaaggataaa aaaaatagtg actgcaggtt cagtaacatt gaatggcaga  16740
tatatttaaa atcatatttt ataaaaataa ttgttttcca attatcttag gagcacacct  16800
ctaatgtagc cctgtaggct gtaatagcaa tagctaagag tgataagctc attttccatc  16860
ccacttcata ctgttttctg tatttcctgt ttctattatg acatctcaac catcttgtca  16920
ctgagaaacc ccagacttat atttgactct ttattgccct cttgtccagt tgtcaaatca  16980
tatttctacc tttgctgtat ctctcatctc tctagtcctt tctgttctta ctatcaatat  17040
actagctcag agtttcttaa ctccttgctt tgtctataga aatagtccct aaccaatttt  17100
cccrgaggct aattctcatc atctgtccag ctaaaacaaa aaaaaccttc agtgacagcc  17160
```

```
ctcacaccta tccatctacc actcatgaaa taatacctta ctttttagcc tagctctttc  17220
agccttctac catttggccc tcaaactacc tttgtggcca tttcttcctt ggtctgcatt  17280
ctaactagag ccattcacta tttacgttag atatactttg tgttatgttg cctgccaact  17340
cctcctcttt ctcctcctcc tcagtctaca cgaaaatgaa aatgacaaca atgaagacct  17400
ttatgatgat ctacttccac ttaatgaata gtaagaggta tattttctct tccttacaat  17460
tctcttttct ttcctttttt tttttttttt tttttctgag acagagtctc actggctgga  17520
gtacagtagg gcgatctcgg ctcactgtaa cctccacccc ccaggttcaa gtgattctcc  17580
tgcctctcag cctcctgagt agctgagatt acaggtgtgt gccacgacac ccagctaaat  17640
tttgtgtttt tagtacaggc ggggtttcgc cattttagcc aggctggtct tgaactcctg  17700
acctcaggtg atccacccac ctcggcttcc caaagtgctg agattacagg tgtgagtcat  17760
tgcacctggc cctttttttt tttttttttt aagagacgga gtcttgctgt gttgcccagg  17820
ctgaagtgca gtggcttgat catagttcac tgcaacctca aactcctggg ctcaagtgat  17880
cctcctgcct cagcctccca agaagctggg actacaggca cacaacactg cacttggcaa  17940
tttatttttt gcagaggatg gggttttgct gttgactagg ctggtctcaa actcctggca  18000
tcaaactcct ggccttaagt gatcctccca cctcagcttc ccaaggtgct gggattacag  18060
gcatgagcca cttcatccag ccccccttatg agtttcttaa taacattttc ttttctctag  18120
tttgctttat tataagaata tagtaataca taaaacatat aaaatatgtg ttaattgact  18180
gtttatgtta ttagtaaggc ttccagtcaa cagaaggcta ttagtagtta agttttgagg  18240
gagtcaaaag ttatatgtgg atttttgact gcatgggggt tggtgcccct aaccccctata  18300
tcgttcaagg gtcaactgta tttgtgcctt tagatctaaa atgcctctag tcagcatata  18360
gttgcatcat gtgttttcgt ccatttttct aatctctttt attagataat ttaatctatt  18420
tacatttaaa gtaattactg ataagaaggg gcttttgtaa ttttgctatt tattttctat  18480
atgccttatc actttttttgt tattttctat tttactgtct tttgtgttta attgatttat  18540
tcatagtaaa aaaaaatttt tttttttttt ttttgagacg gagtttcgct cttgttgccc  18600
aggctggagt gcaatggcgt gatctcggcc cactgcaacc tctgcctcct gcgttcaagt  18660
gattctcctg cctcagcctc ctgagtagct gggattacag gcatggccac catgcctggc  18720
taattttgta tttttagtag agacaagatt tctccatttt ggtcaggctg gtctcgaact  18780
cctgacctca ggtgatgtgc ctgcctcagc tccccaaagt gctgggatta caggtgtgag  18840
tcactgcacc cggcctgtag taaaatgttt aaattccttt ctcatttcct tttgtgtata  18900
ttctataact attttctttg tgtttaccat ggggattaaa tttaaccttt taaagttata  18960
acactaattt gaatttatac cagcttaact tcaatcacat ataagaactc tgcttctttg  19020
tagctctgtc cccacttctt tcacgtattg ttacaaaatt atatttttat atattgtgtg  19080
ccacaaaaca taaactaaga attcgtctca atacattaat ctcttaaatt atgtagaaga  19140
taaaaatggg gttacaaact atttttatga taatactagc ttttaaaatt gttcatgtat  19200
ttatttttat ggatatcttt atttcaccat gtaggactcc ctgagttttt cttgcagaac  19260
aggtcaagtg ataatgaatt ttgtcagctt ttatctcgga atgccttaaa aactcttagt  19320
tttgaaggac tgcttgttgg atattggatt cttggttcca gttgttttgt ttgtttattt  19380
agccatttga gtttatcagc ctactatctt ctggcttgca tagttttgat cagagaaatc  19440
tgttgataat ctcattgagg atcccttctc tgtgaggagt cacttttctt gctgctttca  19500
ggattctctc tttggctttt acaagtttga ttatagcatg tctcattatg ggtctctttg  19560
```

```
agttcatctt acttggagtt cattaacctt tttggatatt tatattaatg tctttcatca  19620
aatttgggaa gttttaaaca attatttctt taaatattct ttctatcctt gtcttttttc  19680
tctttttgga actctcacaa taggtatgtt ggtccatttg atggtgtccc atgggaccct  19740
taggctctgt tcactttctt taatcttttt tctttctggt agaygactca acagttgtca  19800
ttatcttatg ttcatctatt ttaacataac gttttaaaat tataaatttc cctctgagaa  19860
ttaatttaat agcagctcac gatttttgat gtgtcatatt ttcattttgt ttaattcaaa  19920
tgtttactaa tatcctttga aagttttctt tgatctgtta attctatgaa agtgtattgc  19980
tcaattttca gcatttgtgg attttctggt tatattttat tattggtttc aagtttaatt  20040
ccattatagt gagagaatat actctttaca attttgttcc tttgaaattt gttgagactt  20100
actttatggc ccttcatgga atctattttg gttgatgttt catgcacatt tgaaaaggag  20160
cagttgattg gtatagcatt ctgtaaattt caattaagtc acattggtaa ataatgctat  20220
ccaaacattc tctttccaga ctgatatttt gcccattatt ctatcactta ctgagatatg  20280
tatattaaca tcttcaagta ggatggtaga ttgcctgctt ctccttcccc cagttttact  20340
ttatatattt tgaagctatg ttaattatta catgtacata agtttagact tctgatgtgc  20400
tcttgtttaa ttgacccttt tatcattaca caatgttctg ctttatcttt agtattactt  20460
cttgctgtaa tgtctacctc tctgctatta atattgcttt ctatttgttg gtgttttaca  20520
cagtgtatct gtttctatcc tcttttaacc tatctgtatc tttaaagtgt atgtttaata  20580
aacatataga caggtttttt aaaaattcaa tccgatagtc tcttttaatt gtatgattta  20640
gtcartttag tccatctgca tttaatgaac ttactgatat ggctaggttt aagtctacca  20700
tcttgctgat attttctcat tgtcccattt gctcgttgac cagcattttc ctctagcatt  20760
ccttctttcc tgccctttta ttggctattt aagtatcttt taagttccca ctttattttc  20820
ttcattatct cttgttatac ctttctatat tactctttga gtaattatcc tagatattac  20880
agtatatatt cttaatttat tacagtctac cctcaattag taygtttact cttcctgaac  20940
aatgcaagta tcttctaaca gtttaaatcc ttagtcactt ttttcccttg gtactattgt  21000
tgtgctgtca aatatgttta gtgataagtc catttgcatt tcacacagtt ttcgaaatag  21060
ctgggtttaa ctttattctc ttcttgtttt ctgcttattt tgtctgttct ttgctccttt  21120
tttcatatgg gagatttcat ttatcctttc tggcccaacc cagcttttga ttgagtggct  21180
aagtctttgt tttctccact ctgaaagtta cgcactttgg agcttttgag ctaagctttg  21240
tatccccttg ttccatacag gttcaaaatc tgacaaaaat ctggctggga ggaggatact  21300
tgttatgtgt ttgttgtagg ctcctcctac aagtttaaaa tagataatat gttcacattt  21360
ttcaaagatc aaaaccaaaa ratacgttga tgtatatttc tctcatttct atgtctgtta  21420
acattttccc tccctgtgta ctaaaagaaa gcagtaagcc cttatctaaa cttccagtac  21480
ttctttttgc aaattcaagg aaatacaaat gcgtatttta acctcccatt cttagtagaa  21540
tagttcttaa tatataatag tcattcaata agtatttgtc aaatgaagca aagaacaaac  21600
attgtatact tgtgtggtcc catatggtag ccaggagcca tgtgtggcta ctgagcactt  21660
gaaatgtggc tagtgtgact gagaactgga gatgtgcaat gagtatcaaa taatccttaa  21720
attttgaaga cttaatgtga aaaagtgaac tatctcaata acttttatat tgattacatg  21780
ttgaaatgat aatattttgg atatattgaa gtgaaaatat attactacaa ataatttcac  21840
ccttttcggt ttttttcaat gtggctacaa aaattggggc caggcatggt agctcacgcc  21900
tgtagtccca gcactttggg aggccaaggc aggagggagg aatgcttgag gccaggagtt  21960
```

tgagaccagc ctggacaaca tagtaagacc tcatctttac caaacaaaac aaaacaaaaa 22020
aaataccagg tgtggtggcg tgtgctgaca gtcccagcta ctcaggaggc taaagtggga 22080
ggattgcttg agtccaggac ttcagtgctg cagtgaacat gatcatgcca ctgtactcca 22140
gcctgggcaa cagagcaaaa ccctgtctct aaaaaaagat acaaataaaa ataattaaga 22200
aaaatttaaa actagacatt ttatttctgt tggggagtat tgctatatgt actatcctgt 22260
atttcttttt tcttaacaat atatcctgga tatctgctca ttttaatata tggcttccca 22320
attcgttttt acaactagaa grtattctgt ttgtgtgaat ataccatcat gtatttagcc 22380
aagcctctat taatgagtat tgtacacaca gtgcagaagt acacacagtg tgtaccactg 22440
tgcccagcta attttttacc ttgcacataa atctgcacat gtatgaaatt atacaattat 22500
atatcagtaa aataaagtcc tggaagtgaa attgctgggt taaagataaa tgcatttgta 22560
acttcaatan tatgttgcca aattgctatc catagagatt atgttatttt gaactcccac 22620
caatatattt gggtacgtgt ttttctataa ccttgcaaca gaattgtcaa actactatgt 22680
caaacatagt atctcagtgt tcttttaatt tttattttcc tagttatgag gaaagctggg 22740
catagttcag ttgtttaaat actaattaaa atctttttga taatgtattt gtttatatat 22800
tgcttttata ttagtaagat tagccttttg tctataatat caattataga taattattta 22860
tagcttattt ttccttttac ctagcttatg ggatttagtt ttccatgcag ttgttttctg 22920
gttttactgc agtcaaatct atcaattttt tttaaaagcc cttcaagttc gagtcatagt 22980
tttaaaaaag ayttkccagm crggtrywky srcycmwgsm tgkaakscya ryancwyyar 23040
gwsgccgagg tgggtggatc acctgaggtc aggagttcca gaccagcctg gccaacatgg 23100
tgaaaccccg tttctactaa aaatataaaa agtagccagg tgtggtggca ggcgcctgta 23160
atcccagcta ctcaggagac tgaggtggga gaatctcttg aatctgggag gcagaggttg 23220
cagtgagccg agatcatgct actgcactcc aggctggcct cctgagtagc tgggactaca 23280
gatgtgtgcc agtgtgccca gctaattttt ttatttttag gtcttactat gttacccata 23340
ctggtcttga acttctggtt tcaaatgatc ctcccatctc ggcctcccaa agtgctggga 23400
ttataggtat aagccactgt gccaagtctc tatttggatt atgtatatgt tttaagatat 23460
agatccagat ttatcttttt taatatggct actctcttag tctgtttctg ctgctgtaac 23520
aatacttgag actggataat ttatagacag tagaaattta tttctgacag ttctgaaggc 23580
tgggaagcca aagatcaagg caccagcttt tggtgtgtgg tgagggcctt cttgttgcaa 23640
gctcacatag cagaaggggc aaatgctgtg tcctcacata gcagagggca gaagagcaaa 23700
aaagggccga acactatgtc ctcacatggc agagagtaga agagcataaa aaggcctaag 23760
ctagtttcct ttagcctttt tataaggaac tagtccattc atgagggtga agaaagcccc 23820
aactccttat gccagcacaa tggagattat gtttcatcat gaatttttag ag 23872

<210> SEQ ID NO 20
<211> LENGTH: 26747
<212> TYPE: DNA
<213> ORGANISM: Homo sapiens

<400> SEQUENCE: 20
gaattccatt tgtattccag gtggttcaaa caggggtccc tgagtcaggt tggagctcgc 60
caatagttca gtgcaccagc gagtcccggt cacacacggc tgatcaacaa ctgtgtattt 120
gcaaacagac tacgcaggtt ttcataccca tgcccagcac accatgagca gaccgtcact 180
cccttggaaa ggggctgaac cagggaccca attgtttagc tcagtggatc ccaccccccat 240

```
ggaggccagc aagctaaagt ccactggctt gaaattctcg ctgccagcac agcagtctga    300
agtcgacctg ggatgctcag tcttgttggg ggaggggcat ctggaggctt gagtgggcag    360
ttttcccctc atagtgtaaa caaaactgct gggaagtttg gacagggcag agcccaccac    420
agtgccacaa agcggcggta cccagactgc ctctctagat tcctcctctc tgggcagggc    480
atctctgaaa gaaaggcagc agccccagtc agggacttac agataaaact cctatctgcc    540
tgggacagag cacctgcagg aagggcagct gtgggcacag cttcaacaga cttaaacgtt    600
cctgcctggt ggctctgaag agagcagcag atctcccagc acagcactca agctctgcta    660
agggacagac tgccacctca agtgggtccc tgacccccat gcctcctgac tgggagacac    720
ctcccagcag gggtcaacag acatctcata caggagacct ctggctggca tctggcgggt    780
acccctctag gatgaagctt ccggaggaag gaacaggcag caatctttgc tgttctgcag    840
cctccgctgg tgatacacag gcaaacgggg tctggagtgg acctccagca aactccagca    900
gacctgcagc agaggagcct gactgttaga aggaaaacta acagaaagga atagcatcaa    960
caaaaagggt gtccacaaaa aaaccccagc cgaaggtcaa cagcatcaaa gaccaaaggt   1020
agataaatcc acgaagatga ggaaaaacca gtgcaaaaag gctgaaaatt ccaaaagcca   1080
gaacgcctct tctcctccaa aggatcacaa ctccctgcca gcaagggaac aaaactggat   1140
ggagaatgag tttgacaaat tgacagaagt aggcttcaga aggtgggtaa taacaaactc   1200
cttcaagcta aacgagcatg ttctaaccca atacaaggaa gctaagaacc ttgaaaaaag   1260
gttagaggaa ctgctaactg gaagaaccag tgtagagaag aacataagtg acctgatgga   1320
gctgaaaaac atagcacgag aatttcgtaa agcatacacg ggtatcaata gacaaatcga   1380
tcaagtggaa gaaaggatat cagatgttga agatcaattg atgaaataaa gcatgaagac   1440
aagattagag aaaaaaatga aaaggaacga aatatgggac tatgtgaaaa gaccaaacct   1500
atgtttgatt ggtgtatctg aaagtgatag ggtgaatgga accaagttgg aaaacactct   1560
tcaggatatt atccaggaga atttccccaa cctagcaaga caggccaaca ttcaaattca   1620
ggaaataccg agaataccac aagatactcc tcaagaagag caaccccaag acacataatt   1680
gtcagattca ccaaggttga aatgaaggaa agaatgtcaa gggcagccag agagaaaggt   1740
cgggttacct acccacaaag ggaagctcat cagactaaca gcagatctct ctgcagaaac   1800
cctacaagcc agaagagagc gggggccaat atccaacatt cttaaagaaa agaattttca   1860
acccagaatt tcatatctag ccaaactaag cttcataagc aaaggagaaa taaaatcctt   1920
tacagacaag caaatgctga gagactttgt taccaccagg cctgccttac aagagctcct   1980
gaaggaagca ctaaacatgg aaaggaaaaa ccagtaccag ccactgcaaa aacatgccag   2040
attgtaaaga ccattgacac tatgaagaaa ctgcatcaat taacaggcaa aataaccagc   2100
taacatcata atgacaggat caaatccaca cataacaata ttaaccttaa atgtaaatgg   2160
gctaaatgcc ccaattaaaa gacacagact ggcaaattgg atagagtcaa gactcactgg   2220
tgtgctctat tcaggagacc catctcacat gcaaagacac atataggctc aaaataaagg   2280
gatggaggaa tatttaccaa gcaaatggaa agaaaaaaaa gaaaggggtt acaatcttag   2340
tctccgataa aacagccttt aaaccaacaa agatcaaaag aggcaaagaa gggtattaca   2400
taatggtaaa gggatcaatg cagtaagaag agctaactat cctaaatatg tatgcaccca   2460
ataaaagagc actcagattc ataaagcaag ttcttagaga catacaaaaa gacttagact   2520
cccacacaat aatagtggga gactttaaca ccccactgtc aatattagat caatgagaca   2580
gaaaattaac aaggatattc agaacttgaa ctaagctctg gaccaagcag acctaataga   2640
```

```
cgtctacaga actcttcatc ccaaatcaaa agaatataca ttcttctcag caccacatcg   2700
cacttattct aaaattgact acataattgg aagtaaaaca ctgctcagca aatgcaaaag   2760
aatgaaaatc gtaacagtct ctcagaccac agtgcaacca aattagaatt taggattaag   2820
aaactcactc aaagccacac aactacatgg aaactgaaca atctaatcct gaaygwytws   2880
kgggwrgaym wyrrwwwtwa ggcwgmaata argragktrk wwraaacwga catgcagaac   2940
aaaracacaa tatwccagaa tctctgggac acagcaaaag cagtgtttag agggcaattt   3000
atagcgctaa atgcacacag gagaaagcaa gaaagatcaa caccctaaca tcacaatgaa   3060
aagaacgagg aagcaagaac aaacacattc aaaagctagc agaagacaag aaataactaa   3120
gatcagagca gaacagaaag agatagagac acgaaaaatc cttcaaaaac tccatgaatc   3180
caggagctgg tttttgaaa agattaacaa aatagataga ctgctagcca gactaataaa   3240
gaagaaaaag agaagaatca aatagacaca ataaaaatga taaaggggat atcaccactg   3300
atcccacaga aatacaaact aacatcagag aatactataa acacctctac acaaatgaac   3360
tagaacatct agaagaaatg gataaattcc ttaacacata cccctccca acactaaacc   3420
aggaagaagt cgaatccctg aatagaccaa taacaagttc tgaaattgag gcagtaatta   3480
atagcctacc caccaaaaaa agcccaggac cagatgaatt cacagccgaa ttctaccaga   3540
ggtaccaaga ggacctgata ccattccttc tgaaattatt tcaagcaata gaaaaagagg   3600
gactcctccc taaatcattt tatgaggcca gcatcatctt gataccaaaa cctggcagag   3660
acacaataaa aaaagaaaat ttcaggccag tatccctgat gaacatcgat atgaaaatcc   3720
tcaataaaat actagcaaac tgaatccagc agcacatcaa aaagcttatc caccacgatc   3780
aagtcagctt catccctggg atgcaaggct ggtttaacat atgcaaatca atacacgtaa   3840
tccatcacat aaacagaacc aatgacaaaa accacatgat tctctcaaca gatgcagaaa   3900
aggccttcaa taaaattcaa caccccttca tgctaaaaac tctcaatgag ctaggtattg   3960
atggaatgta tctcaaaata gtaagagcta tttatgacag aatctccacm sccmmtatcr   4020
kmctggatgr scmaargckg kwmsmawwcs cwwtgaaaac cagcacaaga caaggatgcc   4080
ctctctcact actcctactc aacatagtat tggaagttct ggccagggca atcaggcaag   4140
agaaagaaat aaagggtatt caaataggaa gagaggaagt caaattgtct ctgggtttcc   4200
agatgacatg attgtatatt tagaaaaccc tcagccccaa atctccttaa gctgaaaaac   4260
aacttcagca acgtctcagg atacaaaatc agtgtgcaaa aatcacaagt attcctatac   4320
accaataaca gacaaacaga gagccaaatc atgagtgaat tcccattcac aattgctact   4380
ragagaataa aatacctagg aatacaattt acaagggatg tgaaggacct cttcaaggag   4440
tactacaaaa cactgctcaa ggaaataaga gaggacacaa acaaatggaa gaacattcca   4500
tgctcatgga taggaagaat caatatcttg aaaatggcca cactgtccaa agtaatttag   4560
agattcaatg ctatccctgt caagctacca ttgactttct tcacagaatt agaaaaacct   4620
actttaaatt tcatatggaa ccaaaaaaga gcctgtatag ccaagacagt cctggacaag   4680
aagaacaaag ctgaaggcat cccccctacct gacttcaaac tatactataa ggctacagta   4740
accaaaacag catggtactg gtaccaaaac agatatatag accaatggaa cagaacagag   4800
gcctcagaaa ttatgccaca cctctacaac catcttatct ttggcaaacc tgacaaaaaa   4860
taagtaaggg ggaaaggatt ctccacttca taaatgatgt tgggaaaact ggatagccat   4920
aggcagaaaa ctgaaactgg accccttcct tacaccttat acaaaaatta actcaagatg   4980
aattaaagac ttaaacgtaa gacctaaaac cataaaaacc ctagaagaaa actmkagrya   5040
```

```
wtwccacywc rggatgtarr cmtsrgyaac msagyttcgk kacwaamaca ccaaaagcaa   5100
tggcaacaaa agccaaaatt gacaaatggg atctaattaa actaaagagc ttctgcacag   5160
caaaagaaac tatcatcaga gtgaacaggc aacctacaga atgtgagaaa atttttgcaa   5220
tctatccatc tgacaaaggg ctaatatcca gaatccataa ggaacttaaa caaatttaca   5280
agaaaaaaac caacaacccc atcaaaaagt gggcaaagaa tatgaacaga catttatcaa   5340
aataagacat ttatgtggcc aacaaacata tgaaaaaagg ctcatcatca ctggtcatta   5400
gagaaatgca aatcaaaacc acaatgagat accatctcat gccatttaga atgacaatca   5460
ttaaaaagtc aggaaacaac agatgctgga gaagatatgg agaaatagga atgcttttac   5520
actatttgtg ggagtataaa ttagttcaac cattgtggaa gacagtgtgg ggattcctca   5580
agaatctaga actagaaatg ccatttgacc cagcaatccc attactgggt atatagccaa   5640
aggattataa atcattctac tataaaggca cgtgcacacg tatgtttatt gtggcactgt   5700
tcacaatttt actcttatta tgaacttaga tttttttaa atgtttctta gttttggtga   5760
gaagaatttg agtttagcac ctttaaagca ctagaagtcc aatttccttt ttctgggaat   5820
tttaagaata ttcaaattac ataagaactt acttatctct gtaagtcaat aagaacagag   5880
ctccttgaat ttaagagaca ttatactgta ataatatcct ctatagatag gatattatat   5940
ctcacataat gagagggaaa ggcctttctg aattttggac acatagagac agagcttaca   6000
gcttcatgtc tacaagttag gcacaagtca agagtaaaca cagaaacaca aaatctctct   6060
ggtccaaaat caaagaggtg ttctccttcc cagtgggcat aacattttaa ttgatttgag   6120
cttaaagaaa atagacaaat tttttttaa gtataaccag agtctctgtc atctcaccca   6180
atagggatag atctatatca ccttctacag agatcatgag atggtcaaac tgtaaaacca   6240
aaacccttat tgtttttaca gttaatgagg aactgattaa tgagggaacc aatagatgtc   6300
acaactggct taaaggagaa ttcaaaccac acacatatgt acaggtaatc aaacatgttg   6360
aaatgaattt acaaataggt atgaaactag tcggtatcca cagggcaatc tgttttatta   6420
tactggacaa aattcatttg cattagcata agttttctac aatttacaga gttgtaaaat   6480
agctcgaaga caatgaaaat cacaggtatt tatagaatca gataacccag aaaggtgcat   6540
ttgacaggac acctggtcat ctttttctat tgtctgcttc agtctttctc tggagaacaa   6600
tccaggaagc aatccttgac ttcttggccc acttagacac aaggtcagcc aggccctaat   6660
ctttcaacat ttcagctgga acttacgaga ttctttgagc aagcatgggg gcaaggagtt   6720
tgtcttcacc tatccctgca tccttagcta ggtgaggcct tttcttgctg tctcactttc   6780
ctccatgcat cttgtgaccc atccagagga tcacttcaga gccaaacatt gcacagtgtg   6840
gaggtgggac tctgatggga gaaggtttaa cttggcaaag aattaccatt ggaataatta   6900
tcgagagtga cctggtaagg tctggtttca ccagggccct ccctgagggt cattcccaac   6960
cagtaactgc ccatagagcc acaggctcag acctgggacg gtccctgctg cctaggccaa   7020
ggcccagctc tgtaccctgt ccacaatagt agcaccccca gtcttcgata ggtggaatta   7080
tcatttgtca ggtgataaaa caaagactga aatctattta agagaagcag tttaggagta   7140
caaacataga atatatgaaa agctagttat atgaaagtaa aatgataaag gttgagtttc   7200
acttataatt tgaaaaccaa catttattgt gcttcttcat tggacgtgtt gtctcaattg   7260
tattttggtc tctcagcaat tttgctggac cttgctatgt gtttcactaa actcactttt   7320
caaaaggagt tgtcaggatt ttatgaattg ttttattaac cccagaaatt tttaaggctt   7380
tcttaagatc aaatggttaa gatagactgg ctcgtggcac tcttattaga taagagttct   7440
```

```
gcattttcat ctgtaaattt agtagaaggt tgtagttcaa agaaaaaagt tcagaatgcc   7500
tctgcaatat taattaaaac aaagtcctct ttactttgac ttttggcacc ataccatatg   7560
cttttaaaca tcaagaatta gattgatctt tagaaacacc ttaagaatgg aaatagcagc   7620
cttgaagctt ataataaaag aacagtttaa aatgcataaa acaactcctc tgtttagcta   7680
tgcattttgt taacactttt tattttagta accttacttc tgaaaaagat tcttcattag   7740
tgttctcagc agtaacaact gatacatctt tcttgacctc accatgctta gaacgaaact   7800
ttaaaagagt ataaatttta tttaaccctc acattttgcc agatcactgt tcttacagta   7860
agcacacatg gcaggatatg gtgatgaaac tatgggaacg tacctgctct cttaggtcta   7920
cttctcttta cctgagtttg tcttactgat ttgtgtcaca tatccaagaa tagaaactac   7980
ctttcagaac taactcaggt ttactgttca aagaagctga aggctaatga aaggcaacgt   8040
atactctaaa gatttttcat tttcttctta ttgctgcata ctgaagttat accaaattat   8100
gcatttgctt ccaaattttg gttatccttt tgattactgt ctttatcatc cattattttc   8160
tttggaaggc agctggcaaa tactccatta tgtcatcagt aagagttcat tttctatgta   8220
ggaataccac gcagagtaac aactgtgact tttgcccagc tctaatactt aacttctttt   8280
gtcaggaagt gaactgatgc tggcttctct ttgtcttatt ccaagttggg catgagattt   8340
tccctgcatt agaaggttgt tgagacctga agcctgggaa ggtaagatgc cagcatgaat   8400
actgtctgtt gagaactgtg gtttaattga gtgtctggtg atttaagagt gtaagtcttt   8460
ccagctgttc ctggtttatg gtcttgaacc cttgaagttt taccaaaaca tggacagtga   8520
aacacttcta caatggaaag gcccattaac atattattta taatatttaa acataattgt   8580
atatttattg aaattgttac ttaaaggaaa aatggacaca tagcaatttc tatgtataga   8640
tactttgtat atacaagtct atatgtatca taaaataata aactaagaaa aacatatatg   8700
tactttttgt ttgtagtttt actttttctt ctgatttttt aatagacttt tatttactta   8760
tttttgtctg ctttgagaca gggtcttgct atgttgccca ggctggtctc aaactcctgg   8820
catcaagcca tctacccaac tcaaactccc aagtaactga gattacgcac tcagctgcat   8880
gccactgcac ccagcactag actttttttt tttttttttt tttagatgga gtttcgctct   8940
atcgccaagg ctggagtgca gtggcacagt cttggctcac tgcaacctct gcctcctggg   9000
ttcaaatgat ctcctccctc agcctcctga gtagctggaa ttacaggcac ccaccaccat   9060
gcccagctaa tttttgtatt tttagtagag acggggtttc accacgttgg ccaggatggt   9120
ctcgaactcc tgacctgacg tgatccgccc acctcagcct cccaaagtgc tgggattaca   9180
ggcgtgagcc accacaccca gccttagact ttattttta gatcagtttt agatttcctc   9240
cctgatcgtt ttttgaggcc agcaaagtaa ggagagtaaa gactcgattt tgttaatatg   9300
gagaaagaag acaacattaa gaaaatcaac aaattataaa gttttgtctc agtactctca   9360
tgacccaacc agcattctat gggtgttttt cccaaaaagt ctccattgga aaagactagc   9420
gaatgcacac actcagtaat gagggtcatg tttttacact actgttgctt actctcacca   9480
tttgttcgac atgcttcttc attcactgtg ccttagctag ttttagtaaa taaaatgttt   9540
caaattttca atgacttact taagctaaga aattatagtc cttcacaatg aaattataaa   9600
caatatcctt cctagtgaca aatatggatt attctctatg aagacttatt tatacacaac   9660
atgtagttca tttagataca acttgtagtt catttcagca tataaattat ctgggtaaca   9720
gtcaatctta aaagaatcag attttgcggc caggcacgtt ggctcacacc tgtaatccca   9780
gcactttggg atgccgaggt gggcagatca cttgaggtca ggagttcgag acccacctgg   9840
```

```
ccaacatggt gaaaccccgt ctctactaaa aatacaaaaa ttagctgggt gtggtggtgc   9900
acacctgtgg tcccagctac tcaggaggct gaagcaggag aatctcttga actcagaagg   9960
cagaggttgc agtgagctga gatcacacca ttccactcca gcctgagcaa caaaagcaag  10020
actccatctc aaaaaaaaaa aaaaaaaaaa aatctaagat tttgcttcat aactggactt  10080
aaatttacta atacatttga tgtactaata atgatcagtt tttaatggtg ctaatgtcat  10140
ataaatgtga cgttaacaca aaaattttgt gagattgaat gttagctaaa tatctctaca  10200
tattattaag aatctaatag aggctttaat gaagttacat ttatagcact agctaataaa  10260
agatgcaaag gtcacaagct agtcttctct cactgtttct cggcctataa aaatctagta  10320
ggggtttcat aggattttgg caacatttgt ttgttgttat atggctgtag actttttttt  10380
tttttttttt ttttgagacg gagtcttgct ctgttgccag gctggagtgc agcggcgcga  10440
tctcagctca ctgcaacttc cgcctcccgg attcaagcaa ttccctgcct cagcctcccg  10500
ggtagctggg attacaggcg cctaccacca cgcctggcta atttttgtat tttcagtaga  10560
gatggggttt caccatcttg gccaggctgg tcttgaactc ctgaccttgt gatccaccca  10620
ccttggcctc ccacattgct ggaattacag gtgtgagcca ccgcgcccag ctgacttatt  10680
aaagggatcc aagcccatgt tgttttcttg aacawttcta atagtttcat ttttgatttg  10740
tttttccat ttttcatgag ttgcaaattg aactttgatt gacacagagt atcaggtgga  10800
agccagattt gacgtatgcc agtattagac tttctccyty ccaggataga ccagcccaag  10860
tgaarwrgca ctgacattgc atmwsssktw ggtttwgcsa mstcwyttak aryagytrta  10920
aacawggkrt ytwwwwmwgw raamyamtsw ymscmcattt attgatcacc atgctcttaa  10980
ccttttctag ttataatttt tcttagttat tttattcctt gtaaacacac ttgtatagtg  11040
tgtttcagtg ttcaaagcac tctagacatt cttacttgat tctgacaata gccctatgta  11100
gttaaagcat gtgatgttat tttgatttca cagtcttaag tgacttgccc aagatcacat  11160
agccaacaag catggaaata gggtgaagaa accagttttt tccagttcac agtccagtaa  11220
tgtttcttga agctaaatgg tgctctgttt gtttacatga ctaaaaactg agttatttta  11280
ttcatgtgaa aggtctccta tgttgtaaca acttccttga atgccacaga atcgaatgaa  11340
tgtatttcat gtcaatgtac taaacgtagc ttctgtgttt gggagcagat aattggtggt  11400
attcagccag aaaaccaatt tgtataactt agattctgaa tttcagaatt tctcacctag  11460
tggagtattt gtacctgttc cagcatccat cttcaattcc aggaaaacat gggtgatcct  11520
ttattgcttg gtattcacct cattaggtgg cacaactgtt tgctaaaaca gtttgtgcag  11580
aagtaaggtc cagaagtaat ttagcaagag agttacttac ataaagactg agagctacgt  11640
agttctgggt aaatgctggt gcaacatgac ctctttgtgt tttgtataaa tgctgtgcta  11700
gtactaccag ttgtctatat ccacttaatc caccccttact tttgaaggag tcgattaatt  11760
ctgtttgcct gaaatttgat aattgtatca tcaatgaagt cataacattt tcataaatga  11820
gctagagctt taaaagtaga atccttgtac acagtcattg gtaggcagtg tttacttttt  11880
tgtttggtaa atatctgaaa ttttaaaatt catttttagg ttagccagtc ctacttcctg  11940
gatagtaatg taatatttaa atttgtcttt gcctttccct aggttctgtt ttgacctaac  12000
aatgataaga ttgtttatcc tttgaatttg cttaaaatta ccatcaggtt tctactttcc  12060
cacaagagca tgtgattgct ttatcccagc tgtaagataa tagaacaacc tagtgttgct  12120
tggtttactt tgtatgcctt tttctatttg cataaaccct gatctgatta caaacttgta  12180
tttacaccat tcccttgact ccttccaact caaagtattt attgtccagt taaaacattt  12240
```

```
atggtcatat aagctggctt atcttttttt ctttgatttt tttttgagtc agagtctcac  12300
cctgtcgccc aagctggagt gcagtggccc gatctcggct cactgcaagc tccgcctccc  12360
gggttcacgc cattctcctg cctcagcctg caagtagctg ggactgcagg cgcccgccac  12420
catgcccagc taattttttt gtatttttag taaagacagg gtttcaccat gttagctagg  12480
atggtctcga tctcctgacc tcatgatcca cccgcctcgg cctcccaaac tgctgggatt  12540
acaggcggga ggcactgcgt ccggcctctt tttttctttt ttttatttgg aatagcctsk  12600
yacwytgwkk ctmwrsctgg astrcrgkgg tgsaawmagg gctcactatg ccttgacctg  12660
ggctcaaktg attctcccac ctcagcctcc tgagtagttg tgactacagg cgtgggccac  12720
cagccagcta atttttgtta tttttttgtag agacggtgtc tctaccatgt tgcccaggct  12780
ggtctcaaac tcctgggctc aagccatcct cctgcctyta kyctcgcaaa gtgctgggat  12840
tacaggcatg agccactgtg cccggcctga atttcaatct tacttaaact caaacagcct  12900
taagaaatct gagtaatgag tttatagctt ttaaaagaga tcttccttat caaaaataat  12960
tatactatct cgtttcagga ttacttatca atggttctgg ttattttttc tagaatggaa  13020
actgaaccct atctttaaca ttatttaaaa acttgagagt tattttaaaa gtatgacagg  13080
aattgctctc acagctaaaa tttttcctta aaaaaccttt agcagtcaca aataattgtt  13140
acctacttaa ttctatttaa aaaaacagga atgatagaag ggttttattt tatttttgtt  13200
attttaaaga tacttttgaa aaccgtttag cacccagttt tcttttactc tgtggaatgc  13260
tgmccctttc cttytkkgkt tattttgtaa tggcacatgg mtmsayygyc gmyggtggtc  13320
tctatgtcaa ctttctattg gtgcgtgtgt gtgtgtgtgt ttatgtgtgt ttattccatt  13380
tccctttttgg gaagcaggaa ttggagctgg aagagaaaga aacaaattat tttcatctaa  13440
tctttttttct cctcagctta tttaactgac ttaaactatg gaaaaattgg taatttatat  13500
kyaamwwkwa krrakwgksk ykmcywsyrk rkwkrywwtw watytacwya tatatgtata  13560
tatatttttt gagacagggt cttgctctgw cacctaggct ggactgcagt ggcmtgatca  13620
tagctcactg caacctcaaa gtcctaggct taagcgatct tcccacctca gcctccagag  13680
tagctgggac tacgggtaca accatgcttg gctaattttt tttttttttt tttttgagat  13740
ggagtcttgc tctgttgcca ggctggatgt gcagtggcac gatctcagct cactgcaacc  13800
tccgcctccc aggttcaagc aattctcttg cctcagcctc ctgagtagct gtgactacag  13860
gcgtgcacca ccacacccag ataatttttg tatttttagt agagatgggg tttcaccatg  13920
ttggccagga tggtctcaat atcttgacct cgtgatctgc ccgcctcggc ctcccaaagt  13980
gctgggatta caagcgtgag ccaccatgcc cggcctaatt ttttaatttt ttgtaaagac  14040
aaggtctcac tgtattgccc agatagatct tgaactcctg gccccaagtg atcctctctc  14100
ctcagcctcc caaagtgctg ggagtagagg cgtgagtcac tgtgcctggc cctccaaaat  14160
atttttactt tcatttaagt ttgctaccga yatcctmtcc ttactttccc tatgtcccct  14220
taatcttatc tttatggtag tttaggagaa tctagactgc cgctttgctt aactgatacc  14280
gccccgggaa gctatcacca atcacatcac tgcctcacat tgagtaggac ttgaagttca  14340
tgaaacatct ttaatatgct catctaactc aaattgatcc tttgtgctat atcttgatgt  14400
tcttttctct tatttgtttg tatactgctt tattagacta tcacattagt tatcaaagct  14460
agtagttaat tcacatgttg attttctagg cctgtatcct tattagtcta aggtggaaga  14520
aacagagata aaatttctaa atacctacct aaactggaaa ggaataagga agataattaa  14580
tttagtagaa tcaacctttt tattcttgac aaaatctggt taaaacaaac tggttttaca  14640
```

```
cacacataca ctttttttaca cagaattatt gctgagtata ttagttaata ttaaagtgtt  14700
ttttatttta aatgckrmta kgtkgamatt gakcykgtgc cawmcwgtgg tgcgawwcty  14760
gttaatttat atcaatctct gtgttttata atcctttgaa catattaaca aggaaaaagg  14820
aatgattggt aataccaaat attatggttc tttgttatat agttttagag agctacaggt  14880
aattggctat aaaatatttg gttggcagtg gagaatattt ttaaaattct atagataaaa  14940
gtaataagga gtagagtaga actaccagat attcaaatat attataaagt aacagtattg  15000
aagcagtgtg gcaaaggccc cagattagat gtgtagatca ttgaagaaga atagaaataa  15060
atgctgttat ttatataaat ctgacatatg ttaaaggagg ccctgttaaa cactgggtaa  15120
tggattgatt atttaatgaa tggggttgga ataaccagtt agcagtttta aggaaaaatg  15180
catttagatc attatctata ccagatacaa caaaaagtca atttgtgata aagtgtggac  15240
atttatatga ttgaaaatct acaagataaa aacactgaat actctataat ttatctggag  15300
ttcctaagca gttggaaaac tggaaaaaga agatagtaaa aaattgtttt attataacaa  15360
atttgcattt gttttattgt aactggtaga tctgtgagcm ttataggraa acctgtctac  15420
tccatgttca caatctgaaa attagtctcc tttttcttc acgtcatctg gaaactgttt  15480
ttcttccaaa ctagctaatg aaacacagaa tgcaattctt tatctaaaat tttattctgt  15540
aggtgcgttg aaaactatac aggagctcgt tgtgaagagg tttttctccc aggctccagc  15600
atccaaacta aaagtaacct gtttgaagct tttgtggcat tggcggtcct agtaacactt  15660
atcattggag ccttctactt cctttgcagg taagtaaaat agaaacatgc ttttgagaaa  15720
agtaatacat aaagtagtta ttccactaaa taattaatat gcccttagtt ctagatattt  15780
ttccagatac tgtattatgt ttagttatct ctttaataca gtttttgtta ctaatttcat  15840
ttttgaaaga atcttaataa gcagtctcaa tttgttcttt gttactgttg tcaatattta  15900
ccttgactta tctaaactac taaggtaaac ccatactcac tatagcaaat atgccaaaag  15960
cacctgaata tttgggttag gtgtatttaa agtaaatttt gtatgtgaaa gaaaaggaay  16020
arstgtaygm rmtacwgtac rtgtkrtgsw waagmstata tggttaatat gcagggtcag  16080
ctatctagtg cccactattg tgctaggcat aaagaataca atagtgaaca aaatagacat  16140
gtttcccaac ttcaaagata cttaaatcaa tttggagaga cagacaaaaa ggcaattaat  16200
ttggggaaac tggtaactca caagagagac aaaaaaaaaa actacttgca tgaagcaatt  16260
atgcactgaa gattactttc attcgttttg attttcaatt gtttttgaaa ttttgtaaaa  16320
gtaaatatag aatttagtaa gtccaggagt tatttggcat aactctcatc attaattaat  16380
atttatgaaa ctcacactgt attctatcat agatacttgt gaaaatggag ctgaaggtaa  16440
tcataaaaga gagacaagtg ggcttgagaa gtttgtatac taagaaaggt aacatatagg  16500
taaaatagta tcttgttaga tcctgatttc ttaactactt tacatcaagg aataattaaa  16560
aattggagga aattggcttt ttaaaaatat gtggtattaa atagtttatt ccaaaacata  16620
tcatttaagc aatccagtag attttatttc tcataatttt agcatctgac tacttcagat  16680
acaaaaattt aaatacaagc ccattgtatc agattgcatt tccgagggat ggccatatga  16740
tatccctcat tcccacatac tcttctgtag tgtgaccttg ccactcatcc atcaagaggt  16800
agagtttatt gctacagatt ccttgaatct aggcaggcac cgtgactgcc ttgatcatag  16860
actacttggg atgctgcctc atagaatcag ccgccatgtt gtaagaagcc taaacagcag  16920
gaagaaccag ctccagctga acttccagcc aacagccagc cttaactgct ggccatttta  16980
atgagccatc ccaggcattc agctcattca aacctttagt tgactcctga cttaactgcc  17040
```

```
agtttactgc agctacacag agagcccaag caaaagatgc ccagctgtca acccacagaa  17100
tcatgagata aagttttttt atccccccaag tttggggtgg tatgttatgc ataagtagat  17160
aaccagaaca cccatctttg gaattaggtt tatgcttgac tttaaatgta tctatgtttg  17220
gaaagctgaa taatgatcta ttctatccct ctaaacattc tgtcagtcta atatgctaag  17280
gggaagacca atacctactt ccctcattaa tcactctctg tgccagtttg gagatatagt  17340
ttccatctgt tattgattgg ataatgaatt gtgtttaatt aatgaattat gtttaattca  17400
ttatcattaa taagtcagga tagtctaagt ttggctgcag taactaccaa ccctaatact  17460
ttagtggctt aataaacaga agattatttc tcacttattg taggtaatta gtatggattg  17520
gcaagcaggg ctttactaat catagtcact taaggactca aactgttgga gcaaccacca  17580
tcttgagtgt tgctggttgt cataacaaag ggaaaagaaa gctctggaag gtctcacact  17640
taaattaaaa tgatctgtcc cagaagtgac acacatcact actgacataa ctcactagcc  17700
agcaggagtt tcatggtcct cctcaattat aagaggtggc tggacatggt agctcatgtc  17760
tgtattccca agtgagagga ctgcttgagc ccaggagttt gagaccagcc tgggcaagat  17820
cacaagaccc tgtctctaca aaatgaaaaa taaaaaaaat tagcagggca tggtggtaca  17880
catctgtatt cccaactact cgggaagcag aagcaggagg atcccccaag gccaggagtt  17940
tgagatgcag tgagctgtga ttatgccact gcactccaac ctggaaagag aacaagacct  18000
ctgtttccta ttttatatga atagattaaa tagataatat ttatttatat atttatttac  18060
atatatttac aataagagac atataatata tccagctgtc aggaaatgca attcaatcat  18120
atgctcataa gataaagagc cagaaataca tatctaatat agtgaccaaa ggatttataa  18180
gaatatctgc tattccactg ggaattgttg agagtgattt gtgtgatatt aaatccatag  18240
aacttgggcc aggtgctgtg gctcatgcct gtaatcctgc caaggtggga ggactacttg  18300
agaccaggag tttaagacca gcctggacaa catagcaaga ccccgtctgt acaaaacaat  18360
tttttttttt aattatccag gtgtggtaac acatgcatgt agtcctagct gcttgggagg  18420
ctgagatggg aagatcgctt gagcccagga atgagaggct gcagttaagc catgactgca  18480
ctactgcact cctgcctggg tgagagagca agaccctgtc tctaaaaaaa ataaataaat  18540
aaacaaatta atggaacttt aatattgttg tagttgcccc aaaatgaaat tcctttgcca  18600
acccattgag tttgtgaagg gcatagtata ttgtacccca caggtgttca atgccccaga  18660
gcagcaaagt ttcagaaagg agaccttcta agctatagct gttctgcaga cttgtgccag  18720
aacttagaaa tatttctagt ctgaagtacc ctgtagcagg ctaaacaata ccttttgagt  18780
agaaagtata ggtataatag aaggaaaagc gtatatatat aagaacaaga agtggtgctg  18840
aatacaagag aaaagaaagc tccaatcaca aacattatgt gggtctccat cctgaattca  18900
cactctctga atgtctgggg gtaaaaagct aagaatataa aataatctag gctggtaatg  18960
tcatcaggtg gttgacagaa acaaatacaa atcaattctt gaagagccta cttttatcct  19020
ttaccttgaa aagcgtctca cagtatgaaa agattaccaa rcrtmswrtr awaktaggcw  19080
tcrayytmtk wgractrgma gawacmstag gtagtagggt aagatattca kaaatctgta  19140
tttattggga agaatcagac acatgatata aaataagtat gtttaatatg tatcaaaaaa  19200
taagtgagag gtggccgggc acggtggctg atgcctgtaa tcccagcact ttgggaggcc  19260
gaggagggcg gatcacaagg tcaggagatc gagaccatcc tggctaacat ggtgaaaccc  19320
cgtctctact aaaaatacaa aaaattagcc gggcatggtg gcgggtgcct gtagtcccag  19380
ctactcgtga ggctgaggca ggagaatggc gtgaacctgg gaggtggagc ttgcagtgag  19440
```

```
ctgagatcgc accactgcac tccagcctgg gcaacagagc gagactctgt ctcaaaaaaa  19500
ataaaaaata gaaaataaaa attaagtgag aggcttagaa ataagcaaat gtggcaaaag  19560
actaaaacag atctccaatg aatcaaatat aatttttaaa aattcagtac atatcttcaa  19620
taaattttta aaatttagtg tatgtcttta aacagcagat taaacacaat caaaataatt  19680
aatgaattgg aaaatagata ggaaaaaatt acccagaggg taattctaag agaaaaagaa  19740
atggaaaata ttgaagagaa gtcaagaagc atggtgacca gagtgtgtgt gtctacctta  19800
tgtttagttg gaattccaga agaaaaagac tggggcagag gcagtatttg aaaaagtaaa  19860
ggcagagacc ttttcagaac tgatgaaagt tacccgtaga tgttagaagc ctaacaaatc  19920
tcaagcagga taaataaaaa taaatttaca tatgggtgca acatagtgaa attgtagaac  19980
accagttcta aagagaacat cacaaaagca gaaaagaatg gcagattatc gtcaaagatg  20040
caacaattaa accaacagct gacttctcag ttgcaaagaa gcaaaactag aagacagagc  20100
agtgatattt tcaatatgct gagagaaaac agttaacccc aaatttctgt ggcagtgaaa  20160
acatctctca ggaatgaggg taagatgaag acaactttta ataagcaaac tttgagagag  20220
ttatccctca gtaaaccttc tgcctgaagg atatatgtca ggtaaaagga agttgatcct  20280
atacggcgtg tgtgaagtgc aagaaagaac agaaagctat tactatgtga atatcaaaac  20340
aaatattgta taaattataa catagtattg tcctatgtat ttttttaaag gaattaaaac  20400
acatgatagc aaataagctt aaagtgtact aaggtctttg tatgggggga ggataaatat  20460
ataagttaat tttgaccttg atattttaag atgagtatta aaatgtctag ggtaacacat  20520
aatagaaaat caaagtgtat aattgccgga ttagcagaag gacaaaaatg gaattaaaaa  20580
taaccaatta gttaaaaata aataaaaaag aaagctaaaa aacaggataa atagaaagtg  20640
tgtcacaaga tctaggctgt cctgtagtga ccatgtgaac ttggaaatgt gctttcaaga  20700
atgaaattgt tttctgtaat agtttttggt ccattagtgg ttgaaattgc tttaaactga  20760
ggtccttttg aactttagta actaattagt gccatcattg aaggaggtcc aaaatgatac  20820
cccactaatg ctaaaatctg ggctagaatc agtagtgtct ccggaatagg agcaagtatg  20880
cttttagaaa atacacatca ttttgcaatg gtaaaagtga ttttgaattc attttcatta  20940
atgtaagcta aaactgcata tagacatatt gcaaaaaatg aaatcaactg tacattccaa  21000
aatctataac ataaatcata acctatatta actgatcaaa tgactgaaaa acctgatgta  21060
ctgttacctc aaaaatgtcc aaaattactt tttaaaatgc cattactaga ataattgact  21120
aaaggcaccc catgtcacat aagggtccca actgataatg aaagctaact tctttaaaaa  21180
gagcacaaaa attacattaa gatacaacag ctttgctgtt gtcttaaagg aaaaagacca  21240
ggtggcatca tcagcatctg gtccccacag atgatctatg tgtactaatg gatttgttaa  21300
ataatgggga acagttttaa agcatcactg acaatttcag gtagttgtgg aaagaaaatg  21360
aaccatcaaa tagtcaagtt tatactttca tttgatgtgt tgtaaaaagg gggaagaagg  21420
gaaattaaaa aaaaaaactt tctttctagg tcttctgaca tgcttttcct attacacttc  21480
catttttgtg tttctctcct ctttattgtc aggaaaggcc actttcagag agccagttca  21540
gtccagtatg atatcaacct ggtagagacg agcagtacca gtgcccacca caswsartra  21600
astmrmwaca raykyttrtk ktrrawymct msatgagact gttgttgtta gatgtaggga  21660
tttgtattta satctatcca gaaaaaaaag gttgagccta aacttttcta tgggtttttt  21720
ttttttttt ggccaggtac cctttttcac ataaaaatga atttattatc agtatgacac  21780
aaatcacatt ttttcccaaa gaaaacaatg ttatctcaat atatgaaatt ctgatgtagc  21840
```

```
tctaatgtgc tacacagata taagggactg gtttctcaga aatattttga agtgagccab  21900
cctatgggga ggaagaagag ttttacctgt aaagatcagc aaatctttgg gaaacttgta  21960
gacaaattga tgttttaaaa ttgtcttgag acttctggcc aagatggagt aacaggcact  22020
ggatttattt ccttctactt aaaacaacaa aaaatggaca aaatatatgg agcattaaaa  22080
tttatgaaga caaaatatat gaagacattg gtatcagtca tcaaaggaac catgagccct  22140
gagagatggc aatagactag ttaagccaat gattgcctta gattactgcc tggagagaat  22200
ttccaggctt ttgtgcaagg tgggggaccc caggctgagt ttggctgact ccgagttgag  22260
aagatggagc taagagtcca aaaagatcaa ggtgactata ttgtactgag gagagtcctg  22320
gaaaaaagag aggtgtatga agagagaact ccagagattt tcagttcaag tattcagctg  22380
agtactaatc agggcatgtg tgggaggaaa atacttgagg ttgtggaaaa aatcacctga  22440
aggattagag gtgcccagta ttcacacagg gccaggaaaa gtgtctgttc ccactgaggc  22500
tggaaacctc attattcacg gggcacgggg tagagtacat agaaaggtgt ttgcctgata  22560
gtggggmata ctagccctag attaagcact gctacagttc tgcctaataa actgtaaaag  22620
catgagctga cagaatcaaa ttgtttccaa ataactacat cctagatcaa agctcaacaa  22680
tgctgaaaaa tagctagtac ccaacaggtg aaattaataa tgtttcacat ccaatacaat  22740
taccaacctc caaagaagca gaaaatgtgc tcaaaatgag aaatattaag aaactgaaag  22800
ccgggcatgg tggctcatac ctgtaatccc aacactttgg gaggctgagg cagatggatc  22860
acttgaggtc aggagttcaa gaccagcctg gccaacgtgg tgaaacccca tctytactaa  22920
aatacaaaaa aaaaaaccaa tggtgggtgc ctgtaatccc agctactcgg gaggctgagg  22980
caggagaata gcttgaacca cagaggcgga ggttgcattg agccaagatt gtgccactgc  23040
actccagcct gggcaacaga gcaagattcc gtctcaaaaa aaaaaaaaaa gaaattgaaa  23100
ttgatacaga tgctttaaat accaggcaag cacagttatt ataaatgtat tacatagatt  23160
caaaagtcaa gtagaaacat ggaagatata tttttaaagg acccaaacca aacttccaga  23220
gatgaaaact agtgtctgag atcaaaaaaa aaaaaacaaa aaaacaaaaa ctggatggta  23280
ttaacagcag attacacacc atagaaaata ttggtgaact tgaagatata gcagtagaac  23340
taagaaaaaa agaaatgcag aaagaaaatt tttttaatga aaagagcatc agtgaactgt  23400
gcgacaactg caggtggcat aatgttgagt ccctgaagga gataagagag aggagggaac  23460
agaagaaata agagtcaaaa atttttgcag atttaataaa agcaatcaat tmacacatat  23520
aaaaatttca acaaaaggsc tkkcmcycws scgtmacggc ctkwwaymcc agcattcygs  23580
grggmwkasg caggaggatc acttgaaccg aagagtttga gaccagcctg ggaaacatag  23640
tgagacctca tctctacaaa aaagaacaaa attagctggg catgatggtg catatctgta  23700
gtcccagcta cttgggaggt gggagaattg cttgagccca ggaggtcaag gctgcggtga  23760
gccaagattg tgcccctgca ctccagcctg agtaacagag tagtaataca ccaagacaca  23820
tcataatcaa attgctcaga accagtgata aagtcttaaa ggcagctaga aaaagacaca  23880
ttacagacag ataacaaagc taaggatttc agcaggcatt tttcagaaat aacacacctt  23940
aaaagaatgg agcaacatct gtaatgtatt ttaaaaagta aacctataat tctacatcca  24000
gcaaaaatat ctttcaaaca caaggcaaaa taggcaaatc aatcttggaa aagatgaaca  24060
aagttaggag actcacactt cctaatttct aaacttatta tgaagctgca gtaatcaagg  24120
caaagtagtg ctggcataag gatagacata tagatgaatg gaatacaatt gagagttcag  24180
acataccttc ttacatttat agtaaatgca ttttttaaag ggtgccagac aattcagtgg  24240
```

```
ggggtaataa tagtcttttc aacaaatggt gctggaaaaa ctggatatcc actcacaaaa  24300
gaatggattt aaacccctac ataccatata taaaaattaa ctcaaaatgg atcaaagatc  24360
taaatataag agctaaaacc atataactct tagtagaaaa cataggtgtc aatcttcatg  24420
accttggatt aggcaatgga ttctgagtta tgattctaaa agtacaagca acaaaagaaa  24480
aaatacaaaa actggattca tcaacattaa aaacaaaaaa cttttgtgct tccaaggata  24540
ccctcaagaa agtgaaaaga caatctactt ctgagagaaa attttttaa tcatacatat  24600
gagacttata catatgatct gaaatacata tatgtagttg aatatataaa caatatttac  24660
aacttaatga agaaacaact cattttaaaa atgagcaaag gattggaaaa gagttctcca  24720
aataatatgt acaaatgact agtaatctca tgaaaagaca atcatcatta gccatcagga  24780
aatgacgatc aaaaccacaa tgaaaccaag tgtggtggca tacttctgta gtcccagcta  24840
ttgggaggcc gcagtggagg atcacattgg takyssagga ryttgagkmy gagscyggst  24900
mrswkrgsag gagassccat ctcttaamaa aaaaaaaact ttgaggaggg cgaaaaaaaa  24960
gaaaaaaaat gcacatgaat gttcgtagca catagcagca ttatttataa tagccaaaaa  25020
gtagaaatta gtcaaatgtc catcagctga taaatggata tataaaatgt gttatattcc  25080
tactatggaa tattattcgg caggaaatag aaattaagta gtaatatatg ctgcaacatg  25140
gatggacttt gaaaacaaca tgctgaagta aaggacccag tcataaagga acacatattt  25200
tataacattt atatgaaatg cccagaacag gcaaatctat agagacagac agtagattaa  25260
tgtttgccta ggattggagg aaatgggggg atgttgggga gtgacggcta agggatgtgg  25320
gctttctttt tgggaatgaa agtgtcataa atttgattgt gctgatggtt gtgcaactct  25380
gaatatacta aaagccattg aattgtacaa tttaaatgag tgaattttat ggtacgtgat  25440
tgtatctcaa aaccataaaa aatcagtaac tatttagaaa aaaatgaagg caaaatagag  25500
attttccagg catatgacag ttgaaagaat ttatyatcac cagaacctca ctaaagtaaa  25560
tgttaaagga agyccttcag gcaaaaggac aatatcagat ggaaatatgg atttacataa  25620
agggaggaag agcaccagaa atgacaacta tgtgggtaaa tgtgtaagat ctttctcgta  25680
ttatttaaat ctccttaaga aataactgac catttaatga aatatcataa caacatagta  25740
tgggacttac aacatacata aaagcaaaat gtataataag aaaatacaaa gattgggagg  25800
gtagcgaggg aaataccccca ctgtaaggtt cttatgctga atgtcaagca gtacgtcatc  25860
acttgaaggg aaactgtaat aagtcaaaag tgtatgctag aaactctaga gcaacctgta  25920
aaaagtctaa gtcacccagt taagatagag attgtaaaat tggataaaaa ttaatgtgat  25980
atgctatctg caagaaatat acattaagta taaagacaca agttaaaagc aaaaggatga  26040
ataaagatat gtcatgctgg tgcaggtgtg gtgtggctca tgccttgtaa tcccagcact  26100
ttgggaggcc aagggggca gaccacttga ggtcaggagt tcaagatcag cctggccaac  26160
atggtgaaac cctgtctcta ctaaaaatac aaaaactagc tgggcgtggt ggcaggcgcc  26220
tgtaatccca gctattcggg aggctgaggt aggagaaccg cttgaaccca ggaggcagag  26280
gttgcagtaa gctgagattg caccaccgca ctccagccag ggcaacagag tgagactccg  26340
tctcaaaaaa aaaaaaaaaa aaaaaaaaga aaaaagaaaa agaaaagaag aacccaccca  26400
gctctaccat tactgtgata tctgaggctg gagaaaataa tgaaactgtc cagactatcc  26460
tcaagtttac agacagtgag aaatacccaa atgaagctcc tttttatgaa acattcttgg  26520
aaaatctaga agataatgtc tcagacattt aaaaattctt agcattacaa gctgaagaaa  26580
tcttggcatg gtgatgatct ttagtgacag ctgtgcaaga aaaattaaat gaaatggata  26640
```

-continued

```
aaaagcaaag ggaggaagac aatatctaga atataaaaga ctctttcaat cataataaaa  26700

agtcaatcca taatttgggc agaaacaatg taacgaggcg gtgaaac                26747
```

GROWTH FACTOR WHICH ACTS THROUGH ERBB-4 RTK

RELATED APPLICATIONS

This Application is a divisional of U.S. patent application Ser. No. 11/492,124, filed on Jul. 25, 2006, now abandoned, which is a divisional of U.S. patent application Ser. No. 10/240,411, filed on Oct. 1, 2002, now U.S. Pat. No. 7,094, 882, which is a National Phase Application of PCT Patent Application No. PCT/IL01/00371 having International Filing Date of Apr. 20, 2001, which is a continuation-in-part (CIP) of U.S. patent application Ser. No. 09/553,769, filed on Apr. 21, 2000, now U.S. Pat. No. 6,544,759.

The contents of the above Applications are all incorporated herein by reference.

FIELD AND BACKGROUND OF THE INVENTION

The present invention relates to a novel ErbB-4 ligand, referred to herein as Neuregulin-4 (NRG-4), to polynucleotide sequences encoding said NRG-4, to oligonucleotides and oligonucleotide analogs derived from said polynucleotide sequences, to a display library displaying short peptides derived from said NRG-4, to antibodies recognizing said NRG-4, to peptides or peptide analogs derived from said NRG-4, and to pharmaceutical compositions and methods of employing said peptides or peptide analogs, said oligonucleotides and oligonucleotide analogs, and/or said polynucleotide sequences to up-regulate or down-regulate ErbB-4 receptor activity and to treat or prevent various diseases, conditions and syndromes.

Cell-to-cell signaling is an essential feature of multi-cellular organisms, playing important roles in both the unfolding of developmental diversification as well as mediating the homeostasis of vastly different cell types. A large number of tyrosine kinase growth factor receptors play key roles in this process. Type-1 tyrosine kinase receptors, also known as ErbB/HER proteins, comprise one of the better-characterized families of growth factor receptors, of which the epidermal growth factor receptor (ErbB-1) is the prototype [reviewed in (Burden & Yarden, 1997)]. The ErbB family constitutes four known receptors which dimerize upon ligand stimulation, transducing their signals by subsequent autophosphorylation catalyzed by an intrinsic cytoplasmic tyrosine kinase, and recruiting downstream signaling cascades.

The ErbB receptors are activated by a large number of ligands. Depending upon the activating ligand, most homodimeric and heterodimeric ErbB combinations can be stabilized upon ligand binding (Tzahar et al., 1996), thus allowing a complex, diverse downstream signaling network to arise from these four receptors. The choice of dimerization partners for the different ErbB receptors, however, is not arbitrary.

Spatial and temporal expression of the different ErbB receptors do not always overlap in vivo, thus narrowing the spectrum of possible receptor combinations that an expressed ligand can activate for a given cell type (Erickson et al., 1997; Gassmann et al., 1995; Lee et al., 1995; Pinkas-Kramarski et al., 1997; Riethmacher et al., 1997).

Furthermore, a hierarchical preference for signaling through different ErbB receptor complexes takes place in a ligand-dependent manner. Of these, ErbB-2-containing combinations are often the most potent, exerting prolonged signaling through a number of ligands, likely due to an ErbB-2-mediated. deceleration of ligand dissociation (Karunagaran et al., 1996; Tzahar et al., 1996; Wang et al., 1998).

In contrast to possible homodimer formation of ErbB-1 and ErbB-4, for ErbB-2, which has no known direct ligand, and for ErbB-3, which lacks an intrinsic tyrosine kinase activity (Guy et al., 1994), homodimers either do not form or are inactive.

Heterodimeric ErbB complexes are arguably of importance in vivo. For example, mice defective in genes encoding either NRG-1, or the receptors ErbB-2 or ErbB-4, all result in identical failure of trabeculae formation in the embryonic heart, consistent with the notion that trabeculation requires activation of ErbB-2/ErbB-4 heterodimers by NRG-1 (Gassmann et al., 1995; Lee et al., 1995; Meyer & Birchmeier, 1995).

At the biochemical level, the known ErbB ligands fall into several categories (Riese et al., 1996b). One category, the ErbB-1 ligands, includes EGF, Transforming Growth Factor α (TGFα), Epiregulin, Amphiregulin, Betacellulin and the Heparin-binding EGF (HB-EGF) (Higashiyama et al., 1991; Marquardt et al., 1984; Shing et al., 1993; Shoyab et al., 1989; Toyoda et al., 1995). To different extents, these ErbB-1 binding ligands can also activate other receptors of the ErbB family, and hence may mediate distinct signaling outputs for a given cell type [reviewed in (Tzahar & Yarden, 1998)].

Another category of ErbB ligands comprises the Neuregulin (NRG) family. NRG-1 [also named Neu differentiation factor (NDF), Heregulin, Glial Growth factor, and Acetylcholine Receptor Inducing Activity] was first identified by its ability to indirectly phosphorylate ErbB-2 (Holmes et al., 1992; Peles et al., 1992; Wen et al., 1992). Subsequently, NRG-1 was found to directly bind ErbB-3 and ErbB-4 and to sequester ErbB-2 by receptor dimerization (Peles et al., 1993; Plowman et al., 1993; Sliwkowski et al., 1994; Tzahar et al., 1994). Multiple isoforms of NRG-1 exist which amongst other roles, permit heterogeneous binding affinities to different ErbB complexes (Tzahar et al., 1994). The NRG family now includes also two isoforms of NRG-2 (Busfield et al., 1997; Carraway et al., 1997; Chang et al., 1997; Higashiyama et al., 1997), of which the alpha isoform is a pan-ErbB ligand (Pinkas-Kramarski et al., 1998), and NRG-3, a ligand of ErbB-4 (Zhang et al., 1997).

The multiplicity of genes encoding ErbB-1 ligands, contrasting with the small number of known genes encoding ligands for ErbB-3 or ErbB-4 (namely: NRGs), led the inventors of the present invention to believe in the existence of additional NRG genes in the genome of mammals.

A fourth Neuregulin, denoted NRG-4, which acts through the ErbB-4 receptor tyrosine kinase is reported herein. In addition to its novel structure, this growth factor displays a pattern of expression different from other EGF-like molecules.

SUMMARY OF THE INVENTION

Thus, the ErbB/HER family of receptor tyrosine kinases include four receptors that bind a large number of growth factor ligands sharing an epidermal growth factor (EGF)-like motif. Whereas ErbB-1 binds seven different ligands whose prototype is EGF, the three families of Neuregulins (NRGs) bind ErbB-3 and/or ErbB-4. While reducing the present invention to practice a fourth neuregulin, NRG-4, that acts through ErbB-4, has been identified, isolated and characterized. The predicted pro-NRG-4 is a transmembrane protein carrying a unique EGF-like motif and a short cytoplasmic domain. A synthetic peptide encompassing the full-length EGF-like domain induces growth of interleukin-dependent cells ectopically expressing ErbB-4, but not cells expressing the other three ErbB proteins or their combinations. Consistent with specificity to ErbB-4, NRG-4 can displace an ErbB-4-bound NRG-1 and can activate signaling downstream of this receptor. Expression of NRG-4 mRNA was detected in the adult pancreas and weakly in muscle. The primary structure and the pattern of expression of NRG-4, together with the strict specificity of this growth factor to ErbB-4, suggest a physiological role distinct to that of the known ErbB ligands. This strict specificity of binding can be exploited in numerous biopharmaceutical purposes.

According to one aspect of the present invention there is provided an isolated nucleic acid comprising a genomic, complementary or composite polynucleotide sequence encoding a polypeptide being capable of binding to a mammalian ErbB-4 receptor and including a stretch of amino acids at least 95% homologous to a stretch of amino acids derived from SEQ ID NO:15 as determined using the BestFit software of the Wisconsin sequence analysis package, utilizing the Smith and Waterman algorithm, where gap creation penalty equals 8 and gap extension penalty equals 2.

According to another aspect the polynucleotide encodes a polypeptide which is at least 50% homologous to at least positions 4-50 of SEQ ID NOs:2 or 15 as determined using the BestFit software of the Wisconsin sequence analysis package, utilizing the Smith and Waterman algorithm; where gap creation penalty equals 8 and gap extension penalty equals 2.

According to preferred embodiments, the polynucleotide according to this aspect of the present invention encodes a polypeptide as set forth in SEQ ID NOs:2 or 15 or a portion thereof, preferably a portion which retains the binding activity.

According to still preferred embodiments, the polynucleotide according to this aspect of the present invention includes a polynucleotide stretch at least 80% identical to positions 55-190 of SEQ ID NO:14 as determined using the BestFit software of the Wisconsin sequence analysis package, utilizing the Smith and Waterman algorithm, where gap weight equals 50, length weight equals 3, average match equals 10 and average mismatch equals −9.

Alternatively or additionally, the polynucleotide according to this aspect of the present invention is preferably hybridizable with SEQ ID NOs:1 or 14.

Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and $5\times10^6$ $cpm^{32}p$ labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and $5\times10^6$ $cpm^{32}p$ labeled probe, at 65° C., with a final wash solution of 1×SSC and 0.1% SDS and final wash at 50° C.

Yet alternatively or additionally, the polynucleotide according to this aspect of the present invention is preferably at least 50% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to preferred embodiments the polynucleotide according to this aspect of the present invention is as set forth in SEQ ID NOs:1 or 14 or a portion thereof, the portion preferably encodes a polypeptide retaining the binding activity.

According to another aspect of the present invention there is provided a nucleic acid construct comprising the isolated nucleic acid described herein.

According to a preferred embodiment the nucleic acid construct according to this aspect of the present invention further comprising a promoter for regulating expression of the isolated nucleic acid in a sense or antisense orientation.

Alternatively, the nucleic acid construct according to this aspect of the present invention further comprising a positive and a negative selection markers and may therefore be employed for selecting homologous recombination events, including, but not limited to, homologous recombination employed in knock-in and knock-out procedures.

Consequently, according to yet another aspect of the present invention there is provided a host cell or animal comprising a nucleic acid construct as described herein.

According to still another aspect of the present invention there is provided an oligonucleotide of at least 17 bases specifically hybridizable with the isolated nucleic acid described herein.

Hybridization of shorter nucleic acids (below 200 bp in length, e.g. 17-40 bp in length) is effected by stringent, moderate or mild hybridization, wherein stringent hybridization is effected by a hybridization solution of 6.times.SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1-1.5° C. below the Tm, final wash solution of 3 M TMACI, 0.01 M sodium phosphate (pH 6.8), 1 mM EDTA (pH 7.6), 0.5% SDS at 1-1.5° C. below the $T_m$; moderate hybridization is effected by a hybridization solution of 6×SSC and 0.1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2-2.5° C. below the $T_m$, final wash solution of 3 M TMACI, 0.01 M sodium phosphate (pH 6.8), 1 mM EDTA (pH 7.6), 0.5% SDS at 1-1.5° C. below the $T_m$, final wash solution of 6×SSC, and final wash at 22° C.; whereas mild hybridization is effected by a hybridization solution of a hybridization solution of 6.times.SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each of at least 17 bases specifically hybridizable with the isolated nucleic acid described herein in an opposite orientation so as to direct exponential amplification of a portion thereof in a nucleic acid amplification reaction.

According to yet an additional aspect of the present invention there is provided a nucleic acid amplification product obtained using the pair of primers described herein.

According to still an additional aspect of the present invention there is provided an antisense oligonucleotide comprising a polynucleotide or a polynucleotide analog of at least 10 bases being hybridizable in vivo, under physiological conditions, with a portion of a polynucleotide strand encoding a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to a further aspect of the present invention there is provided a pharmaceutical composition comprising the antisense oligonucleotide described herein and a pharmaceutically acceptable carrier.

According to still a further aspect of the present invention there is provided a ribozyme comprising the antisense oligonucleotide described herein and a ribozyme sequence fused thereto.

According to yet a further aspect of the present invention there is provided a recombinant or synthetic protein comprising a polypeptide being capable of binding to a mammalian ErbB-4 receptor and including a stretch of amino acids at least 95% homologous to a stretch of amino acids derived from SEQ ID NO:15 as determined using the BestFit software of the Wisconsin sequence analysis package, utilizing the Smith and Waterman algorithm, where gap creation penalty equals 8 and gap extension penalty equals 2. Most preferably the polypeptide includes at least a portion of SEQ ID NOs:2 or 15. Additionally or alternatively, the polypeptide according to this aspect of the present invention is preferably encoded by a polynucleotide hybridizable with SEQ ID NOs:1 or 14 or a portion thereof under any of the stringent or moderate hybridization conditions described above for long nucleic acids. Still additionally or alternatively, the polypeptide according to this aspect of the present invention is preferably encoded by a polynucleotide at least 50% identical with SEQ ID NOs:1 or 14 or portions thereof as determined using the BestFit software of the Wisconsin sequence analysis package, utilizing the Smith and Waterman algorithm, where gap weight equals 50, length weight equals 3, average match equals 10 and average mismatch equals −9.

According to still a further aspect of the present invention there is provided a pharmaceutical composition comprising, as an active ingredient, the recombinant protein described herein and a pharmaceutical acceptable carrier.

According to another aspect of the present invention there is provided a peptide or a peptide analog comprising a stretch of at least 6 consecutive amino acids or analogs thereof derived from a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2. Preferably, the peptide or a peptide analog according to this aspect of the present invention comprises a stretch of at least 6 consecutive amino acids or analogs thereof derived from SEQ ID NOs;2 or 15.

According to still another aspect of the present invention there is provided a display library comprising a plurality of display vehicles (such as phages, viruses or bacteria) each displaying at least 6 consecutive amino acids derived from a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention substantially every 6 consecutive amino acids derived from the polypeptide are displayed by at least one of the plurality of display vehicles, so as to provide a highly representative library. Preferably, the consecutive amino acids or amino acid analogs of the peptide or peptide analog according to this aspect of the present invention are derived from SEQ ID NOs:2 or 15.

According to still another aspect of the present invention there is provided an antibody comprising an immunoglobulin specifically recognizing a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention the antibody specifically recognizing the polypeptides set forth in SEQ ID NOs:2 or 15. The antibody according to this aspect of the present invention can be, for example, a polyclonal antibody, a monoclonal antibody, a humanized antibody, a single chain antibody or an immunoreactive derivative (e.g., portion) of an antibody.

According to yet another aspect of the present invention there is provided a pharmaceutical composition comprising, as an active ingredient, an agent for regulating an endogenous protein affecting ErbB-4 activity, the endogenous protein being at least 50% homologous to at least positions 4-50 of SEQ ID NOs:1 or 15 as determined using the BestFit software of the Wisconsin sequence analysis package, utilizing the Smith and Waterman algorithm, where gap creation penalty equals 8 and gap extension penalty equals 2.

According to still another aspect of the present invention there is provided a method of treating or preventing a disease, condition or syndrome associated with disregulation of an endogenous protein affecting ErbB-4 receptor activity, the method comprising administering a therapeutically effective amount of an agent for regulating an endogenous protein affecting ErbB-4 receptor activity, the endogenous protein being at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to yet another aspect of the present invention there is provided a method of regulating an endogenous protein activity affecting ErbB-4 activity the method comprising the steps of administering an agent for regulating the endogenous protein activity, the endogenous protein being at least 50% homologous to at least positions 4-50 of SEQ ID NOs:1 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent serves for altering, e.g., upregulating, the activity.

According to still further features in the described preferred embodiments the agent includes an expressible sense polynucleotide at least 50% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the agent includes a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent serves for downregulating the activity.

According to still further features in the described preferred embodiments the agent is an immunoadhesin, the immunoadhesin comprises a first polypeptide being at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2, fused to an immunogolbulin.

According to still further features in the described preferred embodiments the immunoglobulin is selected from the group consisting of IgG-1, IgG-2, IgG-3, IgA and IgM.

According to still further features in the described preferred embodiments the agent includes an expressible antisense polynucleotide at least 50% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the agent includes an antisense oligonucleotide which includes a polynucleotide or a polynucleotide analog of at least 10 bases which is hybridizable in vivo, under physiological conditions, with a portion of a polynucleotide strand encoding a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent includes a peptide or a peptide analog representing a stretch of at least 6 consecutive amino acids or analogs thereof derived from a polypeptide at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

According to still further features in the described preferred embodiments the disease, condition or syndrome is selected from the group consisting of amyotrophic lateral sclerosis (Lou Gehrig's disease), Bell's palsy, spinal muscular atrophy, brain trauma, brain surgery, stroke, brain injury, ischemia, brain and neck malignancies, central nervous system nutritional deficiency, Alzheimer's disease, Parkinson's disease, epilepsy, multiple sclerosis, Huntington's chorea, Down's syndrome, nerve deafness, Meniere's disease, neuropathy, peripheral neuropathy, hereditary neuropathy, muscular dystrophy, extramammary Paget's disease, gastric cancer, pancreatic cancer, prostate cancer, breast cancer, ovarian cancer, cervical carcinoma, endometrial adenocarcinoma, pancreatic D cells-somatostatinoma and Zollinger-Ellison syndrome.

According to still further features in the described preferred embodiments the agent includes a polypeptide capable of binding the endogenous protein affecting ErbB-4 receptor activity.

According to still further features in the described preferred embodiments the polypeptide is a soluble ligand binding domain of ErbB-4.

According to still further features in the described preferred embodiments the soluble ligand binding domain of ErbB-4 is IgB4.

According to still further features in the described preferred embodiments pharmaceutical acceptable carrier is a semipermeable, implantable membrane device.

According to still further features in the described preferred embodiments the semipermeable, implantable membrane device is used to secrete the agent.

According to another aspect of the present invention there is provided a method of diagnosing a disease, condition or syndrome associated with disregulation of an endogenous protein affecting ErbB-4 receptor activity, the endogenous protein being at least 50% homologous to at least positions 4-50 of SEQ ID Nos:2 or 15 as determined using the BestFit software of the Wisconsin sequence analysis package, utilizing the Smith and Waterman algorithm, where gap creation penalty equals 8 and gap extension penalty equals 2, the method comprising (a) obtaining a sample from a subject; (b) incubating the sample with a polypeptide capable of binding the endogenous protein for a time period sufficient for forming a complex; and (c) monitoring a level of the complex, to thereby diagnose the disease, condition or syndrome associated with the disregulation of the endogenous protein affecting ErbB-4 receptor activity.

According to yet another aspect of the present invention there is provided a method of diagnosing a disease, condition or syndrome associated with disregulation of an endogenous protein affecting ErbB-4 receptor activity, the endogenous protein being at least 50% homologous to at least positions 4-50 of SEQ ID Nos:2 or 15 as determined using the BestFit software of the Wisconsin sequence analysis package, utilizing the Smith and Waterman algorithm, where gap creation penalty equals 8 and gap extension penalty equals 2, the method comprising (a) obtaining a sample from a subject; and (b) incubating the sample with at least one oligonucleotide or oligonucleotide analog of at least 17 bases, the oligonucleotide or oligonucleotide analog capable of hybridizing to a portion of a polynucleotide strand encoding the endogenous protein, to thereby diagnosing the disease, condition or syndrome associated with disregulation of an endogenous protein affecting ErbB-4 receptor activity.

According to still further features in the described preferred embodiments the at least one oligonucleotide or oligonucleotide analog comprises a pair of oligonucleotides or analogs specifically hybridizable to the portion of the polynucleotide strand in an opposite orientation so as to direct exponential amplification of at least a portion thereof in a nucleic acid amplification reaction.

According to yet another aspect of the present invention there is provided a method of determining a distribution of ErbB-4 receptor in a biological sample, the method comprising incubating the biological sample with a labeled polypeptide, the polypeptide being at least 50% homologous to at least positions 4-50 of SEQ ID NOs:2 or 15 as determined using BestFit software of the Wisconsin sequence analysis package, utilizing the Smith and Waterman algorithm, where the gap creation penalty equals 8 and gap extension penalty equals 2, to thereby determine the distribution of ErbB-4 receptor in the biological sample.

According to still another aspect of the present invention there is provided a method of testing whether a genetic disease mapped to 15q25-26 is associated with NRG-4, the method comprising determining the presence or absence of sequence differences between individuals carrying at least one allele causing the genetic disease and individuals free of the allele, wherein presence of the sequence differences is indicative that the genetic disease mapped to 15q25-26 is associated with NRG4.

The present invention successfully addresses the shortcomings of the presently known configurations by disclosing a novel Neuregulin which specifically binds ErbB-4 with somewhat lower affinity as is compared to, for example, NRG-1β. Additional advantages, novel features and utilities of the various aspects of the present invention are described in the following sections of this application.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1*a* shows the nucleotide sequence (SEQ ID NO:1) and deduced amino acid sequence (SEQ ID NO: 2) of mouse pro-NRG-4. Nucleotides are numbered at the left-hand column and amino acids at the right hand column. The EGF-like domain with its six cysteine residues is shown in bold type, and potential N-glycosylation sites are underlined. The filled box underlines the predicted transmembrane amino acid sequence.

FIG. 1*b* shows the hydropathy profile of mouse pro-NRG-4. The method of Kyte and Doolittle (Kyte & Doolittle, 1982) was used with a window of 11 residues. Positive values indicate increasing hydrophobicity. Amino acid numbers are indicated below the profile. The putative transmembrane stretch of the pro-NRG-4 is marked. Note the absence of a recognizable signal peptide at the N-terminus.

FIG. 1*c* shows alignment of mouse amino acid sequence of the EGF-like domain of NRG-4 with the EGF-like motifs of other growth factors (SEQ ID NOs:3-13 as indicated in the Figure). Canonical residues are boxed in black. Other identities with NRG-4 are shaded in gray. The predicted three disulfide bonds of the motifs (Cys 1-3, Cys 2-4, and Cys 5-6) are shown above the alignment and labeled as loops A, B and C. The abbreviations used are as follows: NRG, Neuregulin; TGFα, Transforming Growth Factor α; HB-EGF, Heparin-Binding EGF-like Growth Factor. If not specified, the species of origin of all ligands is murine, except NRG-1β (rat). For alignment, the FastA (Pearson and Lipman) search was employed with the following search parameters, word size of 2, Scoring matrix-blosum 50, Variable pamfactor used-Gap creation penalty: 12, Gap extension penalty: 2, Joining threshold: 36, opt. threshold: 24, and opt. width: 16.

FIG. 1*e* shows the nucleotide sequence (SEQ ID NO:14) and deduced amino acid sequence (SEQ ID NO:15) of human NRG-4 and its comparison with the nucleotide sequence (SEQ ID NO:1) and deduced amino acid sequence (SEQ ID NO:2) of mouse NRG-4. Human NRG-4, derived from T47D cells was sequenced from two independent RT-PCR reactions and compared to the mouse sequence. The predicted EGF-encoding domains and transmembrane domains are marked in bold and are underlined respectively. Shaded boxes indicate protein sequence identity. The predicted translation products share 78% overall identity and 91% sequence identity within the EGF-like encoding domain.

DESCRIPTION OF THE PREFERRED EMBODIMENTS

Figure 1D:
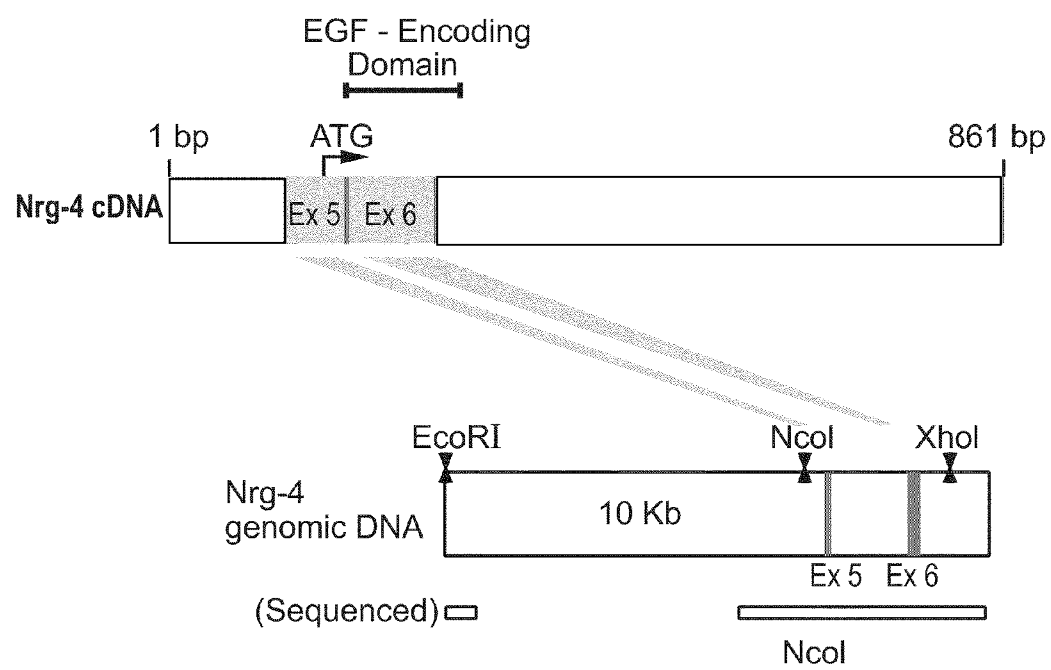
FIG. 1*d* shows the mouse NRG-4 gene structure. The mouse genomic NRG-4 was isolated from a PBAC library using the EGF-encoding domain as a probe. An EcoR1 digested subclone is depicted, with sequenced regions underlined in shade. Two exons found in the genomic sequence were arbitrarily designated as Exons 5 and 6 (Ex 5 & Ex 6), in accordance with the prototypical NRG-1 genetic structure, in which the invariant component of the EGF-domain is also designated as "Exon 6" (Ex 6). The intron-exon boundaries of Ex 6 for both NRG-1 and NRG-4 are identical, supporting the idea that these genes are derived from a common ancestor, and further supports that NRG-4 is a novel variant of the Neuregulin gene family.

The present invention is of (i) a novel Neuregulin which is referred to herein as NRG-4; (ii) polynucleotide sequences encoding NRG-4; (iii) oligonucleotides and oligonucleotide analogs derived from said polynucleotide sequences; (iv) a display library displaying short peptides derived from said NRG-4; (v) antibodies recognizing said NRG-4; (vi) peptides or peptide analogs derived from said NRG-4; and (vii) pharmaceutical compositions; and (viii) methods of employing said peptides or peptide analogs, said oligonucleotides and oligonucleotide analogs, and/or said polynucleotide sequences to up-regulate or down-regulate ErbB-4 activity and to treat or prevent various diseases, conditions and syndroms.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or exemplified in the Examples section that follows. The invention is capable of other embodiments or of being practiced or carried out in various ways. Also, it is to be understood that the phraseology and terminology employed herein is for the purpose of description and should not be regarded as limiting.

While conceiving the present invention it was hypothesized that additional, yet unknown, ErbB tyrosine kinase receptor ligands may exist. Screening an EST database with the motif $CX_7CXNGGXCX_{13}CXCX_3YXGXRC$ (SEQ ID NO:18), which is conserved in most ErbB-ligand isoforms, revealed (i) an EST clone originating from a mouse liver cDNA library (accession number AA238077) encoding an EGF-like domain sharing 32% identity with the NRG-1β isoform (Wen et al., 1992); and (ii) a human derived EST clone (accession No. AI743118) having an EGF-like domain disrupted by an insert.

While reducing the present invention to practice these clones have been characterized as encoding yet unknown ligands of the EGF/NRG family, which was referred to as Neuregulin-4 (NRG-4). The NRG-4 was mapped to the 15q25-26 locus. Aside from NRG-4 possessing a Neuregulin-like EGF domain (FIG. 1*c*), it shares very little other sequence homology to the known NRGs (NRG-1 through 3), particularly in the vicinity of the transmembrane domain, a region where the other three NRGs exhibit high primary sequence homology. However, the presumed precursor form of NRG-4 shares several structural characteristics with other mammalian ErbB ligands [which are reviewed in (Massague & Pandiella, 1993)], including a transmembrane topology, a juxtamembrane location of the EGF-like domain, and a putative proteolytic cleavage site located at a serine-rich region C-terminally to the EGF-like domain. This region may serve as a site of O-glycosylation, in addition to two potential sites of N-glycosylation located in the presumed ectodomain of NRG-4. Like other NRGs, but unlike most ErbB-1-specific ligands, NRG-4 lacks an N-terminally located hydrophobic signal peptide. However, the absence of a characteristic sequence may not exclude the possibility that NRG-4 acts as a secreted growth factor, because other signal peptide-less growth factors can be secreted or released from producer cells through alternative secretory mechanisms or upon cell lysis. NRG-4 presents a rather unique case as it also lacks an apolar stretch of amino acids that usually replaces a signal peptide (e.g., in NRG-1). In fact, the presumed ectodomain of NRG-4 is the shortest among NRG/EGF family members. In addition, unlike other NRGs, which contain a variety of structural motifs, such as an immunoglobulin-like domain, a cysteine-rich region, or a mucin-like domain, NRG-4 contains no recognizable structural motif other than the EGF-like domain.

Interspecies conservation of NRG-4 was identified by comparison between human and mouse NRG-4 amino acid sequences. The human and mouse sequences share 78% overall identity and 91% sequence identity within the EGF domain, demonstrating that NRG-4 is expressed amongst mammals and the high interspecies homology particularly within the EGF-domain indicates an important physiological role for this gene.

The prototypical NRG-1 gene encodes a large number of isoforms (Baruch & Yarden, 1994). However the ErbB-binding moiety of NRG-1 is defined by the EGF-encoding domain, of which there are only two variants (alpha and beta). The two NRG-1 EGF-domain encoded variants share an invariant $NH_3$ component encoded by Exon 6 and two alternative COOH-termini generated by subsequent alternative exon splicing. By analogy, the mouse NRG-4 genomic locus shares the same genomic exon-intron structure spanning Exon-6. This finding not only supports that NRG-4 is ancestrally related to NRG-1, it also strengthens the suspicion that the NRG-4 locus may encode many isoforms, including perhaps two variants of the EGF-like domain. Indeed, Northern Blot analysis revealed the presence of distinctive bands hybridizing to NRG-4, demonstrating that isoforms of differing size are likely to exist. Many or all of these isoforms will harbor the EGF-domain reported in this study and will elicit the identical ErbB-binding moieties as that for this novel ligand.

Figure 3A:
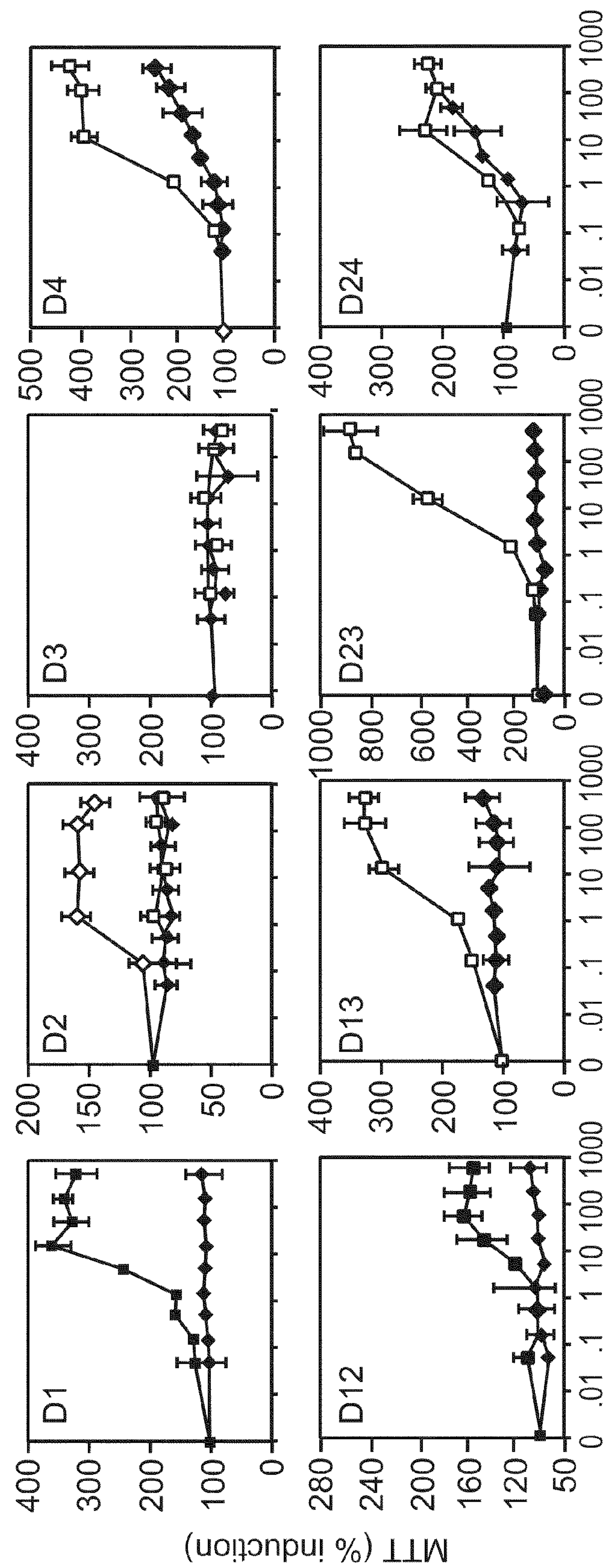
FIG. 3*a* shows proliferative effect of NRG-4 on ErbB-expressing derivatives of 32D cells. The indicated derivative lines of 32D cells were tested for cell proliferation using the [3-(4,5-dimethylthiazol-2-yl)-2,5-diphenyl]tetrazolium bromide (MTT) assay. Cells were deprived of serum factors and IL-3 and then plated at a density of $5\times10^5$ cells/ml in media containing serial dilutions of NRG-4 (closed diamonds), EGF (closed squares), NRG-1β (open squares), or the L96 (maximal dose: 50 μg/ml) anti-ErbB-2 monoclonal antibody (open diamonds). The MT assay was performed 24 hours later. Results are presented as percent induction over the control untreated cells, and are the mean±S.D. of 4 determinations. Each experiment was repeated at least twice with similar findings. Note that no responses to EGF-like ligands were observed with cells expressing either ErbB-2 or ErbB-3 alone, but these cell derivatives retained response to IL-3 (data not shown).
Figure 3B:
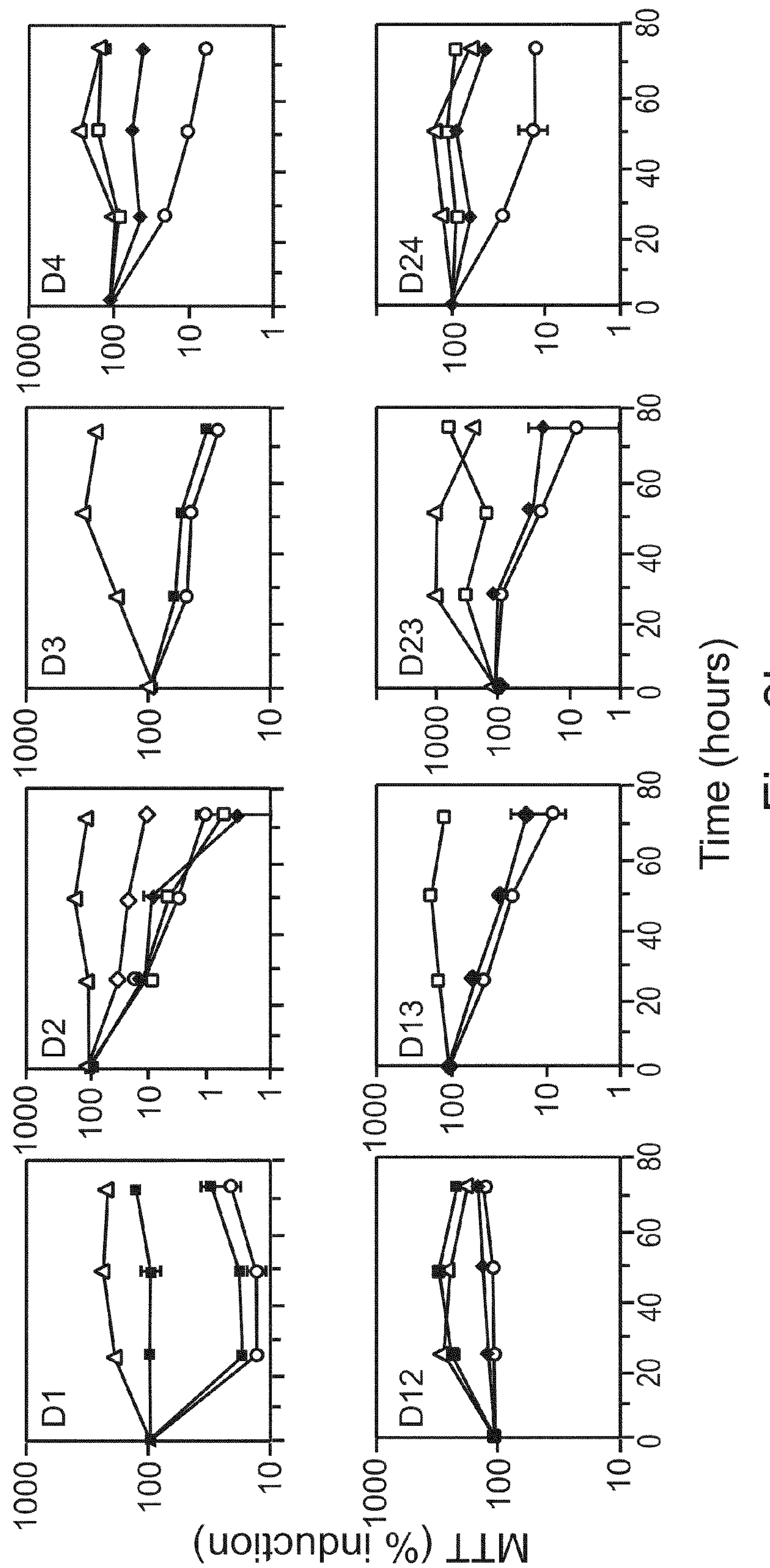
FIG. 3*b* show survival effect of NRG-4 on ErbB-expressing derivatives of 32D cells. The indicated derivatives of 32D cells were incubated for various time intervals in the absence of IL-3. The following ligands, each at a concentration of 100 ng/ml, were incubated with cells: NRG-4 (closed diamonds), EGF (closed squares), NRG-1β (open squares), or 50±μg/ml mAb L96 (open diamonds). For control, cells were incubated with medium conditioned by IL-3-producing cells (open triangles), or with no factor (open circles). The extent of cell proliferation was determined daily by using the calorimetric MTT assay. The data presented are the mean±S.D. of 4 determinations. Note that co-expression of ErbB-1 and ErbB-2 (D12 cells) enabled cell survival in the absence of IL-3. The experiment was repeated twice with similar results.
Figure 4A:
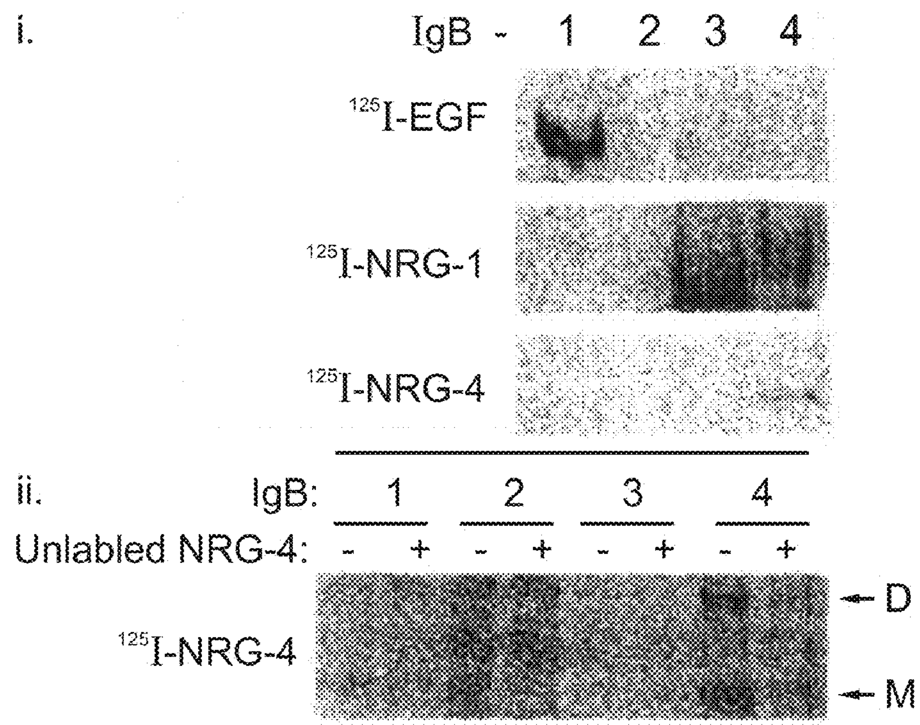
FIG. 4*a* shows covalent crosslinking of NRG-4 to recombinant-soluble ErbB proteins. The four soluble forms of ErbB proteins, in the form of IgG fusions (denoted IgB-1 through 4), were separately incubated with the indicated radiolabeled growth factors. Where indicated (lower panel), an excess (100-fold) of unlabeled NRG-4 was co-incubated with the labeled ligand. Following 2 hours at 22° C., the covalent crosslinking reagent bis(sulfosuccinimdyl)-suberate ($BS^3$) was added (1 mM) and 45 minutes later the ligand-receptor complexes were immunoprecipitated with agarose-immobilized protein-A beads. Arrows mark the locations of monomeric (M) and dimeric (D) receptor complexes.
Figure 4B:
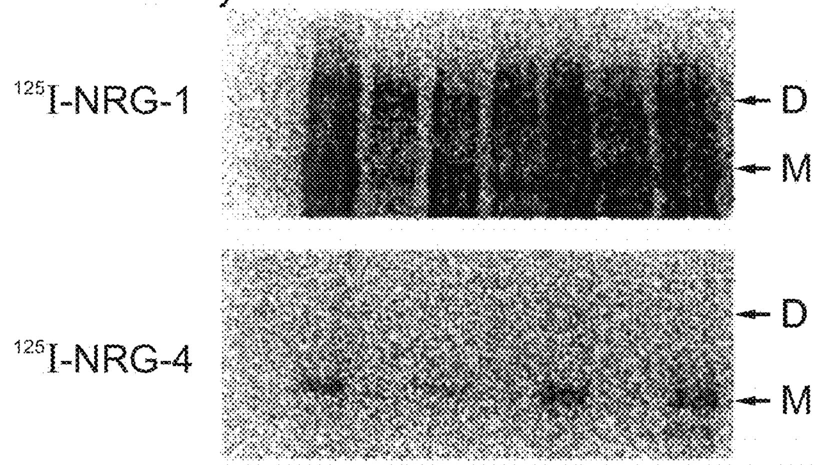
FIG. 4*b* shows covalent crosslinking of NRG-4 to cell surface-expressed ErbB proteins. CHO cells were transfected with vectors directing expression of the indicated ErbB proteins or their combinations. Two days later cell monolayers were incubated with either $^{125}$I-NRG-1β or $^{125}$I-NRG-4 (EGF-like domains, each at 100 ng/ml). Following 2 hours at 4° C., the covalent crosslinking reagent bis(sulfosuccinimdyl)-suberate ($BS^3$) was added (1 mM final concentration) and cell extracts prepared after an additional 45 minutes of incubation. The indicated ErbB proteins were then immunoprecipitated with mouse monoclonal antibodies, and the complexes resolved by gel electrophoresis and autoradiography. Arrows mark the locations of monomeric (M) and dimeric (D) receptor complexes.
Figure 4C:
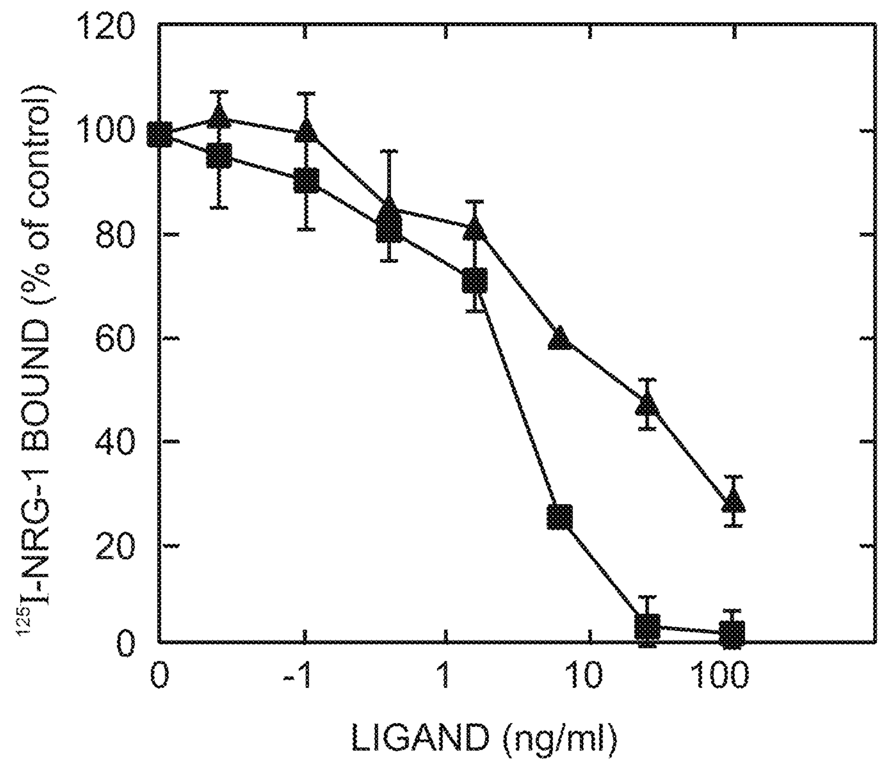
FIG. 4*c* shows binding of NRG-4 to ErbB-4-expressing cells. Displacement analyses of radiolabeled NRG-1β were performed with CHO cells expressing ErbB-4. Cell monolayers ($2\times10^5$ cells) were incubated for 2 hours at 4° C. with a radiolabeled NRG-1 (5 ng/ml) in the presence of increasing concentrations of an unlabeled NRG-4 (closed triangles), or NRG-1β (closed squares). Each data point represents the mean and range (bars) of two determinations.
Figure 5:
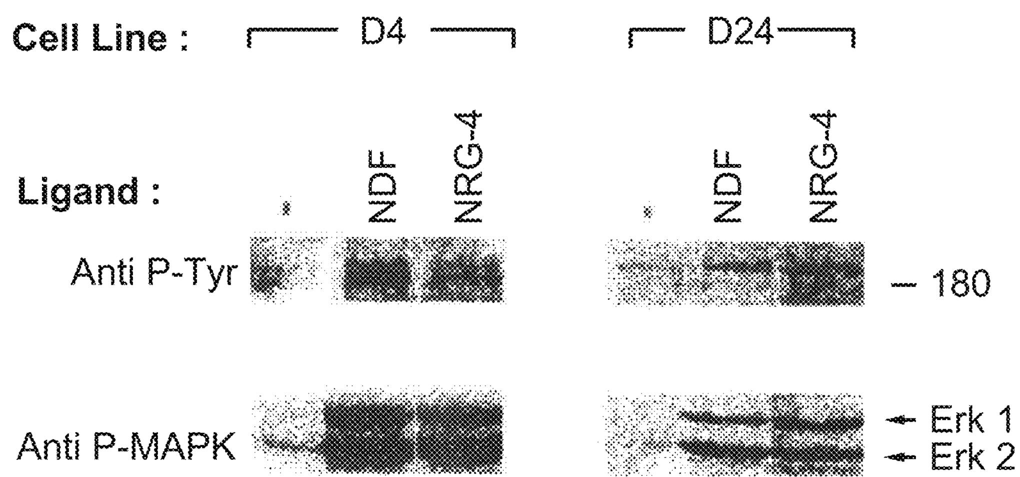
FIG. 5 shows tyrosine phosphorylation and MAPK activation by NRG-4. Derivatives of 32D cells expressing ErbB-4, either alone (D4 cells) or in combination with ErbB-2 (D24 cells) were incubated for 5 minutes at 37° C. with either NRG-4 or NRG-1β (each at 100 ng/ml). Whole cell extracts were then prepared, resolved by gel electrophoresis, and transferred to a nitrocellulose filter. The upper portion of the filter was immunoblotted with antibodies to phosphotyrosine (P-Tyr, the 150-200 kDa region is shown) or an antibody directed at the activated doubly phosphorylated form of the MAPK (Erk1 and Erk2, the 40-50 kDa region is shown). Antibodies were incubated with a secondary reagent coupled to horseradish peroxidase, allowing subsequent detection by chemiluminescence.

That the EGF-like domain of NRG-4 functions as a receptor-binding moiety is indicated by in vitro studies with engineered cell lines expressing all four ErbB proteins (e.g., FIGS. 3 to 5). The EGF-like domain of NRG-4 exhibits restricted binding specificity; it directly binds to ErbB-4, but not to ErbB-1, ErbB-2 or ErbB-3. A similar selective binding to ErbB-4 has also been reported for NRG-3 (Zhang et al., 1997) and may indicate that during development and in the adult, ligands with restricted ErbB specificities may play important roles. It is interesting to note that NRG-3 is the EGF-like ligand closest to NRG-4 (42% sequence identity in the EGF-like domain). Also relevant is the emerging wider repertoire of ErbB-4-specific ligands, as compared with growth factors that bind to ErbB-3. In addition to NRG-1, NRG-2, and NRG-3, ErbB-4 also binds to betacellulin (Riese et al., 1996a), epiregulin (Shelly et al., 1998) and HB-EGF (Elenius et al., 1997). Moreover, at high ligand concentrations, or in the presence of a co-expressed ErbB-2, ErbB-4 also binds EGF and TGFα (Shelly et al., 1998; Wang et al., 1998). The broader specificity of ErbB-4 was reflected also in mutagenesis experiments: more NRG-1 mutants displayed greater affinity loss for ErbB-3 compared with ErbB-4 (Jones et al., 1998).

Besides specificity to ErbB-4, NRG-3 and NRG-4 share relatively low affinity to this receptor compared with NRG-1 FIG. 4, and (Zhang et al., 1997)]. Several other ligands, such as epiregulin (Shelly et al., 1998) and the alpha isoform of NRG-1 (Tzahar et al., 1994), also display relatively low affinity to ErbB-4. These observations may suggest the existence of additional, yet undiscovered ErbB proteins, serving as high affinity receptors for these low affinity ligands. Alternatively, low affinity ligands may have a different biological function than high affinity growth factors, as they can escape the common rapid endocytic clearance from the extracellular space (Reddy et al., 1996; Shelly et al., 1998). Alternatively, the ligand-less co-receptor of ErbB-4, namely ErbB-2 (Karunagaran et al., 1996), may be more effective in the case of low affinity ligands, such as NRG-3 and NRG-4, thus offering a mechanism for fine-tuning of ErbB signaling. The interaction of ErbB ligands with ErbB-2 appears to involve direct binding to an ErbB-2 promiscuous binding site (Klapper et al., 1997; Tzahar et al., 1997). According to this model, all EGF-like growth factors are bivalent ligands, that differ in their binding specificity to specific pairs of ErbB receptors (Tzahar et al., 1997). This hypothesis may explain the multiplicity of ErbB ligands in terms of their differential ability to stabilize homo- and hetero-dimeric ErbB proteins. When applied to NRG-4, the bivalence model predicts that this ligand may differ from other ErbB-4-specific ligands, including NRG-3, in the ability to recruit heterodimer partners to ErbB-4.

Consistent with this model, it was demonstrated that when co-expressed with ErbB-4, NRG-4 can recruit both ErbB-1 and ErbB-2 into heterodimers (FIG. 4*b*). These NRG-4-induced heterodimeric complexes may be of physiological importance, as indicated in proliferation assays: NRG-4 weakly stimulated the growth of myeloid cells engineered to express ErbB-4 alone (D4 cells). In contrast, this response was significantly enhanced upon ErbB-2 co-expression (D24 cells, FIGS. 3*a-b*) when compared to that of the internal NRG-1 control. This finding may indicate that under some physiological conditions, the expression of ErbB-4 alone may be insufficient to elicit a biological response to NRG-4, requiring a co-receptor such as ErbB-2 to transduce its signal. This scenario has a precedence in the case of NRG-1: in vitro experiments showed clear enhancement of an ErbB-4-mediated mitogenic effect by a co-expressed ErbB-2 (Wang et al., 1998), and gene-targeting in mice indicated that ErbB-2 is essential for cardiac trabeculation that is mediated by NRG-1 and ErbB-4 (Lee et al., 1995).

With the exception of EGF, which is found in high concentrations in body fluids such as milk, urine and saliva (Carpenter & Cohen, 1979; Gregory et al., 1979), all of the EGF/NRG family members are thought to act as short-range ligands affecting only neighboring cells through paracrine or autocrine loops [reviewed in (Ben-Baruch et al., 1998)]. Consistent with short-range ligand-receptor interactions, NRG-3 is expressed primarily in the central nervous system, along with its only known receptor, ErbB-4 (Plowman et al., 1993; Zhang et al., 1997). However, ErbB-4 is expressed also in muscle, heart, pancreas, salivary gland and lung (Gassmann et al., 1995; Pinkas-Kramarski et al., 1997; Plowman et al., 1993). A Northern blot analysis (FIG. 2) demonstrated that in the adult, two of these ErbB-4-positive tissues, pancreas and muscle, express three molecular weight mRNA species of NRG-4. Likewise, multiple mRNA species of NRG-1 and NRG-2 were reported (Chan et al., 1995; Wen et al., 1992). It is know in this respect that many isoforms of NRG-1 and NRG-2 (Busfield et al., 1997; Carraway et al., 1997; Chang et al., 1997; Marchionni et al., 1993; Wen et al., 1994) are derived from multiplicity of alternatively spliced NRGs mRNAs.

Thus, according to one aspect of the present invention there is provided an isolated nucleic acid comprising a genomic, complementary or composite polynucleotide sequence encoding a polypeptide being capable of binding to a mammalian ErbB-4 receptor which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% homologous (similar+identical acids) to SEQ ID NOs:2 or 15 as determined using the BestFit software of the Wisconsin sequence analysis package, utilizing the Smith and Waterman algorithm, where gap creation penalty equals 8 and gap extension penalty equals 2. Preferably, the polypeptide being capable of binding to a mammalian ErbB-4 receptor according to the present invention includes a stretch of amino acids at least 90%, at least 91%, at least 92%, at least 93%, at least 94%, at least 95%, at least 96%, at least 97%, at least 98%, at least 99% or 100% homologous to a stretch of amino acids derived from SEQ ID NO:15 (e.g., amino acids 4-50 which form the EGF-like domain) as determined using the BestFit software of the Wisconsin sequence analysis package, utilizing the Smith and Waterman algorithm, where gap creation penalty equals 8 and gap extension penalty equals 2.

As used herein in the specification and in the claims section that follows, the phrase "complementary polynucleotide sequence" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein in the specification and in the claims section that follows, the phrase "genomic polynucleotide sequence" includes sequences which originally derive from a chromosome and reflect a contiguous portion of a chromosome.

As used herein in the specification and in the claims section that follows, the phrase "composite polynucleotide sequence" includes sequences which are at least partially complementary and at least partially genomic. A composite sequence can include some exonal sequences required to encode a polypeptide, as well as some intronic sequences interposing therebetween. The intronic sequences can be of any source, including of other genes, and typically will include conserved splicing signal sequences. Such intronic sequences may further include cis acting expression regulatory elements.

According to preferred embodiments, the polynucleotide according to this aspect of the present invention encodes a polypeptide as set forth in SEQ ID NOs:2 or 15 or a portion thereof, preferably a portion which retains binding to ErbB-4 receptor, e.g., amino acids 4-50 or a portion of at least 20 amino acids derived therefrom.

In a preferred embodiment the polynucleotide according to this aspect of the present invention includes a polynucleotide stretch at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to positions 55-190 of SEQ ID NO:14 as determined using the BestFit software of the Wisconsin sequence analysis package, utilizing the Smith and Waterman algorithm, where gap weight equals 50, length weight equals 3, average match equals 10 and average mismatch equals −9.

Alternatively or additionally, the polynucleotide according to this aspect of the present invention is preferably hybridizable with SEQ ID NOs: 1 or 14.

Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and 5.times.10.sup.6 cpm .sup.32p labeled probe, at 65° C., with a final wash solution of 0.2.times.SSC and 0.1% SDS and final wash at 65° C.; whereas moderate hybridization is effected by a hybridization solution containing 10% dextrane sulfate, 1 M NaCl, 1% SDS and $5\times10^6$ cpm $^{32}$p labeled probe, at 65° C., with a final wash solution of 1×SSC and 0.1% SDS and final wash at 50° C.

Yet alternatively or additionally, the polynucleotide according to this aspect of the present invention is preferably at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100%, identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

According to preferred embodiments the polynucleotide according to this aspect of the present invention is as set forth in SEQ ID NOs:1 or 14 or a portion thereof, said portion preferably encodes a polypeptide retaining the binding activity to ErbB-4.

Thus, this aspect of the present invention encompasses (i) polynucleotides as set forth in SEQ ID NOs:1 or 14; (ii) fragments thereof; (iii) sequences hybridizable therewith; (iv) sequences homologous thereto; (v) sequences encoding similar polypeptides with different codon usage; (vi) altered sequences characterized by mutations, such as deletion, insertion or substitution of one or more nucleotides, either naturally occurring or man induced, either randomly or in a targeted fashion.

According to another aspect of the present invention there is provided a nucleic acid construct comprising the isolated nucleic acid described herein.

According to a preferred embodiment the nucleic acid construct according to this aspect of the present invention further comprising a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be in either one of two possible orientations to result in the transcription of sense RNA which is translatable by the ribozyme machinery or antisense RNA which typically does not contain translatable sequences, yet can duplex or triplex with endogenous sequences, either mRNA or chromosomal DNA and hamper gene expression, all as is further detailed hereinunder.

While the isolated nucleic acid described herein is an essential element of the invention, it is modular and can be used in different contexts. The promoter of choice that is used in conjunction with this invention is of secondary importance, and will comprise any suitable promoter sequence. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

The present invention has the potential to provide transgenic gene and polymorphic gene animal and cellular (cell lines) models as well as for knock-out and knock-in models. These models may be constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, Methods in Enzymology, 194:251-270 1991); Capecchi, Science 244:1288-1292 1989); Davies et al., Nucleic Acids Research, 20 (11) 2693-2698 1992); Dickinson et al., Human Molecular Genetics, 2(8): 1299-1302 1993); Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991); Jakobovits et al., Nature, 362:255-261 1993); Lamb et al., Nature Genetics, 5: 22-29 1993); Pearson and Choi, Proc. Natl. Acad. Sci. USA 1993). 90:10578-82; Rothstein, Methods in Enzymology, 194:281-301 1991); Schedl et al., Nature, 362: 258-261 1993); Strauss et al., Science, 259: 1904-1907 1993). Further, patent applications WO 94/23049, WO93/14200, WO 94106908, WO 94128123 also provide information.

All such transgenic gene and polymorphic gene animal and cellular (cell lines) models and knock-out or knock-in models derived from claimed embodiments of the present invention, constitute preferred embodiments of the present invention.

Gene therapy as used herein refers to the transfer of genetic material (e.g., DNA or RNA) of interest into a host to treat or prevent a genetic or acquired disease or condition or phenotype. The genetic material of interest encodes a product (e.g., a protein, polypeptide, peptide, functional RNA, antisense) whose production in vivo is desired. For example, the genetic material of interest can encode a ligand, hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (i) ex viva and (ii) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to express the transfected genetic material in situ.

In in vivo gene therapy, target cells are not removed from the subject rather the genetic material to be transferred is introduced into the cells of the recipient organism in situ, that is within the recipient. In an alternative embodiment, if the host gene is defective, the gene is repaired in situ (Culver, 1998. (Abstract) Antisense DNA & RNA based therapeutics, February 1998, Coronado, Calif.).

These genetically altered cells have been shown to express the transfected genetic material in situ.

The gene expression vehicle is capable of delivery/transfer of beterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any nontranslated DNA sequence which works contiguously with the coding sequence (in cis) to change the basal transcription level dictated by the promoter. The expression vehicle can also include a selection gene as described hereinbelow.

Vectors can be introduced into cells or tissues by any one of a variety of known methods within the art. Such methods can be found generally described in Sambrook et al., Molecular Cloning: A Laboratory Manual, Cold Springs Harbor Laboratory, New York 1989,1992), in Ausubel et al., Current Protocols in Molecular Biology, John Wiley and Sons, Baltimore, Md. 1989), Chang et al., Somatic Gene Therapy, CRC Press, Ann Arbor, Mich. 1995), Vega et al., Gene Targeting, CRC Press, Ann Arbor Mich. (995), Vectors: A Survey of Molecular Cloning Vectors and Their Uses, Butterworths, Boston Mass. 1988) and Gilboa et al. (Biotechniques 4 (6): 504-512, 1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Features that limit expression to particular cell type can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, reterovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in may cases, to elude host defense mechanisms. Typically, viruses infect and propagate in specific cell types. The targeting specificity of viral utilizes its natural specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration. Following injection, the viral vectors will circulate until they recognize host cells with appropriate target specificity for infection.

Thus, according to an alternative embodiment, the nucleic acid construct according to the present invention further includes a positive and a negative selection markers and may therefore be employed for selecting for homologous recombination events, including, but not limited to, homologous recombination employed in knock-in and knock-out procedures. One ordinarily skilled in the art can readily design a knock-out or knock-in constructs including both positive and negative selection genes for efficiently selecting transfected embryonic stern cells that underwent a homologous recombination event with the construct Such cells can be introduced into developing embryos to generate chimeras, the offspring thereof can be tested for carrying the knock-out or knock-in constructs. Knock-out and/or knock-in constructs according to the present invention can be used to further investigate the functionality of NRG-4. Such constructs can also be used in somatic and/or germ cells gene therapy to destroy activity of a defective, gain of function, e.g., dominant, NRG-4 allele or to replace the lack of activity of a silent NRG-4 allele in an organism, thereby to down or upregulate ErbB-4 activity, as required. Further detail relating to the construction and use of knock-out and knock-in constructs can be found in Fukushige, S. and Ikeda, J. E.: Trapping of mammalian promoters by Cre-lox site-specific recombination. DNA Res 3 (1996) 73-80; Bedell, M. A., Jenkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62, which are incorporated herein by reference.

According to yet another aspect of the present invention there is provided a host cell (either prokaryote or eukaryote) or animal comprising a nucleic acid construct or a portion thereof as described herein. Such a portion may include a coding region and optionally cis acting regulatory sequences. Such a construct or portion may be transient in the cells or organism or be stably integrated in the genome thereof.

According to still another aspect of the present invention there is provided an oligonucleotide of at least 17, at least 18, at least 19, at least 20, at least 22, at least 25, at least 30 or at least 40, bases specifically hybridizable with the isolated nucleic acid described herein.

Hybridization of shorter nucleic acids (below 200 bp in length, e.g., 17-40 bp in length) is effected by stringent, moderate or mild hybridization, wherein stringent hybridization is effected by a hybridization solution of 6.times.SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1-1.5° C. below the $T_m$, final wash solution of 3 M TMACI, 0.01 M sodium phosphate (pH 6.8), 1 mM EDTA (pH 7.6), 0.5% SDS at 1-1.5° C. below the $T_m$; moderate hybridization is effected by a hybridization solution of 6×SSC and 0.1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2-2.5° C. below the $T_m$, final wash solution of 3 M TMACI, 0.01 M sodium phosphate (pH 6.8), 1 mM EDTA (pH 7.6), 0.5% SDS at 1-1.5° C. below the $T_m$, final wash solution of 6×SSC, and final wash at 22° C.; whereas mild hybridization is effected by a hybridization solution of 6×SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each independently of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof, say of 15 to 3000 bp, in a nucleic acid amplification reaction, such as a polymerase chain reaction. The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and zero ° C.

Consequently, according to yet an additional aspect of the present invention there is provided a nucleic acid amplification product obtained using the pair of primers described herein. Such a nucleic acid amplification product can be isolated by gel electrophoresis or any other size based separation technique. Alternatively, such a nucleic acid amplification product can be isolated by affinity separation, either stranded affinity or sequence affinity. In addition, once isolated, such a product can be further genetically manipulated by restriction, ligation and the like, to serve any one of a plurality of applications associated with up and/or down regulation of NRG-4 activity as further detailed herein.

According to still an additional aspect of the present invention there is provided an antisense oligonucleotide comprising a polynucleotide or a polynucleotide analog of at least 10 bases, preferably between 10 and 15, more preferably between 5 and 20 bases, most preferably, at least 17, at least 19, at least 19, at least 20, at least 22, at least 25, at least 30 or at least 40 bases being hybridizable in vivo, under physiological conditions, with a portion of a polynucleotide strand encoding a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% homologous (similar+identical acids) to SEQ ID NOs:2 or 15 as determined using the BestFit software of the Wisconsin sequence analysis package, utilizing the Smith and Waterman algorithm, where gap creation penalty equals 8 and gap extension penalty equals 2. Such antisense oligonucleotides can be used to downregulate expression as further detailed hereinunder. Such an antisense oligonucleotide is readily synthesizable using solid phase oligonucleotide synthesis.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligoucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated. At the translation level, antisense oligonucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool.

For example, several antisense oligonucleotides have been shown to arrest hematopoietic cell proliferation (Szczylik et al., 1991), growth (Calabretta et al., 1991), entry into the S phase of the cell cycle (Heikhila et al., 1987), reduced survival (Reed et al., 1990) and prevent receptor mediated responses (Burch and Mahan, 1991).

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are typically impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done.

Oligonucleotides can be modified either in the base, the sugar or the phosphate moiety. These modifications include, for example, the use of methylphosphonates, monothiophosphates, dithiophosphates, phosphor-ramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, α-anomeric bridges and borane derivatives.

International patent application WO 89112060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone ($—SO_2—$).

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal region.

Thus, in one preferred aspect antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cell. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases. Antisense oligonucleotides are typically synthesized in lengths of 13-30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials. A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dozens of other nucleotide analogs have also been tested in antisense technology.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target a mRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Thus, according to a further aspect of the present invention there is provided a pharmaceutical composition comprising the antisense oligonucleotide described herein and a pharmaceutically acceptable carrier. The pharmaceutically acceptable carrier can be, for example, a liposome loaded with the antisense oligonucleotide. Further particulars pertaining the subject and other pharmaceutical compositions according to the present invention are provided hereinbelow.

According to still a further aspect of the present invention there is provided a ribozyme comprising the antisense oligonucleotide described herein and a ribozyme sequence fused thereto. Such a ribozyme is readily synthesizable using solid phase oligonucleotide synthesis.

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated-WEB home page).

According to yet a further aspect of the present invention there is provided a recombinant or synthetic (i.e., prepared using solid phase peptide synthesis) protein comprising a polypeptide capable of binding to ErbB-4 receptor and which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

Most preferably the polypeptide includes at least a portion of SEQ ID NOs:2 or 15. That portion may include amino acids at positions position 4 to position 50 which include the EGF-like domain of NRG-4.

Additionally or alternatively, the polypeptide according to this aspect of the present invention is preferably encoded by a polynucleotide hybridizable with SEQ ID NOs:1 or 14 or a portion thereof under any of the stringent or moderate hybridization conditions described above for long nucleic acids. Still additionally or alternatively, the polypeptide according to this aspect of the present invention is preferably encoded by a polynucleotide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100%, identical with SEQ ID NOs:1 or 14 or portions thereof as determined using the BestFit software of the Wisconsin sequence analysis package, utilizing the Smith and Waterman algorithm, where gap weight equals 50, length weight equals 3, average match equals 10 and average mismatch equals −9.

Thus, this aspect of the present invention encompasses (i) polypeptides as set forth in SEQ ID NOs:2 or 15; (ii) fragments thereof; (iii) polypeptides homologous thereto; and (iv) altered polypeptides characterized by mutations, such as deletion, insertion or substitution of one or more amino acids, either naturally occurring or man induced, either random or in a targeted fashion, either natural, non-natural or modified at or after synthesis.

According to still a further aspect of the present invention there is provided a pharmaceutical composition comprising an iiinunoadhesin. As used herein the term "immununoadhesin" is used to describe a chimeric antibody-like molecule that comprises the functional domain of a binding protein (usually a receptor, a cell-adhesion molecule or a ligand) and an immunoglobulin linked thereto. This type of molecule is called an "immunoadhesin", because it combines "immune" and "adhesion" functions; other frequently used names that describe immunoadhesins are "Ig-chimera", "Ig-" and "Fc-fusion protein".

Immunoadhesins reported in the literature include, for example, fusions of the T cell receptor (Gascoigne et al. (1987) Proc. Natl. Acad. Sci. USA 84:2936-2940); CD4 (Capon et al. (1989) Nature 337:525-531; Traunecker et al. (1989) Nature 339:68-70; Zettneissl et al. (1990) DNA Cell Biol. USA 9:347-353; Byrn et al. (1990) Nature 344:667-670); LFA-3 (Kanner et al. (1992) J. Immunol. 148:23-29); L1 glycoprotein (Doherty et al. (1995) Neuron 14:57-66); TNF-R1 (Ashkenazi et al., (1991) Proc. Natl. Acad. Sci. USA 88:10535-539); Lesslauer et al. (1991) Eur. J. Immunol. 21:2883-86; Peppel et al. (1991) J. Exp. Med. 174:1483-1489) and ErbB-4 (Tzahar et al. (1996) Mol. Cell. Biol. 16:5276-87).

The simplest and most straightforward immunoadhesin design combines the binding region(s) of the "adhesing" protein with the hinge and Fc regions of an immunoglobulin heavy chain.

Thus, according to a preferred embodiment of this aspect of the present invention, when preparing the NRG-4-immunoglobulin immunoadhesin, a polynucleotide encoding the polypeptide which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2 is fused, preferably, at the C-terminus to, preferably, the N-terninus of another polynucleotide encoding an immunoglobulin constant domain sequence, however fusion of the immunoglobulin to the N-terminus of the desired NRG4 sequence is also applicable. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the NRG4-immunoglobulin chimeras.

In a preferred embodiment, the immunoglobulin sequences used in the construction of the immunoadhesins of the present invention include an IgG immunoglobulin heavy chain constant domain. For human immunoadhesins, the use of human or humanized IgG-1 and IgG-3 immunoglobulins is preferred. A major advantage of using IgG-1 is that IgG-1 immunoadhesins can be efficiently purified using immobilized protein A.

In contrast, purification of IgG-3 requires the use of immobilized protein G, a significantly less versatile medium. However, other structural and functional properties of immunoglobulins should be considered when choosing the Ig fusion partner for a particular immunoadhesin construction. For example, the IgG-3 hinge is longer and more flexible, so as to accommodate larger adhesin domains that may not fold or function properly when fused to, for example, IgG-1. While IgG immunoadhesins are typically mono- or bivalent, other Ig subtypes such as IgA and IgM may give rise to dimeric or pentameric structures, respectively, of the basic Ig homodimer unit. Multimeric immunoadhesins are advantageous in that they can bind their respective targets with greater avidity than their IgG-based counterparts.

According to still a further aspect of the present invention there is provided a pharmaceutical composition which comprises an activity delivering fusion protein. Activity delivering proteins are well known in the art and have been developed to chemically modify toxins, drugs or enzymes in-order to render such toxins, drugs or enzymes coupleable to growth factors, antibodies, and other biologically active molecules, so as to render the toxins, drugs or enzymes capable of selective binding to, and hence concentrating at, a target, so as to destroy or mudulate the behavior of target cells such as tumor or other types of cells displaying specific molecules on their cell surface.

For example, the *Pseudomonas* exotoxin (PE) has been conjugated to a variety of monoclonal antibodies recognizing certain human tumors (Cetus Corporation) and to a monoclonal antibody recognizing the human H Type 1 blood group substance [Richert et al. (1983) J. Biol. Chem., 258:8902-8907, and Fredman et al. (1983) J. Biol. Chem., 258:11206-11210].

A toxin-conjugate is thus designed to specifically kill appropriate target cells. Toxins, such as PE, can thus be coupled to a variety of peptides, proteins and growth factors that react with receptors specific to target cells. Such proteins and growth factors include, for example, sarcoma growth factors, malanocyte stimulating hormone (MSH), somatostatin, glucogon, insulin, transferrin, low density lipoprotein, calcitonin, $\alpha_2$-macroglobulin and lysine bradykinin. Conjugates with MSH and lysine bradykinin have already been prepared and show biological activity.

Thus, according to a preferred embodiment of this aspect of the present invention, when preparing the NRG-4 drug, toxin or enzyme fusion protein, a polynucleotide encoding the polypeptide which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2 is fused to a toxin. Fusion can take place C-terminally or N-terminally to the NRG-4, since the site of the fusion is not critical.

According to a preferred embodiment of the invention *Pseudomonas* exotoxin-NRG4 fusions or conjugates (PE-NRG4) are prepared, although the conjugate may include other well known toxins, such as, but not limited to, pertussis toxin, anthrax toxin, diphtheria toxin, etc. *Pseudomonas* exotoxin is particularly preferable over other toxins (such as ricin or diptheria toxin) because it is easily prepared in large amounts and because humans do not contain the antibodies to neutralize it (as is the case with diptheria toxin) and because it does not have to be separated into subunits before being conjugated. Alternatively NRG4 may be conjugated to a drug or an enzyme.

Construction is preferably done either using a disulfide exchange reaction or by forming a thioether bond. Generally, PE is treated with methyl-4-mercaptobutyrimidate (MMB) in order to introduce two thiol groups per molecule of toxin. This step is optimally conducted in 10 mM $KPO_4$ (pH 8.5). Derivatized PE from the above step is then reacted with dithiobis(2-nitrobenzoic acid) (DTNB). Recombinant NRG4 is also treated with MMB in order to introduce slightly more than one thiol group per molecule. The treated NRG4 is then mixed with excess treated PE and allowed to incubate for 2 hrs at 23° C. Alternatively the NRG4 can be modified with m-maleimidobenzoyl N hydroxy-succinimide ester (MBS) and the resulting activated NRG4 reacted with SH-PE-SH to produce a conjugate containing a thioether bond-more stable in an animal environment since it cannot be inactivated by reduction of a disulfide bond.

The resulting PE-NRG4 conjugate is then purified in a multi-step procedure. Typically, 1 ml of conjugate at 3-5 mg/ml is passed over a Sepharose column. Large aggregates in the void volume exhibiting low activity are discarded. The material remaining on the Sepharose 6B column is further purified and separated from unreacted PE by passing the conjugate over a Sephadex column. The first pool, containing the PE-NRG4 conjugates used in this invention, includes each PE molecule coupled to one or two antibody molecules. This material reacted with DTNB and then cysteine to derivatize all free-SH groups. Tracer amounts of $^{125}$I-PE may be used to follow the separation procedure. The conjugate is assayed by adding it to tumor cells bearing ErbB4, such as HeLa cells and measuring inhibition of protein synthesis or cell death. The ADP-ribosylating activity of the conjugates is also assayed in cell extracts, usually reticulocyte lysates, using $^{14}$C-NAD as described in Fitzgerald et al., Cell, Vol. 32, p. 607 (1983).

According to still a further aspect of the present invention there is provided a pharmaceutical composition comprising, as an active ingredient, the recombinant protein or the immunoadhesin described herein and a pharmaceutical acceptable carrier which is further described above.

According to another aspect of the present invention there is provided a peptide or a peptide analog comprising a stretch of at least 6, at least 7, at least 8, at least 9, at least 10, 10-15, 12-17, or 15-20 consecutive amino acids or analogs thereof derived from a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2. Preferably, the peptide or the peptide analog according to this aspect of the present invention comprises a stretch of at least 6, at least 7, at least 8, at least 9, at least 10, 10-15, 12-17, or 15-20 consecutive amino acids or analogs thereof derived from SEQ ID NOs:2 or 15.

As used herein in the specification and in the claims section below the phrase "derived from a polypeptide" refers to peptides derived from the specified protein or proteins and further to homologous peptides derived from equivalent regions of proteins homologous to the specified proteins of the same or other species. The term further relates to permissible amino acid alterations and peptidomimetics designed based on the amino acid sequence of the specified proteins or their homologous proteins.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids are given hereinunder.

Hydrophilic aliphatic natural amino acids can be substituted by synthetic amino acids, preferably Nleu, Nval and/or α-aminobutyric acid or by aliphatic amino acids of the general formula —$HN(CH_2)_nCOOH$, wherein n=3-5, as well as by branched derivatives thereof; such as, but not limited to:

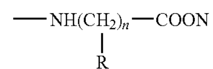

wherein R is, for example, methyl, ethyl or propyl, located at any one or more of the n carbons.

Each one, or more, of the amino acids can include a D-isomer thereof. Positively charged aliphatic carboxylic acids, such as, but not limited to, $H_2N(CH_2)_nCOOH$, wherein n=2-4 and $H_2N$—C(NH)—$NH(CH_2)_nCOOH$, wherein n=2-3, as well as by hydroxy Lysine, N-methyl Lysine or ornithine (Om) can also be employed. Additionally, enlarged aromatic residues, such as, but not limited to, $H_2N$—$(C_6H_6)$—$CH_2$—COOH, p-aminophenyl alanine, $H_2N$—F(NH)—NH—$(C_6H_6)$—$CH_2$—COOH, p-guanidino phenyl alanine or pyridinoalanine (Pal) can also be employed. Side chains of amino acid derivatives (if these are Ser, Tyr, Lys, Cys or Orn) can be protected-attached to alkyl, aryl, alkyloyl or aryloyl moieties. Cyclic derivatives of amino acids can also be used. Cyclization can be obtained through amide bond formation, e.g., by incorporating Glu, Asp, Lys, Om, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—$N((CH_2)_n$—COOH)—C(R)H—COOH or H—$N((CH_2)_n$—COOH)—C(R)H—$NH_2$, wherein n=1-4, and further wherein R is any natural or non-natural side chain of an amino acid. Cyclization via formation of S—S bonds through incorporation of two Cys residues is also possible. Additional side-chain to side chain cyclization can be obtained via formation of an interaction bond of the formula —(—$CH_2$—$)_n$—S—$CH_2$—C—, wherein n=1 or 2, which is possible, for example, through incorporation of Cys or homoCys and reaction of its free SH group with, e.g., bromoacetylated Lys, Orn, Dab or Dap. Peptide bonds (—CO—NH—) within the peptide may be substituted by N-methylated bonds (—$N(CH_3)$—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$), thioamide bonds (—CS—NH—), olefinic double bonds (—CH═CH—), retro amide bonds (—NH—CO—), peptide derivatives (—N(R)—$CH_2$—CO—), wherein R is the "normal" side chain, naturally presented on the carbon atom. These modifications can occur at any of the bonds along the peptide chain and even at several (2-3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine Cys | Cys | C |
| Glutamine | Gln | Q |
| Glutamic Acid | Clu | E |
| Glycine | Gly | G |
| Histidine | His | H |
| Isoleucine | Iie | I |

TABLE 1-continued

| Amino Acid | Three-Letter Abbreviation | One-letter Symbol |
|---|---|---|
| Leucine | Leu | L |
| Lysine | Lys | K |
| Methionine | Met | M |
| Phenylanine | Phe | F |
| Proline | Pro | P |
| Serine | Ser | S |
| Threonine | Thr | T |
| Tryptophan | Trp | W |
| Tyrsosine | Tyr | Y |
| Valien | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| aminoisobutyric acid | Aib | L-N-methylaspartic acid | Nmasp |
| aminonorbornyl carboxylate | Norb | L-N-methylcysteine | Nmcys |
| cyclohexylalanine | Chexa | L-N-methylglutamine | Nmgin |
| cyclopentylalanine | Cpen | L-N-methylglutamic acid | Nmglu |
| D-alanine | Dal | L-N-methylhistidine | Nmhis |
| D-arginine | Darg | L-N-methylisolleucine | Nmile |
| D-aspartic acid | Dasp | L-N-methylleucine | Nmleu |
| D-cysteine | Dcys | L-N-methyllysine | Nmlys |
| D-glutamine | Dgln | L-N-methylmethionine | Nmmet |
| D-glutamic acid | Dglu | L-N-methylnorleucine | Nmnle |
| D-histidine | Dhis | L-N-methylnorvaline | Nmnva |
| D-isoleucine | Dile | L-N-methylornithine | Nmorn |
| D-leucine | Dleu | L-N-methylphenylalanine | Nmphe |
| D-lysine | Dlys | L-N-methylproline | Nmpro |
| D-methionine | Dmet | L-N-methylserine | Nmser |
| D-ornithine | Dorn | L-N-methylthreonine | Nmthr |
| D-phenylalanine | Dphe | L-N-methyltryptophan | Nmtrp |
| D-proline | Dpro | L-N-methyltyrosine | Nmtyr |
| D-serine | Dser | L-N-methylvaline | Nmval |
| D-threonine | Dthr | L-N-methylethylglycine | Nmetg |
| D-tryptophan | Dtrp | L-N-methyl-t-butylglycine | Nmtbug |
| D-tyrosine | Dtyr | L-norleucine | Nle |
| D-valine | Dval | L-norvaline | Nva |
| D-α-methylalanine | Dmala | α-methyl-aminoisobutyrate | Maib |
| D-α-methylarginine | Dmarg | α-methyl-γ-aminobutyrate | Mgabu |
| D-α-methylasparagine | Dmasn | α-methylcyclohexylalanine | Mchexa |
| D-α-methylaspartate | Dmasp | α-methylcyclopentylalanine | Mcpen |
| D-α-methylcysteine | Dmcys | α-methyl-α-napthylalanine | Manap |
| D-α-methylglutamine | Dmgln | α-methylpenicillamine | Mpen |
| D-α-methylhistidine | Dmhis | N-(4-aminobutyl)glycine | Nglu |
| D-α-methylisoleucine | Dmile | N-(2-aminoethyl)glycine | Naeg |
| D-α-methylleucine | Dmleu | N-(3-aminopropyl)glycine | Norn |
| D-α-methyllysine | Dmlys | N-amino-α-methylbutyrate | Nmaabu |
| D-α-methylmethionine | Dmmet | α-napthylalanine | Anap |
| D-α-methylornithine | Dmorn | N-benzylglycine | Nphe |
| D-α-methylphenylalanine | Dmphe | N-(2-carbamylethyl)glycine | Ngln |
| D-α-methylproline | Dmpro | N-(carbamylmethyl)glycine | Nasn |
| D-α-methylserine | Dmser | N-(2-carboxyethyl)glycine | Nglu |
| D-α-methylthreonine | Dmthr | N-(carboxymethyl)glycine | Nasp |
| D-α-methyltryptophan | Dmtrp | N-cyclobutylglycine | Ncbut |
| D-α-methyltyrosine | Dmty | N-cycloheptylglycine | Nchep |
| D-α-methylvaline | Dmval | N-cyclohexylglycine | Nchex |
| D-α-methylalnine | Dnmala | N-cyclodecylglycine | Ncdec |
| D-α-methylarginine | Dnmarg | N-cyclododeclglycine | Ncdod |
| D-α-methylasparagine | Dnmasn | N-cyclooctylglycine | Ncoct |
| D-α-methylasparatate | Dnmasp | N-cyclopropylglycine | Ncpro |
| D-α-methylcysteine | Dnmcys | N-cycloundecylglycine | Ncund |
| D-N-methylleucine | Dnmleu | N-(2,2-diphenylethyl)glycine | Nbhm |
| D-N-methyllysine | Dnmlys | N-(3,3-diphenylpropyl)glycine | Nbhe |
| N-methylcyclohexylalanine | Nmchexa | N-(3-indolylyethyl) glycine | Nhtrp |
| D-N-methylornithine | Dnmorn | N-methyl-γ-aminobutyrate | Nmgabu |
| N-methylglycine | Nala | D-N-methylmethionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |

TABLE 2-continued

| Non-conventional amino acid | Code | Non-conventional amino acid | Code |
|---|---|---|---|
| N-(2-methylpropyl)glycine | Nile | D-N-methylproline | Dnmpro |
| N-(2-methylpropyl)glycine | Nleu | D-N-methylserine | Dnmser |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nva |
| γ-aminobutyric acid | Gabu | N-methyla-napthylalanine | Nmanap |
| L-t-butylglycine | Tbug | N-methylpenicillamine | Nmpen |
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| D-N-methylglutamine | Dnmgln | L-α-methylhomophenylalanine | Mhphe |
| D-N-methylglutamate | Dnmglu | N-(2-methylthioethyl)glycine | Nmet |
| D-N-methylhistidine | Dnmhis | N-(3-guanidinopropyl)glycine | Narg |
| D-N-methylisoleucine | Dnmile | N-(1-hydroxyethyl)glycine | Nthr |
| D-N-methylleucine | Dnmleu | N-(hydroxyethyl)glycine | Nser |
| D-N-methyllysine | Dnmlys | N-(imidazolylethyl)glycine | Nhis |
| N-methylcyclohexylalanine | Nmchexa | N-(3-indolylyethyl)glycine | Nhtrp |
| D-N-methylornithine | Dnmorn | N-methyl-γ-aminobutyrate | Nmgabu |
| N-methylglycine | Nala | D-N-methylmethionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nleu | D-N-methylproline | Dnmpro |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nval |
| γ-aminobutyric acid | Gabu | N-methyla-napthylalanine | Nmanap |
| L-t-butylglycine | Tbug | N-methylpenicillamine | Nmpen |
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| L-α-methylleucine | Mleu | L-α-methylhomophenylalanine | Mhphe |
| L-α-methylmethionine | Mmet | N-(2-methylthioethyl)glycine | Nmet |
| L-α-methylnorvaline | Mnva | L-α-methyllysine | Mlys |
| L-α-methylphenylalanine | Mphe | L-α-methylnorleucine | Mnle |
| L-α-methylserine | mser | L-α-methylornithine | Morn |
| L-α-methylvaline | Mtrp | L-α-methylproline | Mpro |
| L-α-methylleucine | Mval | L-α-methylthreonine | Mthr |
| N-(N-(2,2-diphenylethyl)carbamylmethyl-glycine | Nnbhm | L-α-methyltyrosine | Mtyr |
| 1-carboxy-1-(2,2-diphenylethylamino)cyclopropane | Nnbhm | L-N-ethylhomophenylalanine | Nmhphe |
| | Nmbc | N-(N-(3,3-diphenylpropyl)carbamylmethyl(1)glycine | Nnbhe |

According to still another aspect of the present invention there is provided a display library comprising a plurality of display vehicles (such as phages, viruses or bacteria) each displaying at least 6, at least 7, at least 8, at least 9, at least 10, 10-15, 12-17, or 15-20 consecutive amino acids derived from a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

According to a preferred embodiment of this aspect of the present invention substantially every 6, 7, 8, 9, 10, 10-15, 12-17 or 15-20 consecutive amino acids derived from the polypeptide which is at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 are displayed by at least one of the plurality of display vehicles, so as to provide a highly representative library. Preferably, the consecutive amino acids or amino acid analogs of the peptide or peptide analog according to this aspect of the present invention are derived from SEQ ID NOs:2 or 15.

Methods of constructing display libraries are well known in the art. such methods are described, for example, in Young A C, et al., "The three-dimensional structures of a polysaccharide binding antibody to *Cryptococcus neoformans* and its complex with a peptide from a phage display library: implications for the identification of peptide mimotopes" J Mol Biol Dec. 12, 1997;274(4):622-34; Giebel L B et al. "Screening of cyclic peptide phage libraries identifies ligands that bind streptavidin with high affinities" Biochemistry Nov. 28, 1995; 34(47):15430-5; Davies E L et al., "Selection of specific phage-display antibodies using libraries derived from chicken iminunoglobulin genes" J Immunol Methods Oct. 12, 1995;186(1):125-35; Jones C R T al. "Current trends in molecular recognition and bioseparation" J Chromatogr A Jul. 14, 1995;707(1):3-22; Deng S J et al. "Basis for selection of improved carbohydrate-binding single-chain antibodies from synthetic gene libraries" Proc Natl Acad Sci USA May 23, 1995;92(11):4992-6; and Deng S J et al. "Selection of antibody single-chain variable fragments with improved carbohydrate binding by phage display" J Biol Chem Apr. 1, 1994;269(13):9533-8, which are incorporated herein by reference. Display libraries according to this aspect of the present invention can be used to identify and isolate polypeptides which are capable of up- or down-regulating ErbB-4 activity.

According to still another aspect of the present invention there is provided an antibody comprising an immunoglobulin specifically recognizing and binding a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and. Waterman algorithm, where gap creation penalty equals 8 and gap extension penalty equals 2. According to a preferred embodiment of this aspect of the present invention the antibody specifically recognizing and binding the polypeptides set forth in SEQ ID NOs:2 or 15.

The present invention can utilize serum immunoglobulins, polyclonal antibodies or fragments thereof, (i.e., immunoreactive derivative of an antibody), or monoclonal antibodies or fragments thereof Monoclonal antibodies or purified fragments of the monoclonal antibodies having at least a portion of an antigen binding region, including such as Fv, F(abl)2, Fab fragments (Harlow and Lane, 1988 Antibody, Cold Spring Harbor), single chain antibodies (U.S. Pat. No. 4,946, 778), chimeric or humanized antibodies and complementarily determining regions (CDR) may be prepared by conventional procedures. Purification of these serum immunoglobulins antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes includes IgD, IgE, IgA, IgM and related proteins.

Methods for the generation and selection of monoclonal antibodies are well known in the art, as summarized for example in reviews such as Tramontano and Schloeder, Methods in Enzymology 178, 551-568, 1989. A recombinant or synthetic NRG-4 or a portion thereof of the present invention may be used to generate antibodies in vitro. More preferably, the recombinant or synthetic NRG-4 of the present invention is used to elicit antibodies in vivo. In general, a suitable host animal is immunized with the recombinant or synthetic NRG-4 of the present invention or a portion thereof including at least one continuous or discontinuous epitope. Advantageously, the animal host used is a mouse of an inbred strain. Animals are typically immunized with a mixture comprising a solution of the recombinant or synthetic NRG-4 of the present invention or portion thereof in a physiologically acceptable vehicle, and any suitable adjuvant, which achieves an enhanced immune response to the immunogen. By way of example, the primary immunization conveniently may be accomplished with a mixture of a solution of the recombinant or synthetic NRG-4 of the present invention or a portion thereof and Freund's complete adjuvant, said mixture being prepared in the form of a water in oil emulsion. Typically the immunization may be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding can be determined during the immunization schedule by any convenient method including by way of example radioimmunoassay, or enzyme linked immunosorbant assay, which is known as the ELISA assay. When suitable antibody titers are achieved, antibody producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multiwell plates, and the culture supernatants are screened to identify cultures containing antibodies that recognize the hapten of choice. Hybridomas that secrete antibodies that recognize the recombinant or synthetic NRG-4 of the present invention are cloned by limiting dilution and expanded, under appropriate culture conditions. Monoclonal antibodies are purified and characterized in terms of immunoglobulin type and binding affinity.

The following embodiments of the present invention are directed at intervention with NRG-4 activity and therefore with ErbB-4 receptor signaling.

Thus, according to yet another aspect of the present invention there is provided a pharmaceutical composition comprising, as an active ingredient, an agent for regulating an endogenous protein affecting ErbB-4 receptor activity in vivo or in vitro, the endogenous protein being at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

According to yet another aspect of the present invention there is provided a method of regulating an endogenous protein affecting ErbB-4 receptor activity in vivo or in vitro. The method according to this aspect of the present invention is effected by administering an agent for regulating the endogenous protein activity in vivo, the endogenous protein being at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

According to still another aspect of the present invention there is provided a method of treating or preventing a disease, condition or syndrome associated with disregulation of an endogenous protein affecting ErbB-4 receptor activity. The method according to this aspect of the present invention is effected by administering a therapeutically effective amount of an agent for regulating an endogenous protein affecting ErbB-4 receptor activity, said endogenous protein being at least 50% homologous to at least positions 4-50 of SEQ ID NOs:2 or 15 as determined using the BestFit software of the Wisconsin sequence analysis package, utilizing the Smith and Waterman algorithm, where gap creation penalty equals 8 and gap extension penalty equals 2.

An agent which can be used according to the present invention to upregulate the activity of the endogenous protein and/or treating or preventing a disease, condition or syndrome associated with disregulation of an endogenous protein affecting ErbB-4 receptor activity, can include, for example, an expressible sense polynucleotide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

Alternatively, an agent which can be used according to the present invention to upregulate the activity of the endogenous protein can include, for example, at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

An agent which can be used according to the pre sent invention to downregulate the activity of the endogenous protein can include, for example, an expressible antisense polynucleotide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100%, identical with SEQ ID NOs:1 or 14 as determined using the BestFit software of the Wisconsin sequence analysis package, utilizing the Smith and Waterman algorithm, where gap weight equals 50, length weight equals 3, average match equals 10 and average mismatch equals −9.

Alternatively, an agent which can be used according to the present invention to downregulate the activity of the endogenous protein can include, for example, an antisense oligonucleotide or ribozyme which includes a polynucleotide or a polynucleotide analog of at least 10 bases, preferably between 10 and 15, more preferably between 50 and 20 bases, most preferably, at least 17, at least 18, at least 19, at least 20, at least 22, at least 25, at least 30 or at least 40 bases which is hybridizable in vivo, under physiological conditions, with a portion of a polynucleotide strand encoding a polypeptide at least 50%, at least 55% at least 60% at least 65%, at least 70%, at least 75%, at least 80%, at least 85%, at least 90% or more,.say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

Still alternatively, an agent which can be used according to the present invention to downregulate the activity of the endogenous protein can include, for example, a peptide or a peptide analog representing a stretch of at least 6, at least 7, at least 8, at least 9, at least 10, 10-15, 12-17, or 15-20 consecutive amino acids or analogs thereof derived from a polypeptide at least 50%, at least 55% at least 60% at least 65%, at least 70%, at least 75%, at least 80%, at least 85%, at least 90% or more, say at least 91%, at least 92%, at least 93%, at least 94%, at least 95%, at least 96%, at least 97%, at least 98%, at least 99% or 100% identical or homologous (identical+similar) to SEQ ID NOs:2 or 15 as determined using the BestFit software of the Wisconsin sequence analysis package, utilizing the Smith and Waterman algorithm, where gap creation penalty equals 8 and gap extension penalty equals 2.

Peptides or peptide analogs containing the interacting EGF-like domain of NRG-4 according to the present invention will compete by protein interactions to form protein complexes with ErbB4, inhibiting or accelerating the pathways in which ErbB-4 is involved.

For preventing or treating a disease, condition or syndrom in accordance with the teachings of the present invention one may also consider the use of a polypeptide capable of binding an endogenous protein affecting ErbB-4 receptor activity via titration, such as, a soluble ligand binding domain of ErbB-4 (Tzahar et al., 1996) or an anti-NRG4 antibody as described above. In one embodiment of the invention the soluble ligand binding domain of ErbB-4 is IgB4, an immunoadhesin (Tzahar et al., 1996).

An agent, which is also referred to herein alternatively as an active ingredient can be administered to an organism per se, or in a pharmaceutical composition where it is mixed with suitable carriers or excipients.

As used herein a "pharmaceutical composition" refers to a composition of one or more of the agents described herein, or physiologically acceptable salts or prodrugs thereof, with other chemical components such as physiologically suitable carriers and excipients. The purpose of a pharmaceutical composition is to facilitate administration of a compound to an organism.

Hereinafter, the terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of an agent. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer an agent in a local rather than systemic manner, for example, via injection of the composition directly into a solid tumor often in a depot or slow release formulation, such as described below.

Furthermore, one may administer the drug in a targeted drug delivery system, for example, in a liposome coated with a tumor specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active agents into compositions which, can be used pharmaceutically. Proper formulation is dependent upon the route of administration chosen.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions, and the like, for oral ingestion by a patient. Pharmacological compositions for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose compositions such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active agent doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the agents for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the agent and a suitable powder base such as lactose or starch.

The compositions described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active composition in water-soluble form. Additionally, suspensions of the active agents may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the agents to allow for the composition of highly concentrated solutions.

Alternatively, the active ingredient may be in powder form for constitution with a suitable vehicle, e.g., sterile, pyrogen-free water, before use.

The composition of the present invention may also be formulated in rectal compositions such as suppositories or retention enemas, using, e.g., conventional suppository bases such as cocoa butter or other glycerides.

In addition to the formulations described previously, a composition of the present invention may also be formulated for local administration, such as a depot composition. Such long acting formulations may be administered by implantation (for example subcutaneously or intramuscularly) or by intramuscular injection. Thus, for example, the composition may be formulated with suitable polymeric or hydrophobic materials (for example, as an emulsion in an acceptable oil) or ion exchange resins, or as sparingly soluble derivatives such as sparingly soluble salts Formulations for topical administration may include, but are not limited to, lotions, suspensions, ointments gels, creams, drops, liquids, sprays emulsions and powders.

According to a preferred embodiment of the present invention, the pharmaceutical composition is designed for a slow release of the agent. The composition includes particles including a slow release carrier (typically, a polymeric carrier), such as, for example, polylactic acid, and the agent. Slow release biodegradable carriers are well known in the art. These are materials that may form particles that may capture therein an active agent(s) and slowly degrade/dissolve under a suitable environment (e.g., aqueous, acidic, basic, etc.) and thereby degrade/dissolve in body fluids and release the active agent(s) therein. The particles are preferably nanoparticles (i.e., in the nanometer range, e.g., in the range of about 1 to about 500 nm in diameter, preferably about 50-200 nm in diameter, most preferably about 100 nm in diameter).

Further according to the present invention there is provided a method of preparing a pharmaceutical composition for slow release.

The method includes the following steps:

A slow release carrier (typically, a polymeric carrier) and the an agent as described herein are dissolved or dispersed in an organic solvent for obtaining an organic solution containing the carrier and the an agent as described herein. Then, the organic solution is added into an aqueous solution for obtaining an oil-in-water-type emulsion. Preferably, the aqueous solution includes surface-active agent(s). Finally, the organic solvent is evaporated from the oil-in-water-type emulsion for obtaining a colloidal suspension of particles containing the slow release carrier and an agent as described herein.

According to a preferred embodiment of the present invention the slow release carrier is polylactic acid.

The pharmaceutical compositions herein described may also comprise suitable solid of gel phase carriers or excipients. Examples of such carriers or excipients include, but are not-limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of agent effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any composition used in the methods of the invention, the therapeutically effective amount or dose can be estimated initially from cell culture assays. For example, a dose can be formulated in animal models to achieve a circulating concentration range that includes the $IC_{50}$ as determined in cell culture. Such information can be used to more accurately determine useful doses in humans.

Toxicity and therapeutic efficacy of the agents described herein can be determined by standard pharmaceutical procedures in cell cultures or experimental animals, e.g., by determining the $IC_{50}$ and the $LD_{50}$ (lethal dose causing death in 50% of the tested animals) for a subject agent. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the required effects, termed the minimal effective concentration (MEC). The MEC will vary for each composition, but can be estimated from in vitro data; e.g., the concentration necessary to achieve 50-90% inhibition. Dosages necessary to achieve the MEC will depend on individual characteristics and route of administration. HPLC assays or bioassays can be used to determine plasma concentrations.

Dosage intervals can also be determined using the MEC value. Compositions should be administered using a regimen, which maintains plasma levels above the MEC for 10-90% of the time, preferable between 30-90% and most preferably 50-90%.

It is noted that, in the case of local administration or selective uptake, the effective local concentration of the drug may not be related to plasma concentration. In such cases, other procedures known in the art can be employed to determine the effective local concentration.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an agent of the invention formulated in a compatible pharmaceutical carrier may also be prepared, placed in an appropriate container, and labeled for treatment of an indicated condition. Suitable conditions indicated on the label are further described herein below.

Thus, the pharmaceutical compositions described hereinabove are useful in treating or preventing diseases or conditions or syndromes associated with disregulation of NRG-4, affecting ErbB-4 activity.

Binding and activation of the ErbB-4 receptor by NRG4 is expected to mediate physiological responses in cells expressing the ErbB4 receptor, such as cell growth, cell proliferation, and cell differentiation. This is particularly, but not exclusively, expected for skeletal muscle tissue where both the ErbB4 receptor and its novel NRG4 ligand are expressed, being capable of autocrine and/or paracrine effects.

Diseases, conditions and syndromes treatable and/or preventable by administration of a pharmaceutical composition as herein described include, but are not limited to, (i) disorders that arise due to damage to the nervous system by, for example, trauma, surgery, stroke, ischemia, infection, metabolic disease, nutritional deficiency, malignancy, or toxic agents; (ii) motoneuron disorders, such as amyotrophic lateral sclerosis (Lou Gehrig's disease), Bell's palsy; (iii) various conditions involving spinal muscular atrophy, or paralysis; (iv) neurodegenerative disorders of either inherited familial or aquired nature, such as Alzheimer's disease, Parkinson's disease, epilepsy, multiple sclerosis, Huntington's chorea, Down's Syndrome, nerve deafness and Meniere's disease; (v) neuropathies, and especially peripheral neuropathy, referring to disorders affecting the peripheral nervous system, most often manifested as one or a combination of motor, sensory, sensorimotor, or autonomic neural dysfunction, such as distal sensorimotor neuropathy, or autonomic neuropathies including reduced motility of the gastrointestinal tract or atony of the urinary bladder, examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine; (vi) diseases of skeletal muscles or smooth muscles, such as muscular dystrophy or diseases caused by skeletal or smooth muscle wasting; (vii) pancreatic diseases such as pancreatic cancer, pancreatitis, somatostatinoma and Zollinger-Ellison syndrome; and (viii) malignancies, such as extramammary Paget's disease, gastric cancer, prostate cancer, breast cancer, ovarian cancer (Gilmour L M R. et al 2001), cervical carcinoma and endometrial carcinoma.

The following biochemical and molecular systems are known for the characterization and identification of protein-protein interaction and peptides as substrates, through peptide analysis, which systems can be used to identify inhibitory peptide sequences. One such system employs introduction of a genetic material encoding a functional protein or a mutated form of the protein, including amino acid deletions and substitutions, into cells. This system, can be used to identify functional domains of the protein by the analysis of its activity and the activity of its derived mutants in the cells. Another such system employs the introduction of small encoding fragments of a gene into cells, e.g., by means of a display library or a directional randomly primed cDNA library comprising fragments of the gene, and analyzing the activity of the endogenous protein in their presence (see, for example, Gudkov et al. (1993) "Isolation of genetic suppressor elements, including resistance to topoisomerase II interactive cytotoxic drugs, from human topoisomerase II cDNA" Proc. Natl. Acad. Sci. USA 90:3231-3236; Gudkov and Robinson (1997) "Isolation of genetic suppressor elements (GSEs) from random fragment cDNA libraries in retroviral vectors" Methods Mol Biol 69;221-240; and Pestov et al. (1999) "Flow Cytometric Analysis of the cell cycle in transfected cells without cell fixation" Bio Techniques 26:102-106). Yet an additional system is realized by screening expression libraries with peptide domains, as exemplified, for example, by Yamabhai et al. (1998 "Intersectin, a Novel Adaptor Protein with Two Eps15 Homology and Five Src Homology 3 Domains". J Biol Chem 273: 31401-31407). In yet another such system overlapping synthetic peptides derived from specific gene products are used to study and affect in vivo and in vitro protein-protein interactions. For example, synthetic overlapping peptides derived from the HIV-1 vif gene (20-30 amino acids) were assayed for different viral activities (Baraz et al. (1998) "Human immunodefficiency virus type 1 Vif derived peptides inhibit the viral protease and arrest virus production" FEBS Letters 441:419-426) and were found to inhibit purified viral protease activity; bind to the viral protease; inhibit the Gag-Pol polyprotein cleavage; and inhibit mature virus production in human cells.

The Her/ErbB tyrosine kinase growth factor receptor family is presently known to includes four plasma membrane-spanning receptors, ErbB-1 (also known as the Epidermal Growth Factor Receptor), ErbB-2, ErbB-3 and ErbB-4.

These receptor tyrosine kinases are typically activated in a ligand-dependent manner, resulting in receptor oligomerization, their self-phosphorylation upon key intracellular tyrosine residues and subsequent activation of downstream signaling cascades. ErbB receptors and their corresponding ligands play numerous instrumental roles in mammalian development and have also been demonstrated to act as potent oncogenes in for example, breast cancer (ErbB1 and ErbB-2) and in glioblastoma (ErbB1). Overexpression of different ErbBs in many other cancers, often correlating with poorer survival prognosis, implicates a far greater functional role of ErbBs and their ligands in oncogenesis (reviewed in: Burden and Yarden., 1997; Klapper et al 2000).

For a particular cell type, ErbB signaling is dependent upon two major factors (i) the quantity and type of ErbB receptors that the cell expresses; and (ii) the quantity and type of ligands that activate cells expressing ErbB receptors.

Upon activation, each ErbB receptor has the capacity to recruit different intracellular substrates, thus allowing alternative signaling cascades to be activated. Ligand-induced formation of inter-ErbB heterodimers (e.g., ErbB-2-ErbB-4 oligomers) often takes place in preference to ErbB homodimers (e.g., ErbB-4-ErbB-4 oligomers). Heterodimerization is an important process in ErbB signaling. For example, the highly active and oncopotent ErbB-2 receptor to date has no known ligand that directly binds it, although it can be activated in trans through its binding to other ErbB receptors (Tzahar et al., 1997 and 1998).

Typically, ErbBs are activated in a ligand-dependent manner. Cells expressing a particular repertoire of ErbB receptors can be activated in a different manner, depending on the incident ErbB ligands that bind them. For example the ErbB-ligand Epidermal Growth Factor (EGF), strongly activates ErbB1 homodimers, without activating ErbB-4 under normal physiological conditions (Tzahar et al, 1996). In contrast Neuregulin-4 (NRG-4), the subject of the present invention, strongly activates ErbB-2-ErbB-4 heterodimers, weakly activates ErbB4-ErbB4 homodimers and does not activate ErbB1 homodimers. Thus in a scenario where a particular cell expresses ErbB1, ErbB2 and ErbB4, activation by EGF or by NRG-4 can result in very different responses, as different components of the ErbB signaling network are recruited.

The present invention describes the first characterization of NRG-4, a novel member of the ErbB ligand family, whose structure, expression pattern and restrained receptor-binding properties suggest a unique physiological role. Gene-targeting and in vitro studies with recombinant NRG-4 may resolve the presumed distinct biological role of this growth factor and its relationship to other EGF/NRG family ligands. Thus, the present invention exemplifies:

First, the discovery of the first cDNA variant of mouse NRG-4, including the region encoding the EGF-like domain, essential for ErbB-binding.

Second, the isolation and characterization of mouse genomic DNA, which harbors two exons found in the aforementioned mouse cDNA; one of these exons which encodes the invariant amino-terminus of the EGF-like domain. The intron-exon boundary for one of these exons is identical to that found for the prototypical NRG-1 gene, indicating that the two genes are ancestrally related. Should NRG-4 indeed follow the example of the. prototypical NRG-1 gene, then another isoform of the EGF-like domain may still exist, with an alternatively encoded COOH-terminus.

Third, the isolation of the human NRG-4 cDNA gene, highly homologous to the mouse sequence.

Fourth, characterization of NRG-4 binding to ErbB receptors. Numerous strategies were employed to demonstrate that NRG-4 directly binds to the ErbB4 receptor, and preferably activates through ErbB4-ErbB2 heterodimers.

Fifth, the generation and characterization of neutralizing NRG-4 antibodies as a pharmacological tool to block NRG-4 binding through its EGF-like domain.

Sixth, the expression profile of NRG-4, implicating a natural role of this ligand in muscles, the pancreas these finding serving as a spring-board to test natural physiological roles of this ligand that may be of therapeutic benefit.

The very specific and unusually restricted binding profile of NRG-4 may be exploited for both pharmacological and diagnostic purposes.

Traceable synthetic/recombinant NRG-4-tagged molecules can serve as a diagnostic tool in which cells binding NRG-4 can be measured. For example, the oncogenic ErbB2 receptor serves as a marker in breast cancer patients that predicts low chances of remission after standard chemotherapy protocol. However, numerous studies implicate the requirement of ErbB2 to be co-activated along with other ErbBs. Thus, the stratification of sub-groups of breast cancer patients co-overexpressing ErbB2 with different ErbBs is less well defined. A traceable NRG-4-tagged molecule would serve as a sensitive physiological tool to elucidate if these ErbB2 overexpressors also co-overexpress ErbB4.

The extremely limited but specific ErbB-binding profile of NRG-4 can be exploited in the generation of NRG-4-tagged molecules that can specifically target bound drugs to cells with affinity to NRG-4. Of the known ErbB receptors it is shown herein that the EGF-like domain of NRG-4 can only bind with high affinity to cells co-expressing ErbB4 and ErbB2 and perhaps in a lesser extent to cells co-expressing ErbB1 and ErbB4. This extremely limited binding profile can allow the delivery of drugs to a limited repertoire of cells, allowing for smaller drug doses to be used and limiting the chances of generic toxic side effects to take place in patients. For example, patients displaying cancers co-overexpressing ErbB4 and ErbB2 may benefit from a NRG-4-tagged drug delivery vehicle.

The extremely limited but specific ErbB-binding profile of NRG-4 can also be exploited to activate a small repertoire of cells that express high affinity receptors that can be activated by it. Expression of NRG-4 in adult pancreatic and muscle cells indicate that NRG-4 can modulate distinct physiological processes, both in development as well as in the adult. The high conservation between human and mouse NRG-4, particularly within the EGF-encoding domain further implicate an important role of NRG-4 in mammals. These bioactivities may be further exploited for biopharmaceutical purposes.

Thus, the present invention provides for a method of determining a distribution of ErbB-4 receptor in a biological sample. This method is effected by incubating the biological sample with a labeled polypeptide, the polypeptide being at least 50% homologous to at least positions 4-50 of SEQ ID NOs:2 or 15 as determined using BestFit software of the Wisconsin sequence analysis package, utilizing the Smith and Waterman algorithm, where the gap creation penalty equals 8 and gap extension penalty equals 2, to thereby determine the distribution of ErbB-4 receptor in the biological sample.

The present invention further provides for a method of diagnosing a disease, condition or syndrome associated with disregulation of an endogenous protein affecting ErbB-4 receptor activity, the endogenous protein being at least 50% homologous to at least positions 4-50 of SEQ ID Nos:2 or 15 as determined using the BestFit software of the Wisconsin sequence analysis package, utilizing the Smith and Waterman algorithm, where gap creation penalty equals 8 and gap extension penalty equals 2. this method is effected by obtaining a sample from a subject; and incubating the sample with at least one oligonucleotide or oligonucleotide analog of at least 17 bases, the oligonucleotide or oligonucleotide analog capable of hybridizing to a portion of a polynucleotide strand encoding the endogenous protein, to thereby diagnosing the disease, condition or syndrome associated with disregulation of an endogenous protein affecting ErbB-4 receptor activity. The at least one oligonucleotide or oligonucleotide analog preferably comprises a pair of oligonucleotides or analogs specifically hybridizable to the portion of the polynucleotide strand in an opposite orientation so as to direct exponential amplification of at least a portion thereof in a nucleic acid amplification reaction.

According to still another aspect of the present invention there is provided a method of testing whether a genetic disease mapped to 15q25-26 is associated with NRG4. The method according to this aspect of the invention is effected by determining the presence or absence of sequence differences between individuals carrying at least one allele causing the genetic disease and individuals free of the allele, wherein presence of the sequence differences is indicative that the genetic disease mapped to 15q25-26 is associated with NRG4.

Determining sequence differences between individuals typically comprises the use of either a signal amplification method or a direct detection method followed by detection of at least one sequence change.

The signal amplification method according to various preferred embodiments of the present invention may amplify, for example, a DNA molecule or an RNA molecule. Signal amplification methods which might be used as part of the present invention include, but are not limited to PCR, LCR (LAR), Self-Sustained Synthetic Reaction (3SR/NASBA) or a Q-Beta (Qβ) Replicase reaction.

The polymerase chain reaction (PCR), as described in U.S. Pat. Nos. 4,683,195 and 4,683,202 to Mullis and Mullis et al., is a method of increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves the introduction of a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization (annealing), and polymerase extension (elongation) can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

The ligase chain reaction [LCR; sometimes referred to as "Ligase Amplification Reaction" (LAR)] described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method of amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, and ligation amplify a short segment of DNA. LCR has also been used in combination with PCR to achieve enhanced detection of single-base changes. Segev, PCT Publication No. WO9001069 A1 (1990). However, because the four oligonucleotides used in this assay can pair to form two short ligateable fragments, there is the potential for the generation of target-independent background signal. The use of LCR for mutant screening is limited to the examination of specific nucleic acid positions.

The self-sustained sequence replication reaction (3SR) (Guatelli et al., Proc. Natl. Acad. Sci., 87:1874-1878, 1990), with an erratum at Proc. Natl. Acad. Sci., 87:7797, 1990) is a transcription-based in vitro amplification system (Kwok et al., Proc. Natl. Acad. Sci., 86:1173-1177, 1989) that can exponentially amplify RNA sequences at a uniform temperature. The amplified RNA can then be utilized for mutation detection (Fahy et al., PCR Meth. Appl., 1:25-33, 1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo- and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

In the Q-Beta (Qβ) Replicase method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37° C.). This prevents the use of high temperature as a means of achieving specifias in the LCR, the ligation event can be used to detect a mutation at the junction site, but not elsewhere.

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55° C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

The basis of the amplification procedure in the PCR and LCR is the fact that the products of one cycle become usable templates in all subsequent cycles, consequently doubling the population with each cycle. The final yield of any such doubling system can be expressed as: $(1+X)^n=y$, where "X" is the mean efficiency (percent copied in each cycle), "n" is the number of cycles, and "y" is the overall efficiency, or yield of the reaction (Mullis, PCR Methods Applic., 1:1, 1991). If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220,513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method of the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999, 1990)

A similar 3'-mismatch strategy is used with greater effect to prevent ligation in the LCR (Barany, PCR Meth. Applic., 1:5, 1991). Any mismatch effectively blocks the action of the thermostable ligase, but LCR still has the drawback of target-independent background ligation products initiating the amplification. Moreover, the combination of PCR with subsequent LCR to identify the nucleotides at subject positions is also a clearly cumbersome proposition for the clinical laboratory.

The direct detection method according to various preferred embodiments of the present invention may be, for example a cycling probe reaction (CPR) or a branched DNA analysis.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern band RNase protection assays usually require the use of radioactivity and are not amenable to automation. Recently devised techniques have sought to eliminate the use of radioactivity and/or improve the sensitivity in automateable formats. Two examples are the "Cycling Probe Reaction" (CPR), and "Branched DNA" (bDNA).

The cycling probe reaction (CPR) (Duck et al., BioTech., 9:142, 1990), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA (bDNA), described by Urdea et al., Gene 61:253-264 (1987), involves oligonucleotides with branched structures that allow each subject oligonucleotide to carry 35 to 40 labels (e.g., alkaline phosphatase enzymes). While this enhances the signal from a hybridization event, signal from non-specific binding is similarly increased.

The detection of at least one sequence change according to various preferred embodiments of the present invention may be accomplished by, for example restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis or Dideoxy fingerprinting (ddF).

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet mutationwithin specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

For detection of single-base differences between like sequences, the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis).

Single point mutations have been also detected by the creation or destruction of RFLPs. Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), Nucleic Acids and Molecular Biology, vol. 2, Springer-Verlag, Heidelberg, 1988). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167, 1987). Recently, endonucleases encoded by group I introns have been discovered that might have greater than 12 base-pair specificity (Perlman and Butow, Science 246:1106, 1989), but again, these are few in number.

If the change is not in a recognition sequence, then allele-specific oligonucleotides (ASOs), can be designed to hybridize in proximity to the mutated nucleotide, such that a primer extension or ligation event can bused as the indicator of a match or a mis-match. Hybridization with radioactively labeled allelic specific oligonucleotides (ASO) also has been applied to the detection of specific point mutations (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes (Vogelstein et al., N. Eng. J. Med., 319:525-532, 1988; and Farr et al., Proc. Natl. Acad. Sci., 85:1629-1633, 1988), and gsp/gip oncogenes (Lyons et al., Science 249:655-659, 1990). Because of the presence of various nucleotide changes in multiple positions, the ASO method requires the use of many oligonucleotides to cover all possible oncogenic mutations.

With either of the techniques described above (i.e., RFLP and ASO), the precise location of the suspected mutation must be known-in advance of the test. That is to say, they are inapplicable when one needs to detect the presence of a mutation within a gene or sequence of interest.

Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al., Proc. Natl. Acad. Sci. USA 88:8405, 1991). CDGE requires that gels be performed under different denaturant conditions in order to reach high efficiency for the detection of mutations.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE cdetect mutations in relatively small fragments of DNA therefore scanning of large gene segments requires the use of multiple PCR products prior to running the gel.

Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

According to a presently preferred embodiment of the present invention the step of searching for the mutation or mutations in any of the genes listed above, such as, for example, the reduced folate carrier (RFC) gene, in tumor cells or in cells derived from a cancer patient is effected by a single strand conformational polymorphism (SSCP) technique, such as cDNA-SSCP or genomic DNA-SSCP. However, alternative methods can be employed, including, but not limited to, nucleic acid sequencing, polymerase chain reaction, ligase chain reaction, self-sustained synthetic reaction, Qβ-Replicase, cycling probe reaction, branched DNA, restriction fragment length polymorphism analysis, mismatch chemical cleavage, heteroduplex analysis, allele-specific oligonucleotides, denaturing gradient gel electrophoresis, constant denaturant gel electrophoresis, temperature gradient gel electrophoresis and dideoxy fingerprinting.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization-A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Materials:

EGF (human, recombinant) was purchased from Boehringer Mannheim. Recombinant human NDF"1177-246 (NRG-1-β1) was obtained from Amgen (Thousand Oaks, Calif.). Iodogen and bis(sulfosuccinimidyl) suberate ($BS^3$) were from Pierce. Monoclonal antibodies (mAbs) to ErbB proteins (Chen et al., 1996; Klapper et al., 1997) were used for immunoprecipitation. The composition of buffered solutions was described (Tzahar et al., 1994). Recombinant soluble extracellular domains of the four ErbB proteins (denoted IgB-1 through 4) (Chen et al., 1996), in the form of fusion proteins containing the Fc portion of human immmunoglobulin G (IgG) were harvested from serum-free conditioned media of transfected HEK-293 human embryonic kidney cells. The PY20 antibody was purchased from Santa Cruz Biotechnology. A mAb to the active form of the MAP kinase (Yung et al., 1997) was a gift from R. Seger (of the Weizmann Institute, Israel)

Peptide Synthesis:

The mouse EGF-like domain of NRG-4 (residues 4 to 50, SEQ ID NO:2) was synthesized on an Applied Biosystems (ABI) 430A peptide synthesizer using standard tert-butyloxycarbonyl (t-Boc) chemistry protocols as described (Barbacci et al., 1995). Acetic anhydride capping was employed after each activated ester coupling. The peptide was assembled on phenylacetamidomethyl polystyrene resin using standard side chain protection, except for the use of t-Boc-Glu(O-cyclohexyl) and t-Boc-Asp(O-cyclohexyl). The peptide was deprotected using the "Low-High" hydrofluoric acid (HF) method (Tam et al., 1983). The crude HF product was purified by reverse phase HPLC (C-18 Vydac, 22.times.250 mm), diluted without drying into folding buffer (1 M urea, 100 mM Tris, pH 8.0, 1.5 mM oxidized glutathione, 0.75 mM reduced glutathione, 10 mM methionine), and stirred for 48 h at 4 C. The folded, fully oxidized peptide was purified from the folding mixture by reverse phase HPLC, and characterized by electrospray mass spectroscopy. A single HPLC peak with an averaged molecular mass (Mr) of 5371.50 was displayed by the reduced peptide prior to folding. This mass is in agreement with the theoretical Mr (5371.20). The folded and oxidized peptide displayed a slightly lower averaged molecular mass of 5366.88.

Database Searches:

EST databases were scanned for homology to the EGF-like domain of NRG-1β (NDF-β) by Blast and Smith-Waterman algorithms (Samuel & Altschul, 1990; Smith & Waterman, 1981) using both a Unix-interfaced GCG server and a Bioaccelerator device (Compugen, Israel). Obtained clones (Accession numbers AA238077 (mouse) and AI743 118 (human)) were sequenced bi-directionally to both confirm fidelity of published sequences and to extend the sequence of the clones beyond that published in the EST databases. In the case of the human EST clone which contained an apparent insert in the open reading frame, PCR primers were generated in order to pull out a variant without this insert by means of RT-PCR (see below).

Genomic Screen:

PCR primers designed to amplify predicted exon-6 of NRG-4 were synthesized and used to screen a P1 genomic library derived from mouse strain 129. A single positive P1 clone was identified, subsequently subcloned by shotgun ligation and identification of Exon-6 positive bluescript integrants. One such vector, harboring a 10 Kb insertion was mapped and partially sequenced revealing Exon-5 and Exon-6 sequences.

RT-PCR:

Total RNA was extracted from T47D and MCF-7 human breast cancer cell lines (TRIZOL Reagent). 5 μg of total RNA was used as a template to derive mRNA derived cDNA, using 500 μg/ml Oligo-(dT)12-18 as a primer (Gibco BRL superscript kit; Oligo-dT). Forward 5'-CCTACTCTCTTGAC- CAAGAATGAAAC-3' (SEQ ID NO:16) and reverse 5'-AAT-GATTTGGTTCACTTTGACG-3' (SEQ ID NO:17) oligonucleotides were synthesized as primers to amplify NRG-4 from the cDNA libraries, amplifing with Roche Expand™. High Fidelity PCR amplification system, using company's recommended amplification conditions and 68 C annealing/extension temperature. PCR products were run on a 1% agarose gel. Bands of expected mobility were identified from both T47D and MCF-7 cells, were extracted and subcloned into pGEMT (Promega) before sequencing. The human NRG-4 sequence published represents identical findings from two independent PCR reactions.

Northern Blot:

A Northern blot filter was purchased from Clontech (MTN Blot #7760-1), each lane containing approximately 2 .mu.g of poly(A).sup.+purified mRNA from healthy human tissues and run on a denaturing 1.2% formaldehydelagarose gel Hybridization to cDNA probes to mouse NRG-4 and human .beta.-actin were performed with "ExpressHyb"™ (Clontech) using the protocol provided by the manufacturer. Probing with a human amylase cDNA probe was performed by standard techniques. After each hybridization, blots were washed at room temperature for 40 minutes with several changes of low stringency wash solution (2.times.SSC, 0.05% SDS) and then with at least two changes of high stringency buffer (0.1.times.SSC, 0.1% SDS) at 50.degree. C. for 40 minutes.

Lysate Preparation for Western Blot Analyses:

For receptor activation studies, derivatives of the 32D cell line were resuspended in phosphate-buffered solution (PBS) and incubated at 22 C for 15 minutes before adding growth factors and incubating for five minutes at 37 C. Cells were then pelleted and lysed in ice cold solubilization buffer [50 mM Tris-HCl pH 7.5, 150 mM NaCl, 1% Nonidet-P40, 0.5% Na-deoxycholate, 0.1% sodium dodecyl sulfate (SDS), 1.5 mM EDTA, 1.5 mM $MgCl_2$, 2 mM Na-orthovanadate, 1 mM phenylmethylsulfonyl fluoride (PMSF), 10 .mu.g/ml aprotinin and 10 .mu.g/ml leupeptin] and left on ice for 15 minutes. The whole cell extract was then cleared by centrifugation (12,000.times.g for 10 minutes at 4 C), immediately boiled in reducing gel sample buffer, and resolved by 10% SDS PAGE before being transferred onto nitrocellulose. Filters were blocked in TBST buffer (0.02 M Tris-HCl pH 7.5, 0.15 M NaCl, 0.05% Tween-20) containing 1% milk for 40 minutes at 22 C, blotted with primary antibodies in TBST overnight at 4 C, followed by conjugation with a secondary antibody linked to horseradish peroxidase and subsequent detection by chemiluminescence (Amersham Corp.).

Radiolabeling of Ligands, Covalent Crosslinking and Ligand Displacement Analyses:

Growth factors were labeled with Iodogen (Pierce) as described (Karunagaran et al., 1995). Chemical crosslinking to Chinese Hamster Ovary (CHO) cells engineered to express different ErbB combinations have been performed essentially as described (Tzahar et al., 1996). Briefly, radiolabeled ligands (at 100 ng/ml) were incubated for 2 hours with cell monolayers at 4 C. The chemical crosslinking agent BS.sup.3 (1 mM) was then added and the cells were further incubated for 45 minutes at 22 C. Mouse antibodies were first coupled to rabbit anti-mouse IgG and to protein A-Sepharose beads, and then they were incubated with cell extracts for 2 hours at 4 C. Immunoprecipitated complexes were then washed three times with ice-cold SBN buffer (1% NP-40; 150 mM NaCl; 10% Glycerol; 1 mM EGTA, in 50 mM Tris-HCl, pH 7.4; 1 ml per wash) prior to heating (5 minutes at 95 C) in gel sample buffer, resolution by gel electrophoresis, transfer to nitrocellulose and autoradiography. For crosslinking with IgBs, after co-incubation of IgB-containing conditioned media with radiolabeled ligands, complexes were immunoprecipitated directly with Sepharose-protein A beads. For ligand displacement analyses, cell monolayers were washed once with binding buffer, and then incubated for 2 hours at 4 C with radiolabeled NRG-162 (5 ng/ml) and various concentrations of unlabeled ligands, as indicated. Non-specific binding was determined in the presence of a 100-fold molar excess of the unlabeled ligani. Cells were then washed, lysed in a solution containing 0.1 M NaOH and 0.1% SDS, and radioactivity determined by use of a gamma counter.

Antibody Generation and Screening:

Two rabbits (#3919 and #3920) were immunized against the refolded synthetic peptide encoding the mouse NRG-4 EGF-like domain in a protocol of five injections, using 10 μg/rabbit of peptide for each injection along with Freund's complete adjuvant for the first injection and incomplete adjuvant for subsequent injections. Cleared serum was tested for binding to NRG-4 in the following experiment: Serum from the two rabbits as well as pre-immune serum (#3919), a non specific rabbit antiserum (anti-Erk-1 beta; a gift from Dr. Ronny Seger, the Weiznann Institute) and IgB1 conditioned medium were pre-adsorbed onto protein-A sepharose beads for 30 minutes at 4 C in 1 ml and 10 μl of serum/conditioned medium. Beads were then washed three times in HNTG and then blocked in HNTG+0.1% BSA at 4 C for 30 minutes. Pellets were spun down and resuspended in 0.2 ml HNTG along with 5 μl of .sup.125I-radiolabeled EGF or NRG-4, where they were incubated for 2 hours at 4 C, then washed four times in HNTG, boiled in protein sample buffer and resolved by 7.5% SDS PAGE. Gels were dried and signals viewed using a phosphorimager (Fugi).

Cell Proliferation Assays:

The establishment of a series of interleukin 3 (IL-3)-dependent 32D myeloid cells expressing all combinations of ErbB proteins has been described (Alimandi et al., 1997; Pinkas-Kramarski et al., 1996; Shelly et al., 1998). Cells were maintained in RPMI medium with 10% fetal bovine serum (FBS) and dilute IL3-containing conditioned medium. Prior to proliferation assays, cells were washed three times in RPMI/FBS and plated (5.times.10.sup.5 cells/ml; 0.1 ml/well) into 96-well flat-bottomed plates with the indicated liconcentrations or with IL-3 (1:1000 dilution of conditioned medium). Cell survival was determined 24 hours later, or after the indicated time intervals, by MTT assay, as previously described (Mosman, 1983). MTT (0.05 mg/ml) was incubated with the analyzed cells for 2 hours at 37 C. Living cells can transform the tetrazolium ring into dark blue formazan crystals, that can be quantified by reading the optical density at 540-630 nm after lysis of the cells with acidic isopropanol.

Experimental Results

Identification of a Candidate Novel ErbB Ligand:

With the assumption that there may still exist novel ErbB-specific ligands it was decided to search for new family members by homology. The recent explosion of DNA sequencing data added to DNA databases, largely resultant from the Human Genome Project initiative, offers scanning of these data for novel transcripts coding ligands with homology to the ErbB-3- and ErbB-4-specific ligand, NRG-1 (NDF). The motif $CX_7CXNGGXCX_{13}CXCX_3YXGXRC$ (SEQ ID NO:18), conserved in most isoforms of NRG-1, was used to scan available new DNA sequences. An expressed sequence tag (EST) clone originating from a mouse liver cDNA library (accession number AA238077) was identified, its sequence encoding an EGF-like domain sharing 32% identity with the NRG-1β isoform (Wen et al., 1992). This clone was obtained and fully sequenced, its presumed translation product encoding a protein of 115 amino acids (FIG. 1*a*, SEQ ID NOs:1 and 2). Hydropathy analysis using the Kyte-Doolitle algorithm (Kyte & Doolittle, 1982) supports the existence of a transmembrane domain (FIG. 1*b*) characteristic to most NRG isoforms (Marchionni et al., 1993; Wen et al., 1994). Conspicuously, this protein sequence lacks a hydrophobic amino-terminal stretch, commonly found in signal peptide motifs, important in sequestering proteins to traverse the plasma membrane. Most isoforms of NRG-1 also lack consensus signal peptide sequences, but they carry an apolar N-terminal sequence thought to allow transmembrane orientation of the precursor molecule. The predicted extracellular domain of the precursor protein includes the EGF-like domain, whose primary structure displays the entire structural motifs characteristic to the EGF/NRG family (FIG. 1*c*). The putative cytoplasmic domain of the precursor protein is relatively short and contains one potential site for N-glycosylation. Two additional sites are located at the probable ectodomain.

Alignment of the EGF-like domains of all known ErbB-specific ligands of mammalian origin indicated that the novel transcript encodes a new member of this family (FIG. 1*c*). Its characteristic six extracellular cysteine residues and their conserved spacing predict the existence of the three disulfide bridges, denoted as A, B and C, that are the landmark of all EGF-like peptides. Besides the six conserved cysteine residues, the new EGF-like domain shares very high homology with other members of the NRG family, including a glycine at position 21 (Gly-21), Gly42 and Arg44, along with many semi-conserved residues. Of note, the expected B loop of the protein, like the loops of EGF and NRG-2, is shorter by three residues. Except for the EGF-like domain and the transmembrane topology of the novel predicted protein, it shares no significant sequence homology or structural motifs with other ErbB ligands.

EST-derived clones on occasion can be prone to sequence artifacts. The EGF-encoding domains of ErbB-ligands can alone elicit ErbB-binding, It was, therefor, decided to examine in more detail sequences encoding in particular the EGF-encoding domain of this putative novel ligand, in the very least to confirm the identity of this domain. Two alternative strategies were employed to test this.

The first, was to isolate the genomic locus of the novel ligand, using a probe encoding the EGF-like domain. A P1 clone derived from a mouse strain 129 genomic library was isolated, from which plasmid sub-clones of the P1 vector were generated by shotgun ligation; these fragments being once again screened by hybridization for the EGF-like domain encoding probe. The largest of these sub-clones was characterized more fully. A detailed restriction map was generated and the clone was partly sequenced (FIG. 1*d*). Two exons were identified, the latter encoding the 5' component of the EGF-like domain and was arbitrarily designated as Exon-6, corresponding to Exon-6 of the prototypical NRG-1 genomic locus. Exons 5 and 6 share 100% sequence identity with the corresponding sequenced mouse EST-cDNA, confirming the quality of the EST clone. Significantly, the intron-exon boundaries of Exon 6 for both NRG-1 and the novel gene are identical, supporting that these genes are derived from a common ancestor, and indicates that the novel ligand is encoded by a new variant of the Neuregulin gene family. As this data supports that the novel ErbB-ligand is a Neuregulin, it was named Neuregulin4 (NRG-4).

Second, by method of RT-PCR, a human NRG-4 homologue was isolated and sequenced (FIG. 1*e*). Human primers were initially derived from a second EST clone AI743 118, which shares, in part, identical sequence to the reverse transcribed and subcloned human derived NRG-4 isoform presented herein, but also an insertion that disrupts the encoded EGF-domain sequence.

Using the oligonucleotides as RT-PCT primers as described, 10 RT-PCR products were subcloned from MCF7 and T47D cells. Eight of the ten PCR products harbored inserts within the EGF-encoding domain, resulting in disruption of the EGF domain and in all cases, truncation of the predicted amino-acid sequences with the co-current loss of a transmembrane binding motif. A similar insertion was found in the EST clone #AI743118. The functional relevance, if any, of these optionally alternatively spliced isoforms. Should they indeed represent mature mRNA, the predicted protein products would not activate ErbB receptors. It is hypothesize that these transcripts are either partially processed RNAs or if not, may encode proteins that would inhibit ErbB binding.

The predicted translation products for human and mouse NRG-4 share 78% overall identity and 91% identity within the EGF-like encoding domain. All of the differences in the EGF-like domain were encoded entirely by Exon 6, with exact matching amino acid sequences at the COOH terminal. This conserved primary structure demonstrates that these two genes encode the same isoform of the NRG-4 EGF-like domain for both species. Should an other isoform of the EGF-like domain exist for NRG-4 as does for NRG-1, remains to be resolved. The tightly conserved primary structure particularly of the EGF-like domain between mouse and human NRG-4 also demonstrates that selective evolutionary pressure has maintained the integrity of this locus, supportive that this gene plays essential(s) role in mammalian development and/or maintenance.

Figure 7:
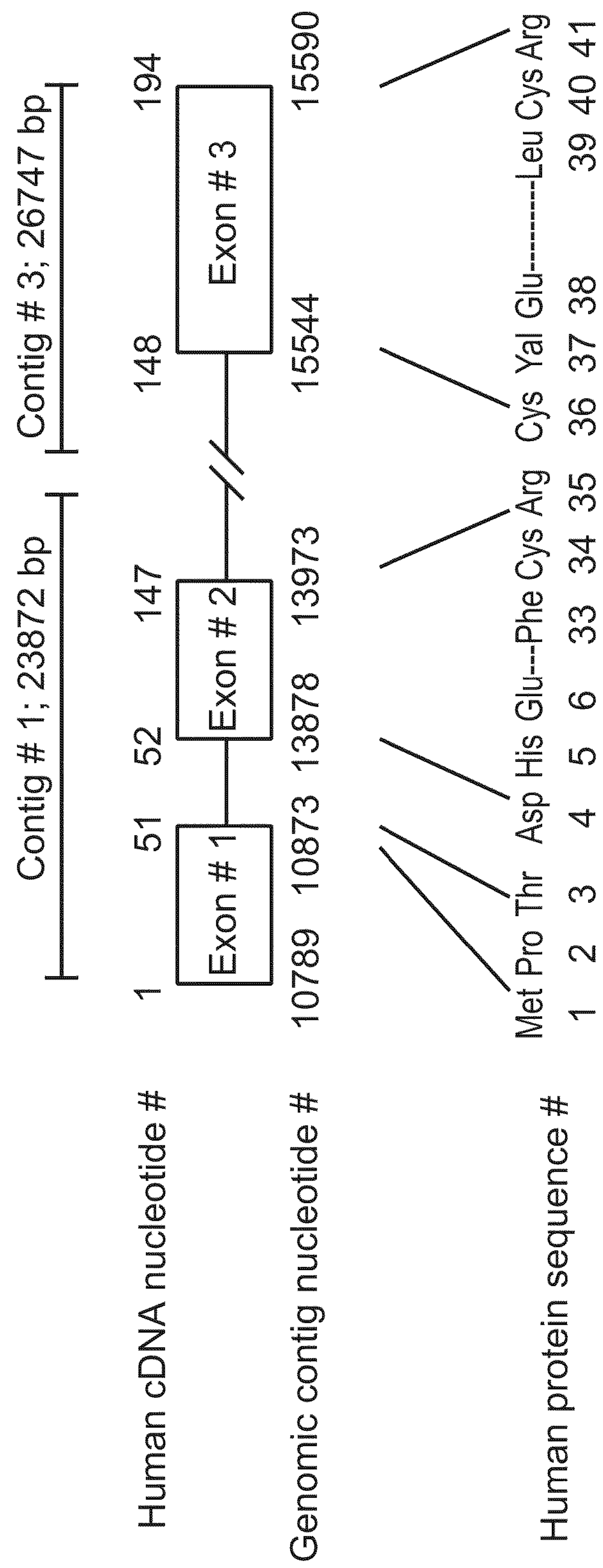
FIG. 7 shows a schematic representation of the Exon/Intron structure of the human NRG-4 gene (see SEQ ID NOs:19 and 20 for Contigs #1 and 3).

A number of overlapping genomic HTG sequences (NCBI) were found to harbor NRG-4 sequence by method of BLASTN and TBLASTN sequence search analyses. These overlapping HTG sequences were all fragmented and disordered. These sequences were combined, disassembled and re-assembled into numerous larger sized DNA contigs, using the SEQUENCHER software package. Two of these contigs, named Contig #I (SEQ ID NO: 19) and Contig #3 (SEQ ID NO:20) harbor the first three exons encoding human NRG-4 cDNA (see FIG. 7). These exons encode the initiating Methionine (Met 1) residue, the entire EGF-domain and presumed transmembrane sequences. The cDNA and genomic exon sequences share about 100% identity. This contig maps to human chromosome 15 exactly corresponding to a Short Sequence Tag of accession number #SHGC-107194, approximately human genomic locus 15q25-26.

Numerous hereditary diseases and cancer-susceptible loci have been found to map to this locus. For example, a genetic susceptibility locus to Insulin Dependent Diabetes Mellitus Type 3 (IDDM3) maps closely to NRG-4, thus implicating NRG-4 as a target gene involved/co-involved in this disease. The publication of the human sequence and its exact mapping to this locus will thus allow genetic linkage of this gene with related hereditary disease, such as for the candidate example of IDDM3.

Figure 2:
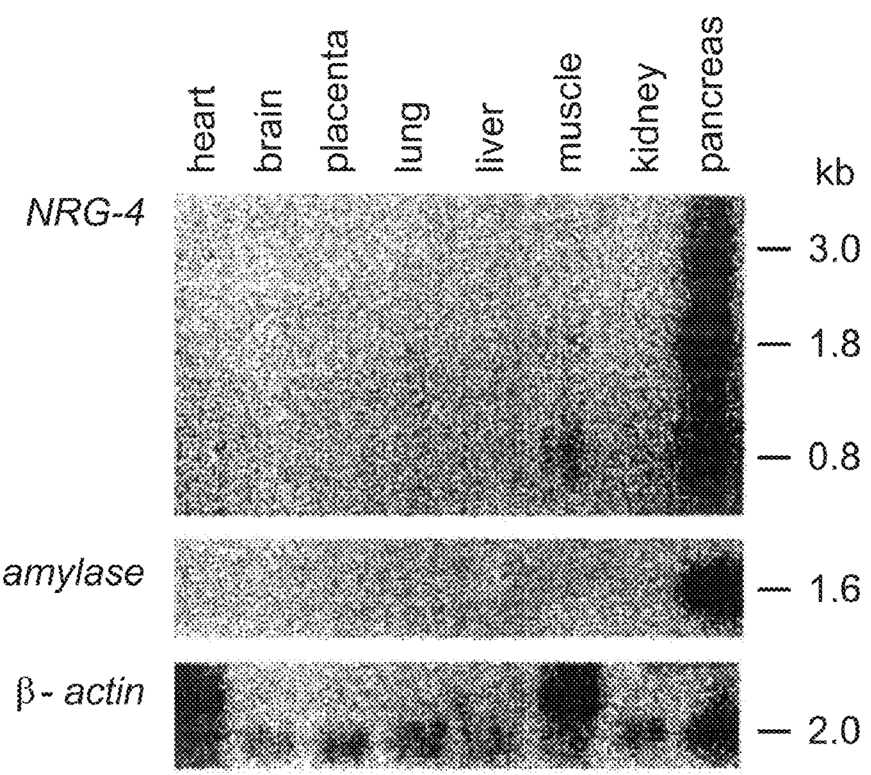
FIG. 2 shows a northern blot analysis of NRG-4 expression in human tissues. Poly(A)-containing RNA from the indicated human tissues (2 μg per lane) was analyzed using a nitrocellulose filter purchased from Clontech (San Diego, Calif.). The blot was hybridized with a full-length mouse NRG-4 cDNA probe radiolabeled using the Klenow fragment of DNA polymerase I and random hexamers as primers. Following autoradiography, the filter was stripped of radioactivity and re-probed sequentially with pancreas and muscle markers, alpha-amylase-2 and beta-actin, respectively. Molecular weights of marker molecules are indicated in kilobases (kb). Note that beta-actin probe also hybridized with a larger molecular weight isoform present in heart and in skeletal muscle.

Tissue-specific Expression of the Novel Transcript:

Expression analysis was performed to help elucidate the possible target sites of NRG-4 activity. Northern blot analysis of mRNA isolated from different human adult tissues revealed moderate expression of the NRG-4 transcript in skeletal muscle and high levels in the pancreas (FIG. 2). Other tissues, including brain and placenta, two rich sources of many different growth factors, displayed very low expression, if any. Three discernible molecular weight species (0.8, 1.8 and 3.0 kilobases) were detectable in pancreas and in muscle, indicating the existence of several mRNA isoforms, the smallest band consistent in size with the NRG-4 clone described in this study.

The EGF-Like Domain of NRG-4 Stimulates Proliferation of ErbB-4-Expressing Cells:

To test the prediction that the novel transcript encodes an ErbB-specific ligand, the corresponding full-length EGF-like domain (residues 4-50, FIG. 1*a*, SEQ ID NO:2) was synthesized, denatured and refolded to allow proper disulfide bridging. This method has been used before to synthesize functionally active derivatives of other EGF-like growth factors (Barbacci et al., 1995; Lin et. al., 1988; Shelly et al., 1998). A series of derivatives of the 32D cell line engineered to express different ErbB receptors or their combinations has been previously described (Pinkas-Kramarski et al., 1996; Shelly et al., 1998). The myeloid 32D parental cells require cytokine stimulation, such as interleukin 3 (IL3) for their growth, and were chosen because they lack endogenous ErbB expression. Signaling through different ErbB-receptors can replace the IL3-dependent mitogenicity and survival for these cell lines, and hence this system provides a sensitive means to detect ligand-induced growth signals, which are conveniently measured as a function of cellular metabolic activity by using the [3-(4,5-dimethylthiazol-2-yl)-2,5-diphenyl]tetrazolium bromide (MTT) assay (Mosman, 1983).

Cells singly expressing ErbB-1, ErbB-2 or ErbB-3 (denoted D1, D2 or D3, respectively) did not respond to the synthetic novel peptide in a 24-hour dose-response assay, although responses to EGF (D1 cells), an ErbB-2-stimulatory monoclonal antibody [D2 cells, (Klapper et al., 1997)], or IL-3 (D3 cells) were retained (FIG. 3A, and data not shown). The latter cell line is not responsive to NRGs due to the defective kinase of ErbB-3. However, ErbB-4 expressing cells (D4), exhibited a modest dose-dependent mitogenic response in comparison to its counterpart NRG-1β control. Because different heterodimeric complexes of ErbB proteins can diversify and enhance signaling by EGF-like ligands (Cohen et al., 1996; Pinkas-Kramarski et al., 1996; Riese et al., 1995), cells co-expressing two ErbB proteins (for example D12 cells co-express ErbB-1 and ErbB-2) were also tested for NRG-4-induced mitogenicity. Of the tested combinations, namely: D12, D13, D23 and D24 cells, a cell line expressing a combination of ErbB-4 with ErbB-2 (D24 cells) was the only line that responded mitogenically to the novel peptide (FIG. 3A). Notably, co-overexpression of ErbB-1 and ErbB-2 resulted in a relatively high basal proliferation activity, but these cells still responded to EGF (FIG. 3B). Additionally, in cells co-overexpressing ErbB-2 and ErbB-4, NRG-1 and the novel ligand were almost equipotent (compare D4 and D24 panels in FIG. 3A), indicating that ErbB-2 can enhance the mitogenic effect of the novel ligand, as it does for other ErbB ligands (Graus-Porta et al., 1995; Karunagaran et al., 1996; Wang et al., 1998).

A long-term cell survival assay confirmed the ability of the novel growth factor to stimulate ErbB-4. This assay examined the ability of added growth factors to sustain survival of certain 32D derivatives in the absence of IL-3. As in the dose-response experiments, the novel synthetic peptide only stimulated the survival of the two ErbB-4-expressing cell lines we examined, namely D4 and D24 cells (FIG. 3*b*). Also similar to the short-term dose response assay, stimulation of D24 cells was more robust, and akin to the NRG-1-treated controls than was the response of D4 cells. These data indicate that the NRG-4 growth factor can exert a weak proliferative signal through ErbB-4 alone, but co-expression of ErbB-2 with ErbB-4 allows a superior mitogenic response, as it does in the case of NRG-1 (Wang et al., 1998). On the basis of the ability of the NRG-4 derived synthetic peptide to mediate a biological effect through one of the Neuregulin receptors, this data further supports that it is a Neuregulin, namely Neuregulin-4 (NRG-4).

NRG4 Recognizes and Activates ErbB-4:

To elucidate the molecular interactions pertaining to NRG-4 signaling, several different approaches were employed to test specific binding of this growth factor to the four ErbB proteins.

In the first assay, binding studies in a cell-free system were performed with recombinant soluble forms of all four ErbB proteins. The soluble proteins, denoted IgB-1 through 4, consist of a dimeric fusion between the extracellular domain of the corresponding ErbB and the Fc portion of a human immunoglobulin G (Chen et al., 1996). NRG-4, EGF and NRG-1β were radiolabeled with $^{125}$I, incubated with the soluble receptors, and then irreversibly bound to the IgBs using the $BS^3$ covalent crosslinking reagent.

As expected for the controls, a strong signal was detected for EGF binding to IgB-1 in contrast to NRG-1β, which bound strongly to IgB-3 and IgB-4, but no ligand bound to IgB-2 (FIG. 4*a*). In comparison to NRG-1, $^{125}$I-NRG-4 bound to the soluble form of ErbB-4 (IgB-4) only weakly, with low or no binding to the other IgB proteins (FIG. 4*a*).

To confirm specificity of the covalent crosslinking assay unlabeled NRG-4 was co-incubated, at 100-fold molar excess, with the radioactive ligand and efficient displacement from IgB-4 was observed (lower panel of FIG. 4*a*). Thus, consistent with the ability of NRG-4 to induce growth and survival of ErbB-4-expressing cells, but not cells singly expressing the other three ErbB receptors, this ligand recognized only ErbB-4 (IgB4) in solution.

To test the prediction that NRG-4 can recognize a surface-expressed ErbB-4, but no other membrane-bound ErbB protein, a Chinese Hamster Ovary (CHO) cell line was employed. These cells express low amounts of ErbB-2, but no other ErbB receptor, and accordingly failed to bind NRG-4 or any other Neuregulin [(Tzahar et al., 1996) and data not shown]. CHO cells were transfected with plasmid vectors directing expression of ErbB-4, or co-transfected with an ErbB-4 plasmid together with vectors expressing one of the three other ErbB proteins. Two days later, cells were incubated with .sup.125I-NRG-4, or with a radiolabeled NRG-1 as control, and subsequently the formed ligand-receptor complexes were stabilized by using a covalent crosslinking reagent. Immunoprecipitation of the expressed ErbB proteins allowed analysis of the covalently held complexes. Expression of ErbB-4 alone conferred to CHO cells the ability to form complexes with NRG-4, as well as with NRG-1 (FIG. 4*b*). In line with the lower mitogenic activity of NRG-4, the covalent crosslinking signal obtained with this ligand was weaker than that observed with a radioactive NRG-1. Nevertheless, both monomers and dimers of ErbB-4 were formed by the two ligands (detection of NRG-4-containing dimers required longer film exposures). Co-expression of ErbB-1 or ErbB-3 did not significantly affect the radioactive signals, but in the case of ErbB-2 an enhancement effect was observed with NRG-1.

The ability of anti-ErbB-1 and anti-ErbB-2 antibodies to precipitate NRG-4-labeled monomeric and dimeric receptor species (FIG. 4B) is probably due to co-immunoprecipitation of ErbB-4 and it indicates the existence of NRG-4-promoted heterodimers with ErbB-1 and ErbB-2. Interestingly, ErbB-3 largely escaped heterodimerization with ErbB-4 following binding of NRG-1 or NRG-4.

Taken together, the biological effects of NRG-4 and its complex formation with ErbB-4 implied not only specificity of recognition, but also weaker interaction relative to NRG-1. To quantify the interaction, a ligand displacement analysis on ErbB-4-expressing CHO cells was undertaken. The ability of unlabeled NRG-4 to displace surface-bound radiolabeled NRG-1β was compared with that of unlabeled NRG-1. The results of this experiment indicated an approximately 8-fold lower binding affinity of NRG-4 to ErbB-4 (FIG. 4*c*). While NRG-1 bound with an apparent affinity that lies in the low nM range, NRG-4 displayed an apparent approximate kDa of 20 nM. In conclusion, NRG-4 specifically binds to ErbB-4 with an affinity is lower than that of NRG-1β. Because it was previously reported that relative to NRG-1β the alpha isoform displays a 5 to 8-fold lower affinity to both ErbB-3 and ErbB-4 (Tzahar et al., 1994), it is conceivable that NRG-4 and NRG-1α bind to ErbB-4 with similar affinities.

Evidently, NRG-4 binds to ErbB-4 and mediates cell proliferation through activation of this receptor. Because other ErbB ligands stimulate cell growth via tyrosine phosphorylation of their respective receptors and activation of the intervening mitogen-activated protein kinase (MAPK) cascade, these two signaling steps were tested in NRG-4-responsive myeloid cells expressing ErbB-4 (D4 and D24 cell lines). Cells were stimulated with 100 ng/ml of activating ligand for five minutes, followed by lysis and analysis by immunoblotting. NRG-4 stimulated phosphorylation of the 180-kDa ErbB receptors in D4 and in D24 cells with an accompanying activation of MAP-kinase (Erk-1 and Erk-2) also detected (FIG. 5). In contrast to these two cell lines, and consistent with the growth and binding assays, NRG-4 at doses as high as 1 μg/ml, did not stimulate the other 32D cell lines (D1, D2, D3, D12, D13, and D23 cells). These results further support the conclusion that NRG-4 is a bona fide ligand of the ErbB receptor family that selectively interacts with receptor complexes containing ErbB-4.

Figure 6:
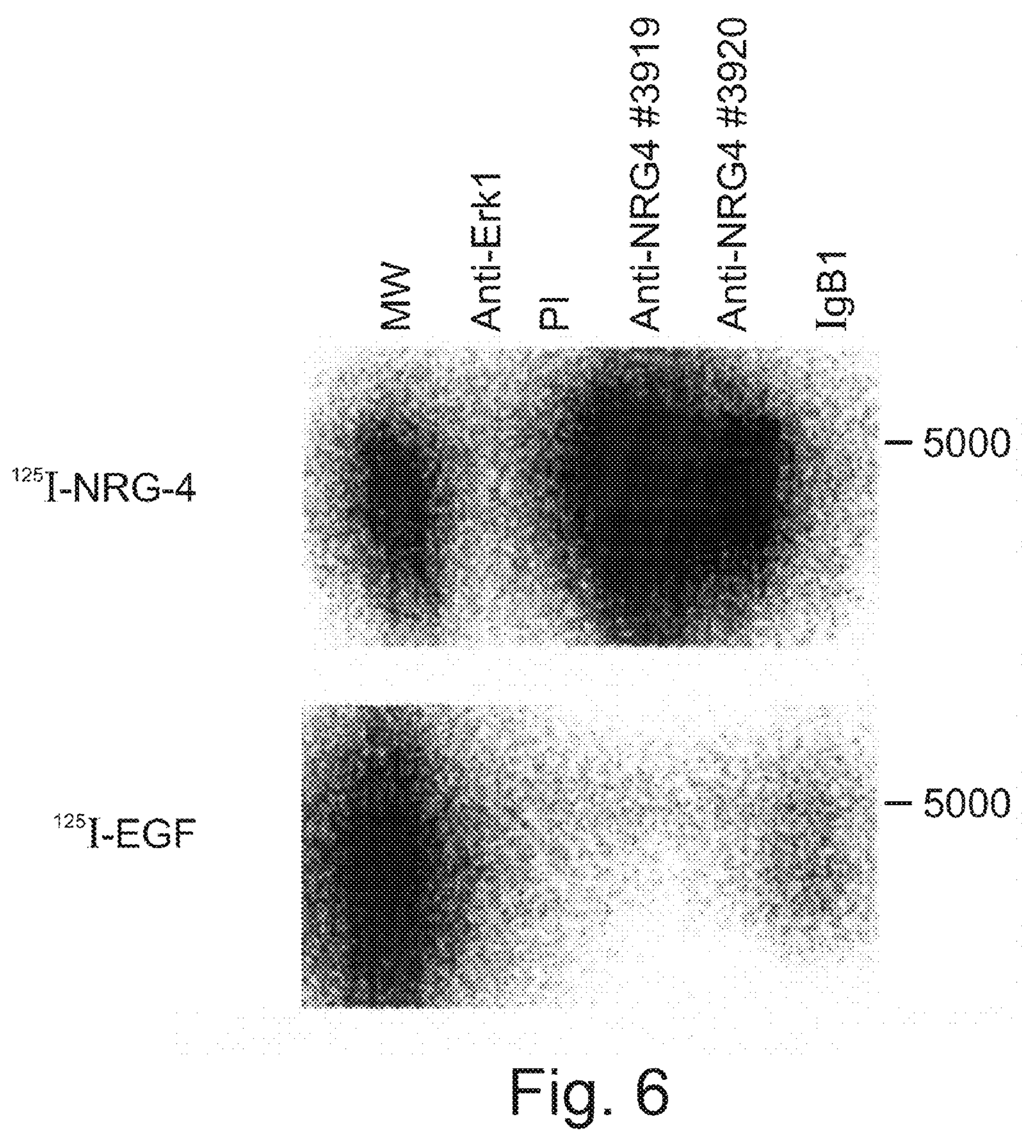
FIG. 6 shows that antibodies generated against the refolded EGF-like domain of NRG-4 Neutralize ligand function. Synthetic refolded NRG-4 peptide was injected into two rabbits by standard adjuvant protocol. After four repeat injections, antisera were collected and tested for specificity by its binding to radiolabeled NRG-4 For non-specific ligand control, radiolabeled EGF was also tested for binding. Hot ligand was separately incubated with sera generated from the two rabbits, along with for controls, pre-immune serum from the first rabbit (#3919), serum generated against a non-relevant epitope (anti-Erk-1) and IgB1 to act as a positive control to demonstrate 1251-EGF activity. These results demonstrate that the two anti-sera are extremely potent and specific blockers of the NRG-4 EGF-like domain. These antibodies therefore will compete with NRG-4 ligand binding to ErbB receptors.

Neutralizing Antibodies to Block NRG-4:

Neutralizing antibodies against the EGF-domain of NRG-4 were prepared. Such antibodies are particularly useful as they can block NRG-4 binding to its target receptor and can therefore be utilized in a pharmaceutical context. Synthetic refolded NRG-4 peptide was injected into two rabbits by standard adjuvant protocol. After four repeat injections, antisera were collected and tested for specificity by its binding to radiolabeled NRG-4. For ligand control, radiolabeled EGF was also tested for binding. Hot ligand was separately incubated with sera generated from the two rabbits, along with for controls, pre-immune serum from one of these rabbits, serum generated against a non-relevant epitope (anti-Erk-1) and IgB1 to act as a positive control to demonstrate 125-I EGF activity (FIG. 6). These results demonstrate that the two anti-sera are extremely potent and specific blockers of the NRG-4 EGF-like domain. These antibodies therefore will compete with NRG-4 ligand binding to ErbB receptors.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Alimandi M, Wang L-M; Bottaro D, Lee C-C, Angera K, Frankel M, Fedi P, Tang F, Tang C, Lippman M and Pierce J H. (1997). EMBO J., 16, 5608-5617.
2. Barbacci E G, Guarino B C, Stroh J G, Singleton D H, Rosnack K J, Moyer J D and Andrews G C. (1995). J. Biol. Chem., 270, 9585-9589.
3. Ben-Baruch, N. & Yarden, Y. (1 994). Proc. Soc. Exp. Biol. & Med, 206, 221-7.
4. Ben-Baruch N, Alroy I and Yarden Y. (1998). Hormones and growth factors in development and neoplasia. Dickson R B and Salomon D S (eds). Kulwer Academic Publishers: Boston, pp. 145-168.
5. Burden S and Yarden Y. (1997). Neuron, 18, 847-855.
6. Busfield S M, Michnick D A, Chickering T W, Revett T L, Ma J, Woolf E A, Comrack R A, Dussault G J, Woolf J, Goodearl A D J and Gearing D P. (1997). Mol. Cell Biol., 17, 4007-4014.
7. Carpenter G and Cohen S. (1979). Ann. Rev. Biochem., 48, 193-216.
8. Carraway K L, Weber J L, Unger M J, Ledesma J, Yu N and Gassmann M. (1997). Nature, 387, 512-516.
9. Chan S D, Antoniucci D M, Fok K S, Alajoki M L, Harkins R N, Thompson S A and Wada H G. (1995). J Biol Chem, 270, 22608-13.
10. Chang H, Riese D, Gilbert W, Stem D F and McMahan U J. (1997). Nature, 387, 509-512.
11. Chen X, Levkowitz G, Tzahar E, Karunagaran D, Lavi S, Ben-Baruch N, Leitner O, Ratzkin B J, Bacus S S and Yarden Y. (1996). J. Biol. Chem., 271, 7620-7629.
12. Cohen B D, Kiener P K, Green J M, Foy L, Fell H P and Zhang K. (1996). J. Biol. Chem., 271, 30897-30903.
13. Elenius K, Paul S, Allison G, Sun J and Klagsbrun M. (1997). EMBO J., 16, 1268-1278.
14. Erickson S L, O'Shea K S, Ghaboosi N, Loverro L, Frantz G, Bauer M, Lu L H and Moore M W. (1997). Development, 124, 4999-5011.
15. Gassmann M, Casagranda F, Orioli D, Simon H, Lai C, Klein R and Lemke G. (1995). Nature, 378, 390-394.
16. Graus-Porta D, Beerli, R. R. and Hynes N E. (1995). Mol. Cell Biol., 15, 1182-1191.
17. Gregory H, Walsh S and Hopkins C R. (1979). Gastroenterology, 77.
18. Guy P M, Platko J V, Cantley L C, Cerione R A and Carraway K L. (1994). Proc. Natl. Acad. Sci. USA, 91, 8132-8136.
19. Higashiyama S, Abraham J A, Miller J, Fiddes J C and Klagsbrun M. (1991). Science, 251; 936-939.
20. Higashiyama S, Horikawa M, Yamada K, Ichino N, Nakano N, Nakagawa T, Miyagawa J, Matsushita N, Nagatsu T, Taniguchi N and Ishiguro H. (1997). J. Biochem., 122, 675-80.
21. Holmes W E, Sliwkowski M X, Akita R W, Henzel W J, Lee J, Park J W, Yansura D, Abadi N, Raab H, Lewis G D, Shepard M, Wood W I, Goeddel D V and Vandlen R L. (1992). Science, 256, 1205-1210.
22. Jones J T, Ballinger M D, Pisacane P I, Lofgren J A, Fitzpatrick V D, Fairbrother W J, Wells J A and Sliwkowski M X. (1998). J Biol Chem, 273, 11667-11674.
23. Karunagaran D, Tzahar E, Beerli R R, Chen X, Graus-Porta D, Ratzkin B J, Seger R, Hynes N E and Yarden Y. (1996). EMBO J., 15, 254-264.
24. Karunagaran D, Tzahar E, Liu N, Wen D and Yarden Y. (1995). J. Biol. Chem., 270, 9982-9990.

25. Klapper L N, Vaisman N, Hurwitz E, Pinkas-Kramarski R, Yarden Y and Sela M. (1997). Oncogene, 14, 2099-2109.

26. Klapper, L. N., Kirschbaum, M. H., Sela, M. & Yarden, Y. (2000). Adv Cancer Res, 77, 25-79.

27. Kyte J and Doolittle R F. (1982). J. Mol. Biol., 157, 105-132.

28. Lee K F, Simon H, Chen H, Bates B, Hung M C and Hauser C. (1995). Nature, 378, 394-398.

29. Lin X-Z, Capooraco G, Chang P-Y, Ke X-H and Tam J P. (1988). Biochemistry, 27, 5640-5645.

30. Marchionni M A, Goodearl A D J, Chen M S, Bermingham-McDonogh O, Kirk C, Hendricks M, Denehy F, Misumi D, Sudhalter J, Kobayashi K, Wroblewski D, Lynch C, Baldassare M, Hiles I, Davis J B, Hsuan J J, Totty N F, Otsu M, McBury R N, Waterfield M D, Stroobant P and Gwynne D. (1993). Nature, 362, 312-318.

31. Marquardt H, Hunkapiller M H, Hood L E and Todaro G J. (1984). Science, 223, 1079-1082.

32. Massague J and Pandiella A. (1993). Ann. Rev. Biochem., 62, 515-54 1.

33. Meyer D and Birchmeier C. (1995). Nature, 378, 386-390.

34. Mosman T. (1983). J. Immunol. Methods, 65, 55-63.

35. Peles E, Bacus S S, Koski R A, Lu H S, Wen D, Ogden S G, Ben-Levy R and Yarden Y. (1992). Cell, 69, 205-216.

36. Peles E, Ben-Levy R, Tzahar E, Liu N, Wen D and Yarden Y. (1993). EMBO J., 12, 961-971.

37. Pinkas-Kramarski R, Eilam R, Alroy I, Levkowitz G, Lonai P and Yarden Y. (1997). Oncogene, 15, 2803-2815.

38. Pinkas-Kramarski R, Guarino B C, Shelly M, Wang L M, Lyass L, Alroy I, Alimandi M, Kuo A, Moyer J D, Lavi S, Eisenstein M, Ratzkin B J, Seger R, Bacus S S, Pierce J H, Andrews G C and Yarden Y. (1998). Mol. Cell Biol., 18, 6090-6101.

39. Pinkas-Kramarski R, Soussan L, Waterman H, Levkowitz G, Alroy I, Klapper L, Lavi S, Seger R, Ratzkin B, Sela M and Yarden Y. (1996). EMBO J., 15, 2452-2467.

40. Plowman G D, Culouscou J M, Whitney G S, Green J M, Carlton G W, Foy L, Neubauer M G and Shoyab M. (1993). Proc. Natl. Acad. Sci. USA, 90, 1746-1750.

41. Reddy C C, Niyogi S K, Wells A, Wiley H S and Lauffenburger D A. (1996). Nature Biotech., 14, 1696-1699.

42. Riese D J, Benningham Y, van Raaij T M, Buckley S, Plowman G D and Stern D F. (1996a). Oncogene, 12, 345-353.

43. Riese D I, Kim E D, Elenius K, Buckley S, Klagsbrun M, Plowman G D and Stem D F. (1996b). J. Biol. Chem., 271, 20047-20052.

44. Riese D J, van Raaij T M, Plowman G D, Andrews G C and Stern D F. (1995). Mol. Cell Biol., 15, 5770-5776.

45. Riethmacher D, Sonnenberg R E, Brinkmann V, Yamaai T, Lewin G R and Birchmeier C. (1997). Nature, 389, 725-30.

46. Samuel K and Altschul S F. (1990). Proc. Natl. Acad. Sci. USA, 87, 2264-68.

47. Shelly M, Pinkas-Kramarski R, Guarino B C, Waterman H, Wang L-M, Lyass L, Alimandi M, Kuo A, Bacus S S, Pierce J H, Andrews G C and Yarden Y. (1998). J. Biol. Chem., 273, 10496-10505.

48. Shing Y, Christofori G, Hanahan D, Ono Y, Sasada R, Igarashi K and Folkman J. (1993). Science, 259, 1604-7.

49. Shoyab M, Plowman G D, McDonald V L, Bradley J B and Todaro G I. (1989). Science, 243, 1074-1076.

50. Sliwkowski M X, Schaefer G, Akita R W, Lofgren J A, Fitzpatrick V D, Nuijens A, Fendly B M, Cerione R A, Vandlen R L and Carraway K L. (1994). J. Biol. Chem., 269, 14661-14665.

51. Smith T F and Waterman M S. (1981). Adv. Appl. Math., 2, 482-89.

52. Tam J P, Heath W F and Merrifield R B. (1983). J. Am. Chem. Soc., 105, 6442-6445.

53. Toyoda H, Komursaki T, Uchida D, Takayama Y, Isobe T, Okuyama T and Hanada K. (1995). J. Biol. Chem., 270, 7495-7500.

54. Tzahar E, Levkowitz G, Karunagaran D, Yi L, Peles E, Lavi S, Chang D, Liu N, Yayon A, Wen D and Yarden Y. (1994). J. Biol. Chem., 269, 25226-25233.

55. Tzahar E, Pinkas-Kramarski R, Moyer J, Klapper L N, Alroy I, Levkowitz G, Shelly M, Henis S, Eisenstein M, Ratzkin B J, Sela M, Andrews G C and Yarden Y. (1997). EMBO J., 16, 4938-4950.

56. Tzahar E, Waterman H, Chen X, Levkowitz G, Karunagaran D, Lavi S, Ratzkin B J and Yarden Y. (1996). Mol. Cell Biol., 16, 5276-5287.

57. Tzahar E and Yarden Y. (1998). BBA Rev. Cancer, 1377, M25-M37.

58. Wang L M, Kuo A, Alimandi M, Veri M C, Lee C C, Kapoor V, Ellmore N, Chen X H and Pierce J H. (1998). Proc. Natl. Acad. Sci. USA, 95, 6809-6814.

59. Wen D, Peles E, Cupples R, Suggs S V, Bacus S S, Luo Y, Trail G, Hu S, Silbiger S M, Ben-Levy R, Luo Y and Yarden Y. (1992). Cell, 69, 559-572.

60. Wen D, Suggs S V, Karunagaran D, Liu N, Cupples R L, Luo Y, Jansen A M, Ben-Baruch N, Trollinger D B, Jacobson V L, Meng T, Lu H S, Hu S, Chang D, Yanigahara D, Koski R A and Yarden Y. (1994). Mol. Cell Biol., 14, 1909-1919.

61. Tzahar E, et al. (1996) Mol. Cell. Biol. 16:5276-5287.

62. Yung Y, Dolginov Y, Yao Z, Rubinfeld H, Michael D, Hanoch T, Roubini E, Lando Z, Zharhari D and Seger R. (1997). FEBS J., 408, 292-296.

63. Zhang D, Sliwkowski M X, Mark M, Frantz G, Akita R, Sun Y, Hillan K, Crowley C, Brush J and Godowski P J. (1997). Proc. Natl. Acad. Sci. USA, 94, 9562-9567.

What is claimed is:

1. An isolated polypeptide at least 95% homologous to positions 4-50 of SEQ ID NO: 15 as determined using the BestFit software of the Wisconsin sequence analysis package, utilizing the Smith and Waterman algorithm, where gap creation penalty equals 8 and gap extension penalty equals 15, said polypeptide being capable of binding ErbB-4.

2. An isolated polypeptide comprising the amino acid sequence as set forth in SEQ ID NO: 15.

3. The isolated polypeptide of claim 1, wherein said polypeptide includes the amino acid sequence defined by amino acid coordinates 4-50 of SEQ ID NO:15.

4. The isolated polypeptide of claim 1, wherein said polypeptide includes the amino acid sequence defined by amino acid coordinates 1-90 of SEQ ID NO:15.

* * * * *